US012728108B1

(12) United States Patent
Jiang et al.

(10) Patent No.: US 12,728,108 B1
(45) Date of Patent: Sep. 8, 2026

(54) HEME OVERDRIVE REWIRES PAN-CANCER CELL METABOLISM

(71) Applicant: University of South Florida, Tampa, FL (US)

(72) Inventors: Rays Hong Yuan Jiang, Tampa, FL (US); Gloria Cruz Ferreira, Tampa, FL (US); Gregory Allen Hunter, Tampa, FL (US); Swamy Rakesh Adapa, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 18/119,575

(22) Filed: Mar. 9, 2023

Related U.S. Application Data

(60) Provisional application No. 63/269,073, filed on Mar. 9, 2022.

(51) Int. Cl.
*A61K 45/06* (2006.01)
*A61K 31/197* (2006.01)
*A61P 35/00* (2006.01)

(52) U.S. Cl.
CPC ............ *A61K 31/197* (2013.01); *A61K 45/06* (2013.01); *A61P 35/00* (2018.01)

(58) Field of Classification Search
CPC ........ A61K 31/197; A61K 45/06; A61P 35/00
See application file for complete search history.

(56) References Cited

U.S. PATENT DOCUMENTS

2016/0367674 A1* 12/2016 Goldberg ........... A61K 41/0061

OTHER PUBLICATIONS

Wang J et al. Mechanistic Investigation of the Specific Anticancer Property of Artemisinin and Its Combination with Aminolevulinic Acid for Enhanced Anticolorectal Cancer Activity. ACS Cent Sci. Jul. 26, 2017;3(7):743-750. (Year: 2017).*

Kim Yi, Cho KG, Jang SJ. Comparison of dual-time point 18F-FDG PET/CT tumor-to-background ratio, intraoperative 5-aminolevulinic acid fluorescence scale, and Ki-67 index in high-grade glioma. Medicine (Baltimore). Feb. 2019;98(8):e14397. (Year: 2019).*

Ghoochani A, Hsu EC, Aslan M, Rice MA, Nguyen HM, Brooks JD, Corey E, Paulmurugan R, Stoyanova T. Ferroptosis Inducers are a Novel Therapeutic Approach for Advanced Prostate Cancer. Cancer Res. Mar. 15, 2021;81(6):1583-1594. (Year: 2021).*

Duvigneau JC, Esterbauer H, Kozlov AV. Role of Heme Oxygenase as a Modulator of Heme-Mediated Pathways. Antioxidants (Basel). Oct. 11, 2019;8(10):475. (Year: 2019).*

Tibullo, D. et al. Nuclear Translocation of Heme Oxygenase-1 Confers Resistance to Imatinib in Chronic Myeloid Leukemia Cells. Curr. Pharmac. Design 19, 2765-2770, (2013).

Levine, A. J. & Puzio-Kuter, A. M. The control of the metabolic switch in cancers by oncogenes and tumor suppressor genes. Science 330, 1340-1344, (2010).

Luengo, A., et al. Targeting Metabolism for Cancer Therapy. Cell Chem Biol 24, 1161-1180, doi:10.1016/j.chembiol.2017.08.028 (2017).

Martinez-Outschoorn, U. E., et al. Cancer metabolism: a therapeutic perspective. Nat Rev Clin Oncol 14, 11-31, (2017).

Steinberg, P. Red Meat-Derived Nitroso Compounds, Lipid Peroxidation Products and Colorectal Cancer. Foods 8, (2019).

Fiorito, V., et al. The Multifaceted Role of Heme in Cancer. Frontiers in Oncology 9, (2020).

Martin, O. C. B. et al. Targeting Colon Luminal Lipid Peroxidation Limits Colon Carcinogenesis Associated with Red Meat Consumption. Cancer Prev Res (Phila) 11, 569-580, (2018).

Sohoni, S. et al. Elevated Heme Synthesis and Uptake Underpin Intensified Oxidative Metabolism and Tumorigenic Functions in Non-Small Cell Lung Cancer Cells. Cancer Research 79, 2511-2525, (2019).

Tsherniak, A. et al. Defining a Cancer Dependency Map. Cell 170, 564-576 e516, (2017).

Pacini, C. et al. Integrated cross-study datasets of genetic dependencies in cancer. Nat Commun 12, 1661, (2021).

Zhu, X. G. et al. Functional Genomics In Vivo Reveal Metabolic Dependencies of Pancreatic Cancer Cells. Cell Metab 33, 211-221. e216, (2021).

Canesin, G. et al. Scavenging of Labile Heme by Hemopexin Is a Key Checkpoint in Cancer Growth and Metastases. Cell Rep 32, 108181, (2020).

Elia, I. & Haigis, M. C. Metabolites and the tumour microenvironment: from cellular mechanisms to systemic metabolism. Nat Metab 3, 21-32, (2021).

Hooda, J. et al. Enhanced Heme Function and Mitochondrial Respiration Promote the Progression of Lung Cancer Cells. PLOS ONE 8, e63402, (2013).

Ma, Y. et al. The relationship between early embryo development and tumourigenesis. J Cell Mol Med 14, 2697-2701, (2010).

(Continued)

*Primary Examiner* — James H Alstrum-Acevedo
*Assistant Examiner* — Pierre Paul Eleniste
(74) *Attorney, Agent, or Firm* — Michele L. Lawson; Shumaker, Loop & Kendrick, LLP

(57) ABSTRACT

A novel method of treating cancer is presented. In cancer cells, genes are not needed to biosynthesize either early precursor (e.g., ALA, porphobilinogen) or heme end products for survival. Rather, cancer cells require genes for accumulation of heme intermediates (e.g., PPIX) for survival and they only require genes encoding HMBS ($3^{rd}$ step), UROS ($4^{th}$ step), UROD ($5^{th}$ step) and CPOX ($6^{th}$ step) for survival. This cancer metabolic rewiring process is termed "heme overdrive". This dependence on genes encoding these enzymes is present in all cancers and absent in all normal cells, thus heme overdrive provides an ideal cancer therapeutic target in terms of effectiveness, low toxicity, and applicability against a broad range of cancers. By inducing accumulation of heme precursor porphyrin metabolites, such as PPIX, and subsequently treating with a ferroptosis inducing compound, cancer cell death occurs with low to no toxicity in normal cells.

8 Claims, 50 Drawing Sheets
(33 of 50 Drawing Sheet(s) Filed in Color)

(56) References Cited

OTHER PUBLICATIONS

Smith, D. G. & Sturmey, R. G. Parallels between embryo and cancer cell metabolism. Biochem Soc Trans 41, 664-669, (2013).
Krieg, R. C., et al. Metabolic characterization of tumor cell-specific protoporphyrin IX accumulation after exposure to 5-aminolevulinic acid in human colonic cells. Photochem Photobiol 76, 518-525, (2002).
Merryweather-Clarke, A. T. et al. Distinct gene expression program dynamics during erythropoiesis from human induced pluripotent stem cells compared with adult and cord blood progenitors. BMC Genomics 17, 817, (2016).
Merryweather-Clarke, A. T. et al. Global gene expression analysis of human erythroid progenitors. Blood 117, e96-108. (2011).
Tirosh, I. et al. Dissecting the multicellular ecosystem of metastatic melanoma by single-cell RNA-seq. Science 352, 189-196, (2016).
Wu, S. Z. et al. Stromal cell diversity associated with immune evasion in human triple-negative breast cancer. The EMBO Journal 39, e104063, (2020).
Manwani, D. & Bieker, J. J. The erythroblastic island. Curr Top Dev Biol 82, 23-53, (2008).
Socolovsky, M. Exploring the erythroblastic island. Nat Med 19, 399-401, (2013).
Lukanidin, E. & Sleeman, J. P. Building the niche: the role of the S100 proteins in metastatic growth. Semin Cancer Biol 22, 216-225, (2012).
Icard, P. & Lincet, H. The cancer tumor: a metabolic parasite?. Bull Cancer 100, 427-433, (2013).
Li, X. Q. et al. NAMPT and NAPRT, Key Enzymes in NAD Salvage Synthesis Pathway, are of Negative Prognostic Value in Colorectal Cancer. Front Oncol 9, 736, (2019).
Krammer, B. & Plaetzer, K. ALA and its clinical impact, from bench to bedside. Photochem Photobiol Sci 7, 283-289, (2008).
Fisher, C. J. et al. ALA-PpIX mediated photodynamic therapy of malignant gliomas augmented by hypothermia. PLoS One 12, e0181654, (2017).
Fujishiro, T. et al. 5-Aminolevulinic acid-mediated photodynamic therapy can target human glioma stem-like cells refractory to antineoplastic agents. Photodiagnosis Photodyn Ther 24, 58-68, (2018).
Shan, L. et al. Increased hemoglobin and heme in MALDI-TOF MS analysis induce ferroptosis and promote degeneration of herniated human nucleus pulposus. Mol Med 27, 103, (2021).
Alexandrova, E. M. et al. Improving survival by exploiting tumour dependence on stabilized mutant p53 for treatment. Nature 523, 352-356, (2015).
Toh, T. B., et al. Epigenetics in cancer stem cells. Mol Cancer 16, 29, (2017).
Thakur, C. & Chen, F. Connections between metabolism and epigenetics in cancers. Semin Cancer Biol 57, 52-58, (2019).
Campbell, S. L. & Wellen, K. E. Metabolic Signaling to the Nucleus in Cancer. Mol Cell 71, 398-408, (2018).
Liao, R. et al. Discovering How Heme Controls Genome Function Through Heme-omics. Cell Rep 31, 107832, (2020).
Wang, T. et al. An Analysis of the Multifaceted Roles of Heme in the Pathogenesis of Cancer and Related Diseases. Cancers (Basel) 13, (2021).
Mense, S. M. & Zhang, L. Heme: a versatile signaling molecule controlling the activities of diverse regulators ranging from transcription factors to MAP kinases. Cell Research 16, 681-692, (2006).
W. S. Yang et al., Regulation of ferroptotic cancer cell death by GPX4. Cell 156, 317-331 (2014).
Sassa, S. & Kappas, A. Hereditary Tyrosinemia and the Heme Biosynthetic Pathway. The Journal of Clinical Investigation 71, 625-634, (1983).
Phillips, J. D. Heme biosynthesis and the porphyrias. Molecular genetics and metabolism 128, 164-177 (2019).
Han, Y., et al. lncRNA FLVCR1-AS1 drives colorectal cancer progression via modulation of the miR-381/RAP2A axis. Mol Med Rep 23, (2021).
Pan, Z. et al. LncRNA FLVCR1-AS1 promotes proliferation, migration and activates Wnt/β-catenin pathway through miR-381-3p/CTNNB1 axis in breast cancer. Cancer Cell Int 20, 214, (2020).
Yan, Z., et al. Long noncoding RNA FLVCR1-AS1 aggravates biological behaviors of glioma cells via targeting miR-4731-5p/E2F2 axis. Biochem Biophys Res Commun 521, 716-720, (2020).
Zhou, S. et al. FLVCR1 Predicts Poor Prognosis and Promotes Malignant Phenotype in Esophageal Squamous Cell Carcinoma via Upregulating CSE1L. Front Oncol 11, 660955, (2021).
Korolnek, T. & Hamza, I. Like iron in the blood of the people: the requirement for heme trafficking in iron metabolism. Front. Pharm. 5, 1-13, (2014).
Korolnek, T. & Hamza, I. Macrophages and iron trafficking at the birth and death of red cells. Blood 125, 2893-2897, (2015).
Schultz, I. J., Chen, C., Paw, B. H. & Hamza, I. Iron and Porphyrin Trafficking in Heme Biogenesis. Journal of Biological Chemistry 285, 26753-26759, (2010).
Valdés, P. A. et al. δ-aminolevulinic acid-induced protoporphyrin IX concentration correlates with histopathologic markers of malignancy in human gliomas: the need for quantitative fluorescence-guided resection to identify regions of increasing malignancy. Neuro Oncol 13, 846-856, (2011).
Hagiya, Y. et al. Pivotal roles of peptide transporter PEPT1 and ATP-binding cassette (ABC) transporter ABCG2 in 5-aminolevulinic acid (ALA)-based photocytotoxicity of gastric cancer cells in vitro. Photodiagnosis Photodyn Ther 9, 204-214, (2012).
Manceau, H. et al. TSPO2 translocates 5-aminolevulinic acid into human erythroleukemia cells. Biol Cell 112, 113-126, (2020).
Nakayama, T. et al. Dormant cancer cells accumulate high protoporphyrin IX levels and are sensitive to 5-aminolevulinic acid-based photodynamic therapy. Sci Rep 6, 36478, (2016).
Afonso, S., et al. Protoporphyrin IX and oxidative stress. Free Radic Res 31, 161-170, (1999).
Doll, S. et al. FSP1 is a glutathione-independent ferroptosis suppressor. Nature 575, 693-698, (2019).
Dixon, S. J. et al. Ferroptosis: An Iron-Dependent Form of Nonapoptotic Cell Death. Cell 149, 1060-1072, (2012).
Zhang, C. J. et al. Mechanism-Guided Design and Synthesis of a Mitochondria-Targeting Artemisinin Analogue with Enhanced Anticancer Activity. Angew Chem Int Ed Engl 55, 13770-13774, (2016).
Wang, J. et al. Haem-activated promiscuous targeting of artemisinin in Plasmodium falciparum. Nature Communications 6, 10111, (2015).
Chen, G.-Q. et al. Artemisinin compounds sensitize cancer cells to ferroptosis by regulating iron homeostasis. Cell Death & Differentiation 27, 242-254, (2020).
Fratz, E. J., et al. Expression of Murine 5-Aminolevulinate Synthase Variants Causes Protoporphyrin IX Accumulation and Light-Induced Mammalian Cell Death. PLOS ONE 9, e93078, (2014).
Yang, W. S. & Stockwell, B. R. Synthetic lethal screening identifies compounds activating iron-dependent, honapoptotic cell death in oncogenic-RAS-harboring cancer cells. Chem Biol 15, 234-245, (2008).

* cited by examiner

Figure 1A-C

CRISPR/Cas9 essentiality screens related to heme metabolism and oncogenesis.

| Cell Line Names | TFRC | UROD | FECH | SDHC | CYC1 | DGCR8 | HPX | HMOX1 |
|---|---|---|---|---|---|---|---|---|
| ASPC1_PANCREAS | -1.1551162 | -0.5974684 | -0.3173079 | -0.8330572 | -0.6992495 | -0.1927778 | 0.18582155 | 0.08515469 |
| KP4_PANCREAS | -0.4098856 | -0.8198479 | -0.3052094 | -0.7218426 | -0.8467593 | -0.3821767 | 0.09498258 | 0.15412676 |
| NCIH441_LUNG | -0.9422269 | -0.9361202 | -0.5628702 | -0.7416925 | -0.8553041 | -0.1970317 | 0.13995906 | 0.07177415 |
| SKMES1_LUNG | -0.5577955 | -0.2565052 | -0.0286887 | -0.3142007 | -0.1842988 | -0.4361252 | -0.0145409 | -0.0890296 |
| CJM_SKIN | -0.4389046 | -0.6016186 | -0.1113689 | -0.3473651 | -0.5804933 | -0.3730052 | 0.18852039 | 0.01655002 |
| SKMEL30_SKIN | -1.0494271 | -0.3543633 | -0.0115263 | -0.292561 | -0.4232123 | -0.1724953 | -0.1224128 | -0.1208495 |
| EFO27_OVARY | -1.1173979 | -0.9595874 | -0.2518573 | -0.6548122 | -1.2505115 | -0.2075994 | 0.10301298 | 0.09318417 |
| OV90_OVARY | -0.3902702 | -0.2227972 | 0.01797973 | -0.4236382 | -0.6644267 | -0.5298473 | 0.00113075 | -0.035699 |
| HT1080_SOFT_TISSUE | -0.6872113 | -0.8258028 | -0.0756393 | -0.6240429 | -0.9023851 | -0.2584285 | 0.06414206 | -0.0153907 |
| RH30_SOFT_TISSUE | -0.8166432 | -1.0392559 | -0.3504801 | -0.5783029 | -0.6629338 | -0.183207 | -0.1487749 | -0.1330071 |
| EFM19_BREAST | -0.7892353 | -0.9488874 | -0.6432665 | -0.7424395 | -0.6790104 | -0.2734717 | 0.03056947 | -0.0549097 |
| MDAMB415_BREAST | -0.6617661 | -0.1815233 | -0.1220571 | -0.7766341 | -0.8203696 | -0.149815 | 0.08141026 | 0.12311634 |

Figure 3

| AURKA | AURKB | MYC | KRAS | Source | Lineage | Histology | Gender |
|---|---|---|---|---|---|---|---|
| -0.8302203 | -1.0139685 | -1.5847615 | -1.1667528 | CCLE | Pancreas | carcinoma | female |
| -1.0133161 | -1.2342476 | -1.3072764 | -0.9152386 | CCLE | Pancreas | carcinoma | male |
| -1.0787122 | -1.1365792 | -1.4962563 | -0.8668031 | CCLE | Lung (NSCLC) | carcinoma | male |
| -0.9830374 | -1.2515921 | -1.2225132 | -0.2522715 | CCLE | Lung (NSCLC) | carcinoma | male |
| -0.9190264 | -1.1153095 | -1.6648237 | -0.2313934 | CCLE | Melanoma | malignant_melanoma | NA |
| -0.8765987 | -1.1620033 | -1.8088786 | -0.2690886 | CCLE | Melanoma | malignant_melanoma | male |
| -0.9189829 | -1.0877807 | -1.3678563 | -0.2862259 | CCLE | Ovary | carcinoma | female |
| -1.0798473 | -1.0722501 | -1.4261628 | -0.2714171 | CCLE | Ovary | carcinoma | female |
| -1.0181634 | -1.2221903 | -1.0026174 | -0.2840412 | CCLE | Soft Tissue | fibrosarcoma | male |
| -0.9590301 | -0.8055232 | -1.1185479 | -0.4059219 | CCLE | Soft Tissue | rhabdomyosarcoma | male |
| -0.7542134 | -0.8553924 | -1.3059972 | -0.2364266 | CCLE | Breast | carcinoma | female |
| -0.8705014 | -1.0721435 | -1.2318955 | -0.8702104 | CCLE | Breast | carcinoma | female |

Figure 3 cont.

| Age | Primary/Met | Achilles culture medium |
|---|---|---|
| 62 | metastasis | RPMI; 10% FBS |
| 50 | metastasis | DMEM:F12 (1:1); 10% FBS |
| NA | metastasis | RPMI; 10% FBS |
| 65 | metastasis | DMEM; 10% FBS |
| NA | metastasis | Hams F-12; 10% FBS |
| 67 | metastasis | RPMI; 10% FBS |
| 36 | metastasis | RPMI; 20% FBS; 0.1mM NEAA; 1mM Sodium Pyruvate |
| 64 | metastasis | DMEM; 10% FBS(Tony) [1:1 mixture of MCDB 105 medium with 1.5 g/L sodium bicarbonate added and Medium 199; 10% FBS] |
| 35 | metastasis | EMEM; 10% FBS |
| 17 | metastasis | RPMI; 10% FBS |
| 50 | metastasis | RPMI; 10% FBS |
| 38 | metastasis | L-15; 15% FBS; 2mM glutamine; 10mcg/mL Insulin; 10mcg/mL Glutathione |

CRISPR/Cas9 essentiality scores of diverse cell lines related to heme biosynthesis genes.

| Gene Symbol | | ABCG2 | ABCG2 | ABCG2 | ABCG2 | FLVCR1 | FLVCR1 |
|---|---|---|---|---|---|---|---|
| Cell line tissue types | Number of cell lines | Quantiles25 | Quantiles75 | Median | Mean | Quantiles25 | Quantiles75 |
| AUTONOMIC_GANGLIA | 11 | 0.2 | 0.2 | 0.2 | 0.19090909 | -0.1 | 0 |
| BONE | 6 | 0.1 | 0.225 | 0.1 | 0.15 | -0.1 | 0.05 |
| BREAST | 26 | 0.1 | 0.2 | 0.1 | 0.15769231 | -0.1 | 0.025 |
| CENTRAL_NERVOUS_SYSTEM | 36 | 0.1 | 0.1 | 0.1 | 0.09444444 | 0 | 0.1 |
| ENDOMETRIUM | 12 | 0 | 0.1 | 0.1 | 0.08333333 | -0.175 | 0.075 |
| HAEMATOPOIETIC_AND_LYMPHOID_TISSUE | 13 | 0.1 | 0.2 | 0.1 | 0.14615385 | -0.1 | 0.1 |
| KIDNEY | 16 | 0 | 0.2 | 0.2 | 0.125 | 0 | 0.1 |
| LARGE_INTESTINE | 25 | 0.1 | 0.3 | 0.2 | 0.188 | -0.1 | 0.05 |
| LIVER | 13 | 0.05 | 0.15 | 0.1 | 0.1 | 0 | 0 |
| LUNG | 47 | 0.1 | 0.2 | 0.1 | 0.11914894 | 0 | 0.1 |
| OESOPHAGUS | 10 | 0 | 0.125 | 0.1 | 0.1 | -0.025 | 0.025 |
| OVARY | 31 | 0.1 | 0.2 | 0.1 | 0.14516129 | 0 | 0.1 |
| PANCREAS | 23 | 0.1 | 0.1 | 0.1 | 0.1 | 0 | 0.1 |
| SKIN | 29 | 0.1 | 0.2 | 0.1 | 0.12413793 | -0.1 | 0.05 |
| SOFT_TISSUE | 6 | 0 | 0.15 | 0.05 | 0.08333333 | -0.05 | 0.1 |
| STOMACH | 10 | 0.1 | 0.2 | 0.2 | 0.16 | -0.05 | 0.1 |
| THYROID | 1 | 0.1 | 0.1 | 0.1 | 0.1 | 0 | 0 |
| UPPER_AERODIGESTIVE_TRACT | 8 | 0 | 0.25 | 0.1 | 0.1125 | -0.1 | 0.075 |
| URINARY_TRACT | 19 | 0.1 | 0.2 | 0.1 | 0.13684211 | -0.1 | 0 |

Figure 6

| FLVCR1 | FLVCR1 | FLVCR2 | FLVCR2 | FLVCR2 | FLVCR2 | SLC48A1 | SLC48A1 | SLC48A1 | SLC48A1 | ALAS1 | ALAS1 | ALAS1 |
|---|---|---|---|---|---|---|---|---|---|---|---|---|
| Median | Mean | Quantiles25 | Quantiles75 | Median | Mean | Quantiles25 | Quantiles75 | Median | Mean | Quantiles25 | Quantiles75 | Median |
| 0 | -0.01818182 | -0.4 | -0.2 | -0.3 | -0.28181818 | -0.1 | 0.1 | 0 | -0.009090909 | 0 | 0.1 | 0 |
| 0 | 0 | -0.25 | 0 | -0.1 | -0.13333333 | -0.1 | 0 | 0 | -0.033333333 | -0.1 | 0 | -0.05 |
| 0 | -0.05 | -0.1 | 0 | -0.1 | -0.08461538 | -0.025 | 0 | 0 | -0.019230769 | -0.2 | 0 | -0.1 |
| 0 | 0.01666667 | -0.1 | 0 | -0.1 | -0.06666667 | -0.175 | 0 | -0.1 | -0.091666667 | -0.1 | 0 | 0 |
| 0 | -0.05833333 | -0.1 | 0 | -0.05 | -0.05833333 | -0.1 | 0 | 0 | -0.025 | -0.1 | -0.025 | -0.1 |
| 0 | 0.01538462 | -0.25 | -0.2 | -0.2 | -0.20769231 | 0 | 0.05 | 0 | 0.007692308 | -0.5 | -0.15 | -0.5 |
| 0.05 | 0.04375 | -0.1 | -0.025 | -0.1 | -0.0875 | 0 | 0 | 0 | 0.00625 | -0.1 | 0 | 0 |
| 0 | -0.016 | -0.2 | 0 | -0.1 | -0.136 | -0.1 | 0 | 0 | -0.028 | -0.1 | 0.05 | 0 |
| 0 | -0.00769231 | -0.2 | 0 | -0.1 | -0.10769231 | -0.1 | 0 | 0 | -0.061538462 | -0.1 | 0 | 0 |
| 0 | 0.01276596 | -0.3 | -0.1 | -0.2 | -0.1893617 | 0 | 0.1 | 0 | 0.006382979 | -0.1 | 0 | -0.1 |
| 0 | -0.01 | -0.1 | 0 | -0.1 | -0.07 | -0.1 | 0 | 0 | -0.02 | -0.125 | -0.1 | -0.1 |
| 0 | 0.02903226 | -0.1 | 0 | -0.1 | -0.06451613 | -0.1 | 0 | 0 | -0.016129032 | -0.1 | 0 | 0 |
| 0 | 0.00434783 | -0.3 | -0.2 | -0.3 | -0.26956522 | 0 | 0.1 | 0 | 1.20676E-18 | -0.1 | 0 | -0.1 |
| 0 | -0.0137931 | -0.1 | 0 | 0 | -0.04482759 | -0.1 | 0 | -0.1 | -0.068965517 | -0.1 | 0 | 0 |
| 0 | 0 | -0.1 | 0.025 | -0.05 | -0.03333333 | -0.3 | 0.025 | -0.05 | -0.1 | -0.125 | 0 | -0.05 |
| 0 | -0.02 | -0.1 | -0.075 | -0.1 | -0.09 | -0.325 | 0 | -0.1 | -0.15 | -0.3 | 0 | -0.1 |
| 0 | 0 | 0 | 0 | 0 | 0 | -0.1 | -0.1 | -0.1 | -0.1 | 0 | 0 | 0 |
| 0 | -0.0125 | -0.1 | -0.1 | -0.1 | -0.1 | -0.1 | 0.1 | 0 | 0.0125 | -0.1 | -0.025 | -0.1 |
| 0 | -0.03157895 | -0.1 | 0 | -0.1 | -0.06842105 | -0.1 | 0 | -0.1 | -0.073684211 | -0.1 | 0 | 0 |

Figure 6 cont.

| ALAS1 | ALAD | ALAD | ALAD | ALAD | HMBS | HMBS | HMBS | HMBS | UROS | UROS | UROS | UROS |
|---|---|---|---|---|---|---|---|---|---|---|---|---|
| Mean | Quantiles25 | Quantiles75 | Median | Mean | Quantiles25 | Quantiles75 | Median | Mean | Quantiles25 | Quantiles75 | Median | Mean |
| 0.01818182 | -0.1 | 0 | 0 | -0.04545455 | -0.3 | -0.2 | -0.2 | -0.21818182 | -0.4 | -0.2 | -0.2 | -0.26363636 |
| -0.05 | -0.025 | 0.125 | 0.05 | 0.05 | -0.45 | 0 | -0.1 | -0.2 | -0.375 | -0.1 | -0.2 | -0.25 |
| -0.10769231 | -0.125 | 0 | -0.1 | -0.08076923 | -0.2 | -0.1 | -0.2 | -0.19230769 | -0.2 | -0.1 | -0.2 | -0.17692308 |
| -0.02777778 | -0.1 | 0 | 0 | -0.02222222 | -0.275 | -0.1 | -0.2 | -0.17777778 | -0.2 | -0.1 | -0.2 | -0.17777778 |
| -0.09166667 | -0.25 | -0.025 | -0.1 | -0.125 | -0.375 | -0.125 | -0.2 | -0.25 | -0.3 | -0.025 | -0.2 | -0.21666667 |
| -0.34615385 | -0.65 | 0 | -0.3 | -0.28461538 | -0.6 | -0.2 | -0.4 | -0.36923077 | -0.7 | -0.4 | -0.5 | -0.51538462 |
| -0.03125 | -0.1 | 0.075 | 0 | -0.025 | -0.2 | -0.1 | -0.15 | -0.14375 | -0.2 | -0.1 | -0.1 | -0.13125 |
| -0.048 | -0.2 | 0 | -0.1 | -0.088 | -0.3 | -0.1 | -0.2 | -0.2 | -0.3 | -0.15 | -0.2 | -0.224 |
| -0.05384615 | -0.1 | 0.05 | 0 | -0.01538462 | -0.3 | -0.1 | -0.2 | -0.21538462 | -0.25 | -0.1 | -0.1 | -0.17692308 |
| -0.09574468 | -0.1 | 0 | -0.1 | -0.1 | -0.3 | -0.1 | -0.2 | -0.22340426 | -0.3 | -0.1 | -0.2 | -0.23617021 |
| -0.11 | -0.2 | 0 | -0.1 | -0.1 | -0.35 | -0.175 | -0.2 | -0.27 | -0.225 | -0.1 | -0.1 | -0.16 |
| -0.0483871 | -0.1 | 0.1 | 0 | -0.01290323 | -0.2 | -0.1 | -0.1 | -0.13225806 | -0.2 | -0.1 | -0.1 | -0.13225806 |
| -0.05652174 | -0.1 | 0 | -0.1 | -0.09565217 | -0.3 | -0.1 | -0.2 | -0.23043478 | -0.3 | -0.1 | -0.2 | -0.21304348 |
| -0.05172414 | -0.1 | 0 | 0 | -0.03793103 | -0.3 | -0.1 | -0.2 | -0.2 | -0.2 | -0.1 | -0.2 | -0.16896552 |
| -0.06666667 | -0.025 | 0.1 | 0 | 0.01666667 | -0.3 | 0 | -0.1 | -0.13333333 | -0.4 | -0.075 | -0.15 | -0.2 |
| -0.15 | -0.35 | 0.025 | -0.15 | -0.16 | -0.5 | -0.275 | -0.4 | -0.39 | -0.425 | -0.2 | -0.3 | -0.33 |
| 0 | 0.1 | 0.1 | 0.1 | 0.1 | -0.2 | -0.2 | -0.2 | -0.2 | -0.2 | -0.2 | -0.2 | -0.2 |
| -0.0875 | 0 | 0.1 | 0.1 | 0.075 | -0.175 | 0 | -0.1 | -0.1 | -0.2 | -0.025 | -0.15 | -0.1375 |
| -0.06315789 | -0.1 | 0.1 | 0 | -0.01052632 | -0.4 | -0.2 | -0.2 | -0.25263158 | -0.3 | -0.1 | -0.2 | -0.19473684 |

Figure 6 cont.

| UROD | UROD | UROD | UROD | CPOX | CPOX | CPOX | CPOX | PPOX | PPOX | PPOX | PPOX | FECH |
|---|---|---|---|---|---|---|---|---|---|---|---|---|
| Quantiles25 | Quantiles75 | Median | Mean | Quantiles25 | Quantiles75 | Median | Mean | Quantiles25 | Quantiles75 | Median | Mean | Quantiles25 |
| -0.7 | -0.4 | -0.5 | -0.55454545 | -0.5 | -0.3 | -0.4 | -0.41818182 | -0.1 | 0 | 0 | -0.03636364 | -0.4 |
| -0.475 | -0.2 | -0.35 | -0.36666667 | -0.4 | -0.275 | -0.3 | -0.31666667 | -0.2 | 0 | -0.1 | -0.1 | -0.475 |
| -0.7 | -0.5 | -0.65 | -0.60384615 | -0.5 | -0.3 | -0.4 | -0.41923077 | -0.1 | 0 | 0 | -0.02692308 | -0.4 |
| -0.475 | -0.3 | -0.4 | -0.4 | -0.4 | -0.3 | -0.3 | -0.36111111 | -0.1 | 0 | -0.1 | -0.07222222 | -0.2 |
| -0.875 | -0.5 | -0.6 | -0.65833333 | -0.675 | -0.3 | -0.45 | -0.48333333 | -0.2 | -0.1 | -0.1 | -0.14166667 | -0.3 |
| -1 | -0.85 | -0.9 | -0.90769231 | -0.7 | -0.5 | -0.6 | -0.6 | -0.2 | -0.05 | -0.1 | -0.08461538 | -0.8 |
| -0.4 | -0.3 | -0.35 | -0.36875 | -0.475 | -0.225 | -0.4 | -0.35625 | -0.1 | -0.025 | -0.1 | -0.0875 | -0.2 |
| -0.85 | -0.5 | -0.6 | -0.664 | -0.5 | -0.35 | -0.4 | -0.444 | -0.2 | -0.05 | -0.1 | -0.108 | -0.4 |
| -0.55 | -0.3 | -0.4 | -0.42307692 | -0.45 | -0.3 | -0.4 | -0.39230769 | -0.15 | 0 | -0.1 | -0.08461538 | -0.3 |
| -0.8 | -0.5 | -0.6 | -0.63191489 | -0.5 | -0.3 | -0.4 | -0.43404255 | -0.2 | 0 | -0.1 | -0.11489362 | -0.4 |
| -0.7 | -0.475 | -0.6 | -0.6 | -0.5 | -0.375 | -0.45 | -0.44 | -0.225 | -0.1 | -0.15 | -0.16 | -0.525 |
| -0.8 | -0.3 | -0.5 | -0.56129032 | -0.5 | -0.3 | -0.4 | -0.38064516 | -0.1 | 0 | -0.1 | -0.05483871 | -0.3 |
| -0.8 | -0.5 | -0.7 | -0.64782609 | -0.5 | -0.4 | -0.4 | -0.43913043 | -0.1 | 0 | -0.1 | -0.06086957 | -0.5 |
| -0.6 | -0.4 | -0.5 | -0.51724138 | -0.5 | -0.3 | -0.3 | -0.36896552 | -0.1 | 0 | -0.1 | -0.07931034 | -0.3 |
| -0.85 | -0.375 | -0.8 | -0.81666667 | -0.425 | -0.275 | -0.35 | -0.35 | -0.1 | 0 | -0.05 | -0.05 | -0.325 |
| -1 | -0.55 | -0.75 | -0.74 | -0.55 | -0.3 | -0.4 | -0.43 | -0.2 | 0 | -0.1 | -0.12 | -0.525 |
| -0.7 | -0.7 | -0.7 | -0.7 | -0.3 | -0.3 | -0.3 | -0.3 | -0.1 | -0.1 | -0.1 | -0.1 | -0.1 |
| -0.575 | -0.325 | -0.45 | -0.4375 | -0.4 | -0.3 | -0.35 | -0.35 | -0.1 | 0 | 0 | -0.0375 | -0.3 |
| -0.7 | -0.4 | -0.5 | -0.56315789 | -0.5 | -0.3 | -0.4 | -0.37368421 | -0.1 | 0 | -0.1 | -0.1 | -0.4 |

Figure 6 cont.

| FECH | FECH | FECH |
|---|---|---|
| Quantiles75 | Median | Mean |
| -0.1 | -0.3 | -0.29090909 |
| -0.075 | -0.15 | -0.25 |
| -0.2 | -0.3 | -0.32307692 |
| -0.1 | -0.2 | -0.17222222 |
| -0.2 | -0.2 | -0.26666667 |
| -0.45 | -0.5 | -0.56153846 |
| -0.1 | -0.15 | -0.15625 |
| -0.2 | -0.3 | -0.336 |
| -0.1 | -0.2 | -0.26923077 |
| -0.2 | -0.3 | -0.33191489 |
| -0.275 | -0.35 | -0.37 |
| -0.1 | -0.2 | -0.21290323 |
| -0.2 | -0.3 | -0.3173913 |
| -0.1 | -0.2 | -0.20344828 |
| -0.1 | -0.2 | -0.21666667 |
| -0.2 | -0.25 | -0.35 |
| -0.1 | -0.1 | -0.1 |
| -0.1 | -0.2 | -0.2 |
| -0.2 | -0.3 | -0.27368421 |

Figure 6 cont.

**Partial heme biosynthetic pathway requirement for *in vitro* cancer cell growth**

| | | | | | | Types of cancer cell lines | |
|---|---|---|---|---|---|---|---|
| **Heme biosyntheis pathway essentiality (i.e. numbers of enzyme encoding genes are required for growth based on CRISPR KO)** | **Total Cell lines analyzed** | **No known export genes required** | **known export genes required** | **No known import genes required** | **Known import genes required** | AML | Breast |
| Enzyme (1 required) | 12 | 0 | 9 | 3 | 12 | 0 | 1 |
| Enzyme (2 required) | 69 | 5 | 57 | 17 | 74 | 1 | 6 |
| Enzyme (3 required) | 72 | 3 | 48 | 27 | 75 | 0 | 4 |
| Enzyme (4 required) | 68 | 5 | 42 | 31 | 73 | 1 | 7 |
| Enzyme (5 required) | 60 | 6 | 27 | 39 | 66 | 1 | 5 |
| Enzyme (6 required) | 13 | 5 | 10 | 8 | 18 | 1 | 1 |
| Enzyme (7 required) | 12 | 5 | 10 | 7 | 17 | 1 | 2 |
| Enzyme (8 required) | 6 | 1 | 4 | 3 | 7 | 2 | 0 |

Figure 7

| Chondrosarcoma | Colorectal | Endometrium | Esophagus | Ewing Sarcoma | Glioma | Kidney | Liver | Lung (NSCLC) | Lung (SCL) |
|---|---|---|---|---|---|---|---|---|---|
| 1 | 1 | 0 | 0 | 0 | 2 | 2 | 0 | 0 | 0 |
| 0 | 1 | 3 | 2 | 0 | 8 | 6 | 4 | 6 | 0 |
| 0 | 7 | 0 | 0 | 1 | 14 | 4 | 4 | 6 | 1 |
| 0 | 4 | 3 | 4 | 0 | 4 | 4 | 3 | 14 | 0 |
| 0 | 7 | 3 | 0 | 0 | 3 | 0 | 1 | 9 | 1 |
| 0 | 2 | 1 | 2 | 0 | 0 | 0 | 1 | 5 | 0 |
| 0 | 2 | 2 | 2 | 0 | 0 | 0 | 0 | 3 | 0 |
| 0 | 1 | 0 | 0 | 0 | 0 | 0 | 0 | 2 | 0 |

| Lymphoma (DLBCL) | Medulloblast oma | Melanoma | Meningioma | Neuroblasto ma | Osteosarcom a | Ovary | Pancreas | Soft Tissue | Stomach |
|---|---|---|---|---|---|---|---|---|---|
| 0 | 0 | 1 | 0 | 0 | 0 | 3 | 0 | 0 | 0 |
| 0 | 2 | 9 | 0 | 2 | 2 | 12 | 3 | 2 | 0 |
| 0 | 0 | 7 | 0 | 1 | 0 | 8 | 7 | 1 | 0 |
| 0 | 1 | 7 | 0 | 3 | 0 | 7 | 5 | 0 | 3 |
| 0 | 1 | 5 | 1 | 5 | 2 | 1 | 5 | 2 | 4 |
| 0 | 0 | 0 | 0 | 0 | 0 | 1 | 3 | 0 | 0 |
| 1 | 0 | 0 | 0 | 0 | 0 | 0 | 0 | 0 | 2 |
| 0 | 0 | 0 | 0 | 0 | 0 | 0 | 0 | 0 | 1 |

Figure 7 cont.

| T-cell ALL | T-cell Lymphoma (ALCL) | Thyroid | Upper Aerodigestive | Urinary Tract |
|---|---|---|---|---|
| 0 | 0 | 0 | 1 | 0 |
| 0 | 0 | 0 | 3 | 2 |
| 0 | 0 | 1 | 2 | 7 |
| 1 | 0 | 0 | 1 | 1 |
| 0 | 1 | 0 | 1 | 8 |
| 0 | 0 | 0 | 0 | 1 |
| 0 | 2 | 0 | 0 | 0 |
| 1 | 0 | 0 | 0 | 0 |

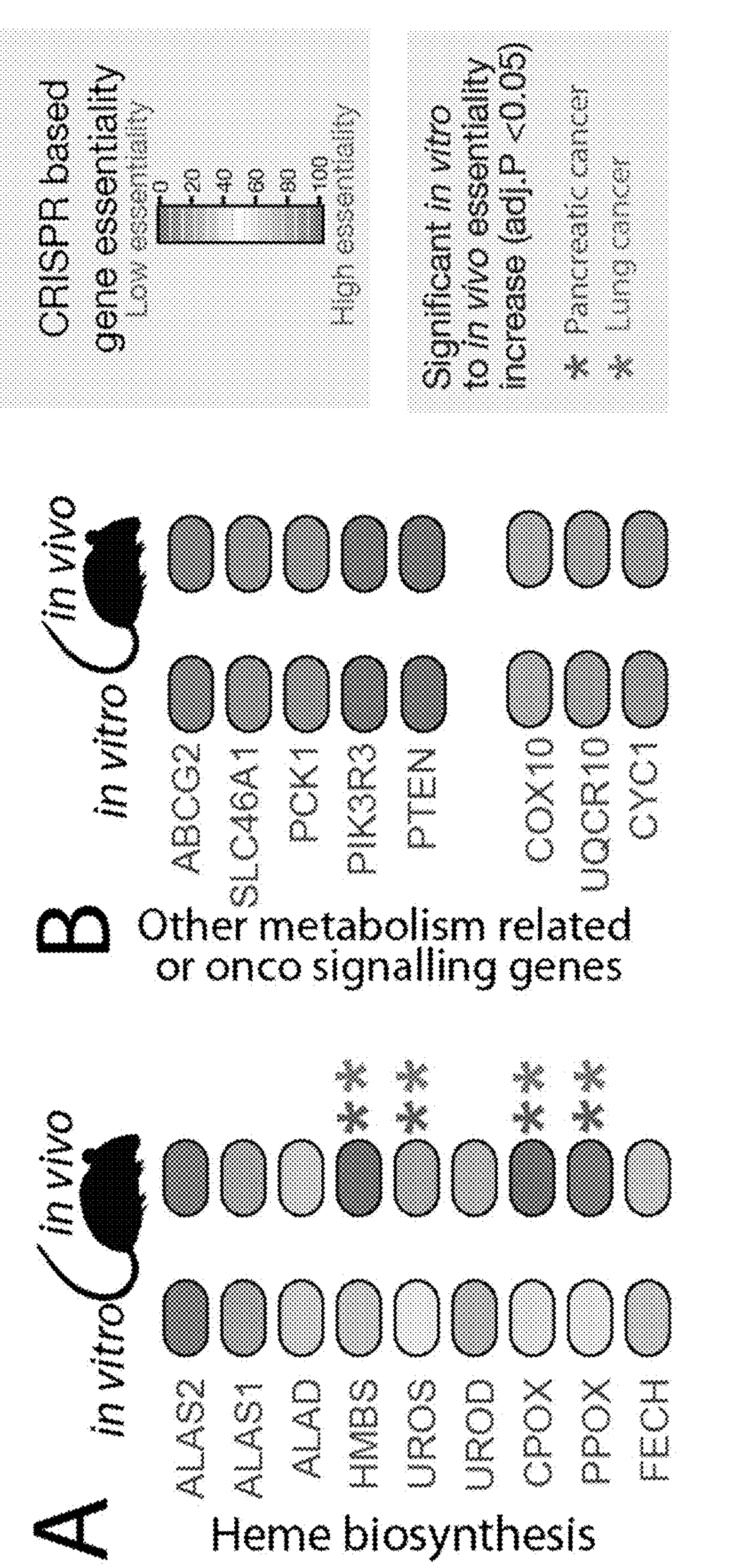
Figure 9A-B

*In vivo* murine CRISPR/CAS9 screen gene essentiality scores in pancreatic and lung cancers

| Gene | Zhu_invivoCRISPR_CellMet2021_in.vitro.mean pancrea | Zhu_invivoCRISPR_CellMet2021_in.vitro.pValue pancrea | Zhu_invivoCRISPR_CellMet2021_in.vivo.mean pancrea | Zhu_invivoCRISPR_CellMet2021_in.vivo.pValue pancrea | Zhu_invivoCRISPR_CellMet2021_vivo.vitro.mean pancrea | Zhu_invivoCRISPR_CellMet2021_vivo.vitro.pValue pancrea | in vitro score lung | in vivo score lung | in vitro score pancreas | C57BL/6J score pancreas |
|---|---|---|---|---|---|---|---|---|---|---|
| ALAS1 | -0.270657335 | 0.222936302 | -0.851869036 | 0.023775255 | -0.581211701 | 0.088410834 | | | | |
| ALAS2 | 0.053544574 | 0.809101259 | -0.48975966 | 0.132433982 | -0.543304234 | 0.210320008 | | | | |
| ALAD | -0.536967162 | 0.049936569 | -0.819520404 | 0.009167632 | -0.282553242 | 0.399638634 | | | | |
| HMBS | -1.452588745 | 0.024300286 | -3.412416234 | 0.000219585 | -1.95982749 | 0.012396194 | 0.15255049 | -2.93338461 | -0.49234742 | -3.85578111 |
| UROS | -0.773367958 | 0.050152905 | -2.000491252 | 0.01066135 | -1.227123294 | 0.048811026 | -0.30479972 | -2.62910638 | -1.16875512 | -2.433865492 |
| UROD | -1.839388654 | 0.001225985 | -2.928115458 | 0.002380499 | -1.088726804 | 0.059076681 | | | | |
| CPOX | -0.972856605 | 9.59579E-05 | -3.467424325 | 2.24691E-05 | -2.49456772 | 0.000204311 | 0.184646376 | -1.92106825 | -0.9230132 | -2.581492226 |
| PPOX | -0.889978807 | 0.000274895 | -2.894083745 | 7.17759E-05 | -2.004104938 | 0.000108327 | -0.07321267 | -2.40412859 | -1.56157246 | -3.690335639 |
| FECH | -1.51609966 | 0.035301692 | -2.20622772 | 0.019857599 | -0.69012806 | 0.239406962 | | | | |
| TFRC | -1.034296128 | 0.021072293 | -1.474231447 | 0.064629406 | -0.439935319 | 0.230265514 | | | | |
| CYC1 | -2.321876969 | 0.000296715 | -2.347942301 | 0.002834478 | -0.026065332 | 0.938563985 | | | | |
| GPX4 | -0.198031441 | 0.334332523 | -0.401625402 | 0.035714987 | -0.203593961 | 0.274751864 | | | | |

*significant changes from in vitro to in vivo are shaded

Figure 10

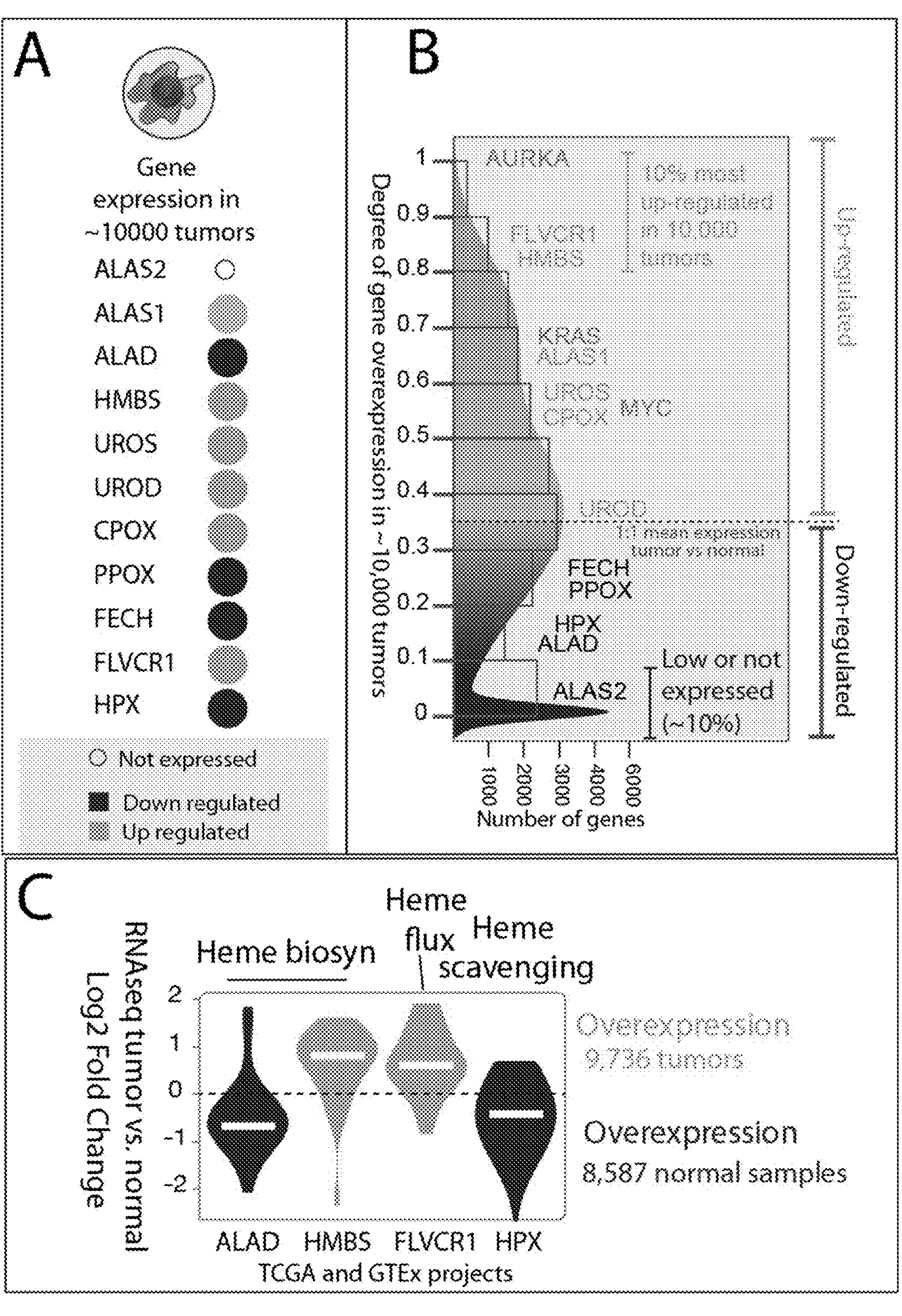
Figure 11A-C

Tissue-specific gene expression in patient-derived tumor samples (GTEX project and TGCA program) vs. normal individual samples

| GeneID | Tumor Average | Normal Average | ormal (Log2FoldCh | Upregulation Relative Score |
|---|---|---|---|---|
| ALAS2 | 0.21612903 | 0.96774194 | -0.7516129 | 9.677419355 |
| ALAS1 | 5.25806452 | 5.1516129 | 0.10645161 | 64.51612903 |
| ALAD | 4.52258065 | 5.01935484 | -0.4967742 | 12.90322581 |
| HMBS | 4.41935484 | 3.79032258 | 0.62903226 | 80.64516129 |
| UROS | 5.12903226 | 4.8 | 0.32903226 | 61.29032258 |
| UROD | 6.06451613 | 6.03225806 | 0.03225806 | 35.48387097 |
| CPOX | 3.34516129 | 3.07419355 | 0.27096774 | 58.06451613 |
| PPOX | 4.06451613 | 4.2483871 | -0.183871 | 32.25806452 |
| FECH | 3.46451613 | 3.62580645 | -0.1612903 | 35.48387097 |
| FLVCR1 | 2.45806452 | 1.78709677 | 0.67096774 | 83.87096774 |
| TFRC | 4.93870968 | 4.34516129 | 0.59354839 | 67.74193548 |
| HPX | 1.08064516 | 1.79032258 | -0.7096774 | 25.80645161 |
| AURKA | 3.5483871 | 1.55483871 | 1.99354839 | 93.5483871 |
| KRAS | 3.53225806 | 3.10645161 | 0.42580645 | 67.74193548 |
| MYC | 5.26774194 | 4.80967742 | 0.45806452 | 54.83870968 |

Figure 12

| Tumor code | Tumor types | MYC (N) | MYC (T) |
|---|---|---|---|
| ACC | Adrenocortical carcinoma | 4.9 | 3.2 |
| BLCA | Bladder Urothelial Carcinoma | 6.1 | 5.2 |
| BRCA | Breast invasive carcinoma | 6.7 | 5.7 |
| CESC | Cervical squamous cell carcinoma and endocervical adenocarcinoma | 5.4 | 5.9 |
| CHOL | Cholangio carcinoma | 4.3 | 5.4 |
| COAD | Colon adenocarcinoma | 5 | 7.1 |
| DLBC | Lymphoid Neoplasm Diffuse Large B-cell Lymphoma | 2.7 | 5.3 |
| ESCA | Esophageal carcinoma | 6.1 | 6.8 |
| GBM | Glioblastoma multiforme | 1.5 | 4.7 |
| HNSC | Head and Neck squamous cell carcinoma | 6.7 | 6.8 |
| KICH | Kidney Chromophobe | 3.8 | 2.6 |
| KIRC | Kidney renal clear cell carcinoma | 3.7 | 5.6 |
| KIRP | Kidney renal papillary cell carcinoma | 3.8 | 4.9 |
| LAML | Acute Myeloid Leukemia | 7 | 6.4 |
| LGG | Brain Lower Grade Glioma | 1.5 | 5.1 |
| LIHC | Liver hepatocellular carcinoma | 4.1 | 4.3 |
| LUAD | Lung adenocarcinoma | 5.2 | 4.9 |
| LUSC | Lung squamous cell carcinoma | 5.3 | 6.3 |
| OV | Ovarian serous cystadenocarcinoma | 6.1 | 5.9 |
| PAAD | Pancreatic adenocarcinoma | 4.7 | 5.3 |
| PCPG | Pheochromocytoma and Paraganglioma | 5.9 | 3.3 |
| PRAD | Prostate adenocarcinoma | 4.9 | 5.8 |
| READ | Rectum adenocarcinoma | 5 | 7.1 |
| SARC | Sarcoma | 5 | 5.3 |
| SKCM | Skin Cutaneous Melanoma | 7.1 | 6.2 |
| STAD | Stomach adenocarcinoma | 4.7 | 6 |
| TGCT | Testicular Germ Cell Tumors | 3.9 | 4 |
| THCA | Thyroid carcinoma | 4.6 | 3.3 |
| THYM | Thymoma | 2.7 | 5.3 |
| UCEC | Uterine Corpus Endometrial Carcinoma | 5.4 | 4.6 |
| UCS | Uterine Carcinosarcoma | 5.3 | 5 |

Figure 12 cont.

| KRAS (N) | KRAS (T) | AURKA (N) | AURKA (T) | HPX (N) | HPX (T) | TFRC (N) | TFRC (T) | FLVCR1 (N) | FLVCR1 (T) | FECH (N) |
|---|---|---|---|---|---|---|---|---|---|---|
| 2.8 | 2.8 | 1.4 | 3 | 1 | 0.5 | 4.3 | 3.8 | 1.9 | 1.8 | 4.3 |
| 3.6 | 3.5 | 1.5 | 4.3 | 0.6 | 0.5 | 4.7 | 5.4 | 1.7 | 2.4 | 3.7 |
| 3.2 | 4 | 1.1 | 3.9 | 2.2 | 2.9 | 4.4 | 5.2 | 2 | 3.2 | 3.7 |
| 3.4 | 3.6 | 1.1 | 4.7 | 1.8 | 0.4 | 4.2 | 6.1 | 2.3 | 2.5 | 3.5 |
| 2 | 3.5 | 0.7 | 3.1 | 11.7 | 2.8 | 2 | 4.7 | 0.7 | 2.6 | 3.2 |
| 3.6 | 3.8 | 1.6 | 5 | 1.4 | 0.6 | 4.9 | 6.5 | 1.9 | 3 | 3.4 |
| 2.2 | 3 | 0.7 | 4.4 | 0.3 | 0.2 | 2.6 | 5.8 | 0.6 | 2.5 | 2.7 |
| 4 | 4.6 | 2.6 | 4.7 | 0.8 | 0.4 | 5 | 6.5 | 1.7 | 3.3 | 3.7 |
| 3.1 | 3.3 | 0.9 | 3.5 | 1 | 1.1 | 4 | 5.2 | 1.6 | 2.2 | 3.2 |
| 3.6 | 3.7 | 2.5 | 4.4 | 0.2 | 0.2 | 4.3 | 5.7 | 1.3 | 2.1 | 3.4 |
| 3 | 3.6 | 1.4 | 2.7 | 0.5 | 0.2 | 4.1 | 5.1 | 1.7 | 0.9 | 4.5 |
| 3.6 | 3.4 | 1.5 | 2 | 0.3 | 0.6 | 4.2 | 4.3 | 1.8 | 1.9 | 5.3 |
| 3.1 | 3.3 | 1.4 | 2 | 0.5 | 0.6 | 4.2 | 3.2 | 1.6 | 1.8 | 4.8 |
| 3.9 | 4.5 | 6.5 | 3.4 | 0.3 | 0.4 | 8 | 7.1 | 4.1 | 3.5 | 5.7 |
| 3.1 | 3.7 | 0.9 | 1.6 | 1 | 0.7 | 4 | 4 | 1.6 | 2.3 | 3.2 |
| 2.3 | 2.3 | 1 | 3.1 | 11.2 | 10.2 | 3.2 | 3.9 | 0.8 | 2.1 | 3.3 |
| 3.6 | 4 | 1.5 | 3.7 | 1.5 | 0.7 | 6.3 | 4.9 | 2.2 | 2.7 | 3.4 |
| 3.6 | 4 | 1.4 | 4.4 | 1.5 | 0.5 | 6.2 | 7.1 | 2.3 | 2.9 | 3.4 |
| 3 | 3.4 | 1.8 | 4.1 | 1.8 | 0.5 | 6.1 | 5 | 2 | 2.1 | 3.6 |
| 2.1 | 3.8 | 0.5 | 2.9 | 1.1 | 0.8 | 3 | 4.7 | 1.2 | 2.3 | 2.5 |
| 2.3 | 2.9 | 1 | 1.7 | 0.4 | 0.8 | 4.6 | 3.2 | 1.7 | 2.5 | 3.4 |
| 3.1 | 3.2 | 1 | 1.5 | 2.1 | 1.6 | 3.8 | 3.1 | 2.1 | 2.5 | 3.7 |
| 3.5 | 3.9 | 1.4 | 5.1 | 1.5 | 0.6 | 4.8 | 6.5 | 1.8 | 3.1 | 3.4 |
| 2.9 | 3.3 | 1.5 | 3.9 | 0.3 | 0.8 | 3.8 | 4.1 | 1 | 1.6 | 4 |
| 3.3 | 3 | 1.4 | 4.2 | 1.9 | 0.4 | 4.5 | 4.8 | 2 | 2.4 | 3.2 |
| 3.3 | 4.1 | 1.5 | 4.5 | 1.1 | 0.4 | 3.9 | 5.7 | 1.6 | 3 | 3 |
| 3 | 4.7 | 4.8 | 4.8 | 2.2 | 1.5 | 4.2 | 4.6 | 2.9 | 3.5 | 3.1 |
| 3.3 | 3 | 1.1 | 1.2 | 1.5 | 0.4 | 4.2 | 3.4 | 2 | 1.7 | 3.9 |
| 2.2 | 2.8 | 0.7 | 3.5 | 0.3 | 0.5 | 2.6 | 3.5 | 0.6 | 2.5 | 2.7 |
| 3.3 | 3.4 | 0.9 | 4 | 1.7 | 0.8 | 4.3 | 5.3 | 2.3 | 2.9 | 3.7 |
| 3.3 | 3.4 | 0.9 | 4.7 | 1.8 | 0.9 | 4.3 | 4.7 | 2.4 | 2.4 | 3.8 |

Figure 12 cont.

| FECH (T) | PPOX (N) | PPOX (T) | CPOX (N) | CPOX (T) | UROD (N) | UROD (T) | UROS (N) | UROS (T) | HMBS (N) | HMBS (T) |
|---|---|---|---|---|---|---|---|---|---|---|
| 2.9 | 4.8 | 3.9 | 3.3 | 3 | 7.2 | 7.1 | 5.2 | 5.1 | 4.2 | 3.6 |
| 3.1 | 3.8 | 4.3 | 3.1 | 3.5 | 6.1 | 5.9 | 4.7 | 4.7 | 3.7 | 4.6 |
| 4 | 4.4 | 4.4 | 3.2 | 3.1 | 6.2 | 6 | 4.9 | 5.4 | 3.6 | 4.3 |
| 3.4 | 4.8 | 4.2 | 3.5 | 4.1 | 6.1 | 5.9 | 4.4 | 4.9 | 3.8 | 4.4 |
| 3.3 | 2.5 | 4.5 | 3 | 3 | 5.8 | 6.2 | 4.7 | 5.2 | 3.4 | 4.3 |
| 2.7 | 4.4 | 3.4 | 3.3 | 3.8 | 5.9 | 5.2 | 4.7 | 5 | 3.8 | 5.1 |
| 2.9 | 2.8 | 4 | 1.2 | 2.8 | 4.1 | 6 | 2.7 | 5.5 | 3.5 | 5 |
| 3.5 | 4 | 3.3 | 3.9 | 3.9 | 5.3 | 4.9 | 4.4 | 4.6 | 4 | 4.1 |
| 4 | 4.5 | 4.6 | 3.2 | 3.3 | 6 | 7.1 | 6.3 | 5.1 | 3.3 | 4.9 |
| 3.4 | 2.9 | 3.1 | 3 | 3.7 | 5.2 | 5.8 | 4.5 | 4.7 | 4.1 | 4.5 |
| 3.8 | 4.2 | 2.8 | 2.5 | 3.3 | 6.3 | 5.8 | 5.4 | 4.5 | 4.1 | 4.3 |
| 3.7 | 3.6 | 3.8 | 2.5 | 3 | 6.2 | 6.5 | 5.4 | 5 | 3.8 | 3.5 |
| 3.5 | 4 | 4.4 | 2.3 | 3 | 6.3 | 6.6 | 5.4 | 5.5 | 3.8 | 4.4 |
| 4.6 | 5.2 | 4.7 | 5.9 | 4 | 8.6 | 5.9 | 4.7 | 5.1 | 6.7 | 4.5 |
| 3.9 | 4.5 | 4.6 | 3.2 | 3.4 | 6 | 6.6 | 6.3 | 5.6 | 3.3 | 4.6 |
| 3.3 | 3 | 4 | 3.5 | 3 | 5.9 | 6.3 | 4.7 | 5.1 | 3.5 | 4.3 |
| 3.6 | 4.6 | 4.1 | 3.3 | 3.5 | 6 | 5.9 | 4.8 | 5.2 | 3.8 | 4.7 |
| 4 | 4.6 | 3.7 | 3.3 | 4 | 6 | 5.8 | 4.8 | 5 | 3.8 | 4.8 |
| 3.5 | 5.5 | 4.2 | 3.5 | 3 | 6.4 | 5.6 | 4.8 | 5.3 | 2.8 | 4.4 |
| 2.8 | 3.4 | 3.8 | 2.2 | 3.3 | 4.4 | 5.9 | 3.8 | 5 | 3.2 | 4.1 |
| 3.5 | 4.4 | 4.5 | 2.9 | 2.7 | 7.4 | 6 | 4.9 | 5.4 | 4.2 | 3.8 |
| 4.3 | 5 | 4.1 | 3.1 | 3 | 6 | 5.8 | 5.2 | 5.2 | 4 | 4.4 |
| 2.5 | 4.5 | 3.3 | 3.3 | 3.9 | 6 | 5.2 | 4.8 | 4.9 | 3.8 | 5 |
| 3.4 | 3.8 | 4.1 | 2.1 | 3.3 | 6.5 | 6.7 | 5.3 | 5.3 | 3.8 | 4 |
| 3.7 | 4.9 | 4.2 | 3.2 | 4.1 | 5.6 | 6.6 | 4.6 | 5 | 3.6 | 4.6 |
| 3.5 | 4 | 3.2 | 2.8 | 3.5 | 5.1 | 4.8 | 4.3 | 4.6 | 3.3 | 4.1 |
| 3.2 | 4.6 | 4.4 | 2.8 | 3.3 | 6.5 | 6.4 | 5.6 | 5 | 3.6 | 4.8 |
| 3.3 | 5.3 | 4 | 3.3 | 2.7 | 6.6 | 6.6 | 5.4 | 5.5 | 4.1 | 3.9 |
| 3.6 | 2.8 | 4.9 | 1.2 | 3.2 | 4.1 | 6.5 | 2.7 | 5.3 | 3.5 | 4.3 |
| 3.4 | 5.4 | 4.9 | 3.8 | 3.2 | 6.6 | 6.1 | 4.7 | 5.6 | 3.7 | 4.9 |
| 3.1 | 5.5 | 4.6 | 3.9 | 3.1 | 6.6 | 6.3 | 4.7 | 5.7 | 3.7 | 4.8 |

Figure 12 cont.

| ALAD (N) | ALAD (T) | ALAS1 (N) | ALAS1 (T) | ALAS2 (N) | ALAS2 (T) |
|---|---|---|---|---|---|
| 7.4 | 5.4 | 8.9 | 6.8 | 0.1 | 0.1 |
| 5 | 4 | 5.7 | 5.8 | 0.1 | 0 |
| 5.1 | 4.9 | 4.8 | 5 | 0.3 | 0 |
| 4.9 | 4.2 | 4.5 | 5.1 | 0.2 | 0.1 |
| 6.4 | 5.1 | 7.4 | 4.9 | 0.1 | 0.2 |
| 4.9 | 4.4 | 4.9 | 5.5 | 0.1 | 0 |
| 2.6 | 3.5 | 3.8 | 5.9 | 7.7 | 0 |
| 5.3 | 4.4 | 4.8 | 5.2 | 0.1 | 0.1 |
| 5.3 | 4.9 | 4.7 | 5.2 | 0.3 | 0.3 |
| 4.4 | 4 | 5.2 | 4.9 | 0 | 0 |
| 4.8 | 3.7 | 5.2 | 6 | 0.4 | 0.1 |
| 5.3 | 4.5 | 5.2 | 4.3 | 0.3 | 0.3 |
| 5.2 | 4.3 | 5.2 | 5.4 | 0.3 | 0.4 |
| 3.7 | 5.3 | 4.6 | 4.8 | 6.8 | 3.7 |
| 5.3 | 5.5 | 4.7 | 4.9 | 0.3 | 0.2 |
| 5.8 | 5.8 | 6.6 | 6.7 | 0.3 | 0.1 |
| 4.7 | 4.5 | 5.5 | 5.4 | 1.2 | 0.1 |
| 4.6 | 4.1 | 5.4 | 5 | 1.3 | 0.1 |
| 5.2 | 3.9 | 4 | 5.1 | 0.2 | 0.1 |
| 4.7 | 4.8 | 2.9 | 5.3 | 0.2 | 0.1 |
| 7 | 5.3 | 9.7 | 4.6 | 0 | 0.1 |
| 5.1 | 4.4 | 4.8 | 5 | 0.2 | 0.1 |
| 4.9 | 4.5 | 4.8 | 5.4 | 0.1 | 0 |
| 5.3 | 4.5 | 5.2 | 5 | 0.2 | 0.1 |
| 5.1 | 4.5 | 4.4 | 5.5 | 0.1 | 0 |
| 5.1 | 4.4 | 4.7 | 5.4 | 0.1 | 0.1 |
| 4.7 | 4.4 | 4.7 | 5.1 | 0.3 | 0 |
| 5.3 | 4.9 | 4.8 | 4.9 | 0.5 | 0.1 |
| 2.6 | 4.4 | 3.8 | 4.6 | 7.7 | 0 |
| 4.9 | 4 | 4.4 | 5.3 | 0.2 | 0.1 |
| 5 | 3.7 | 4.4 | 5 | 0.3 | 0.1 |

Figure 12 cont.

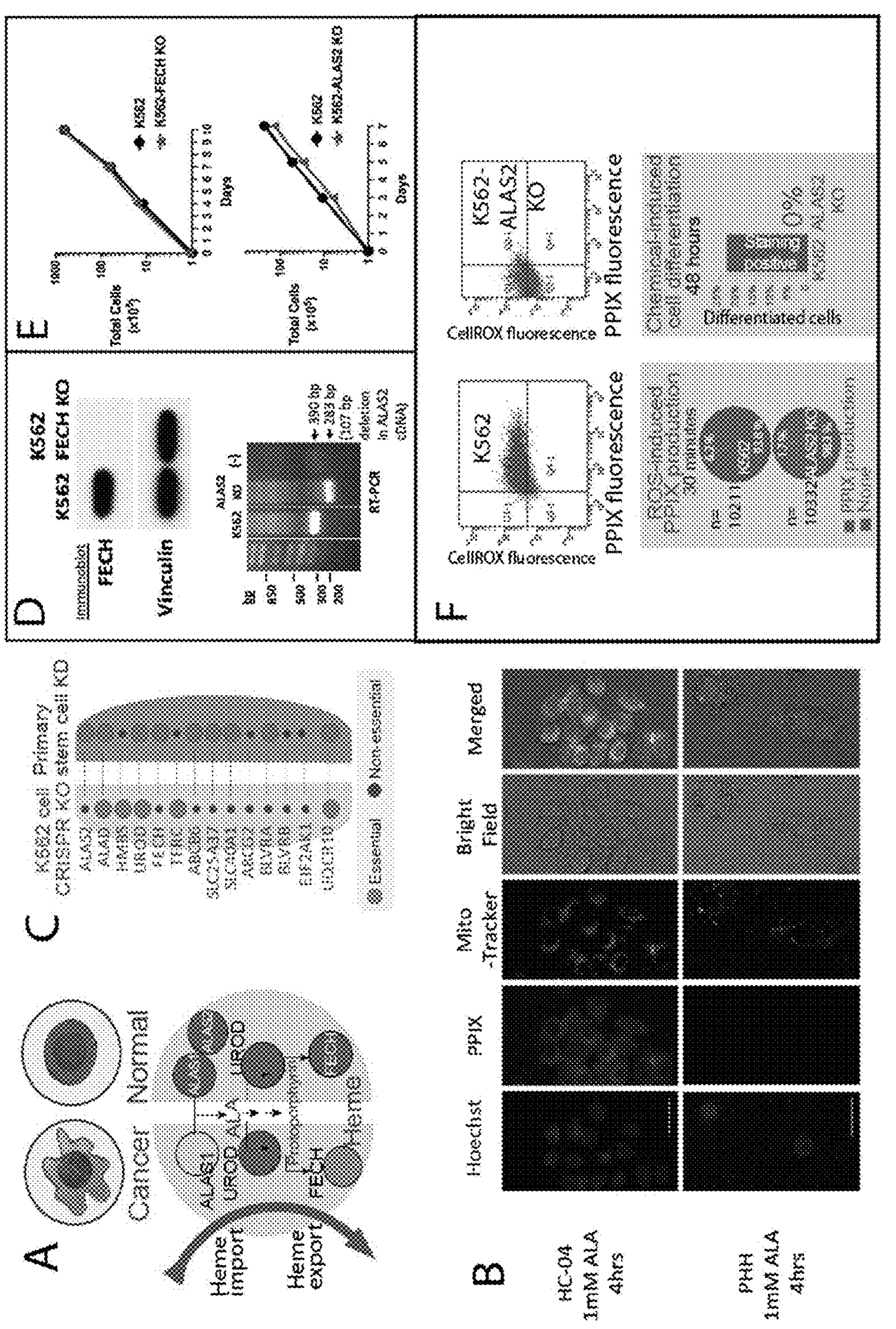
Figure 13A-F

G

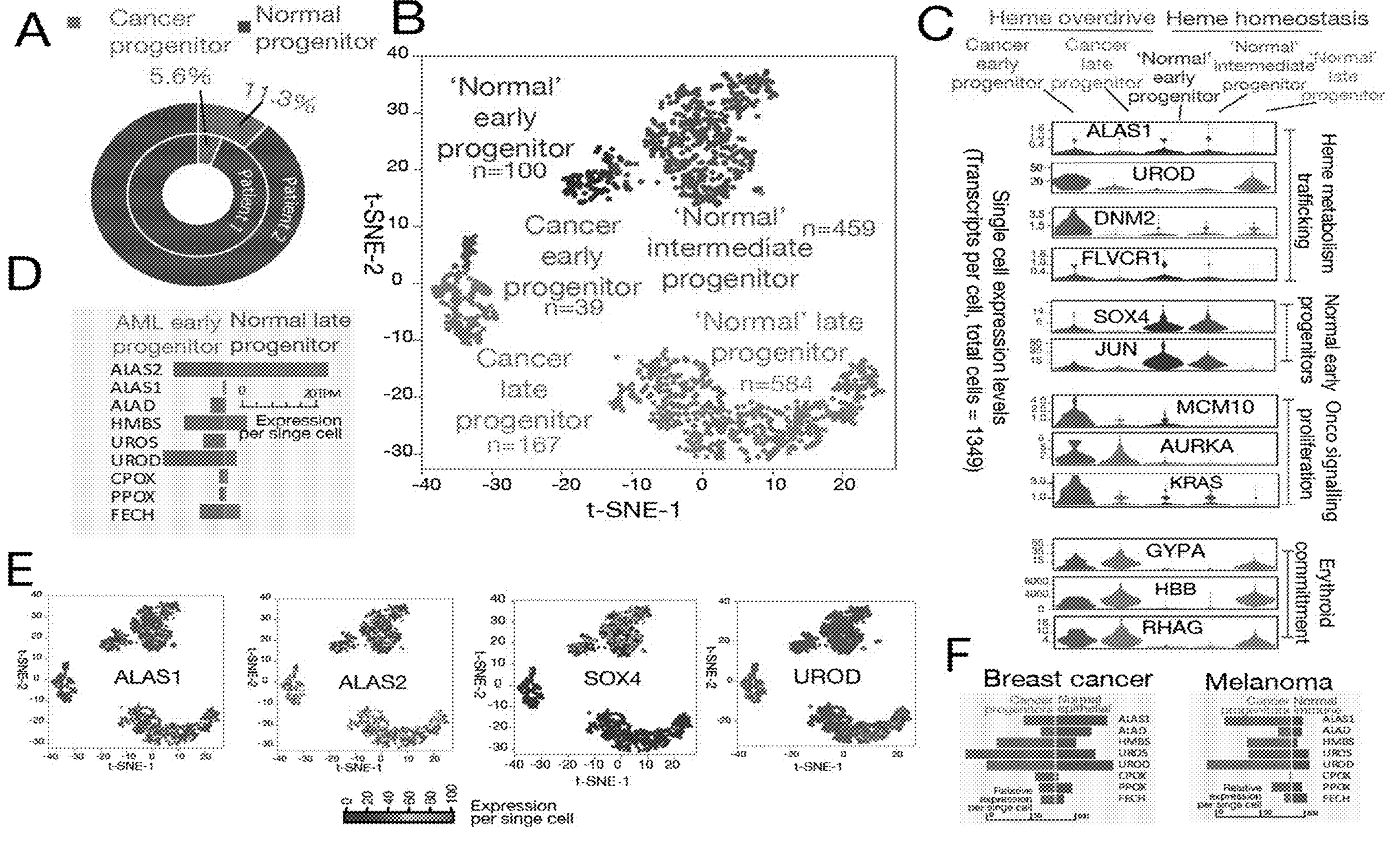
Figure 14A-F

G
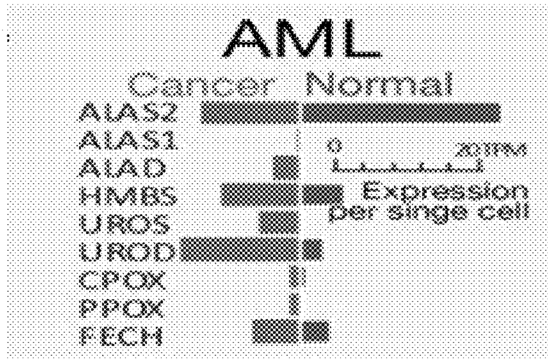
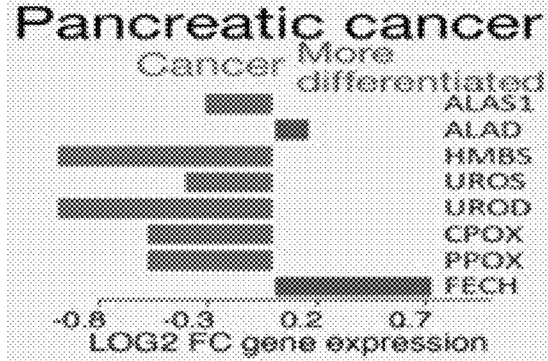
Figure 14G

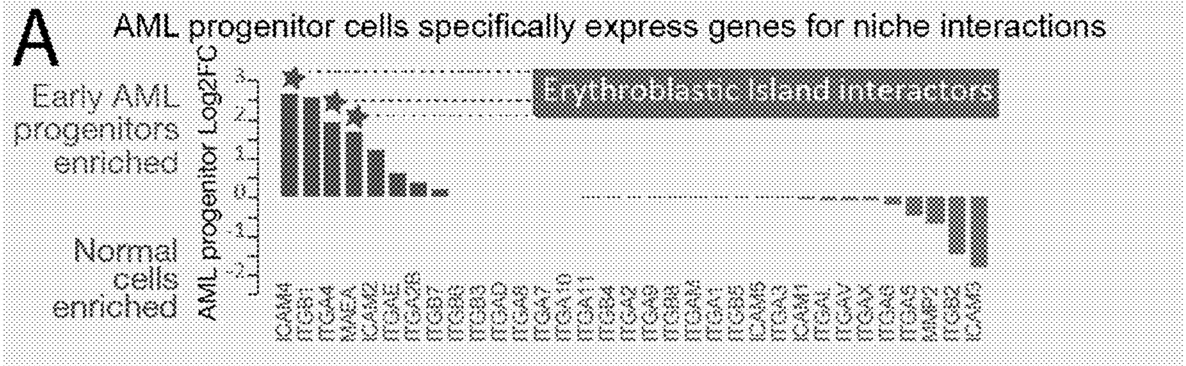
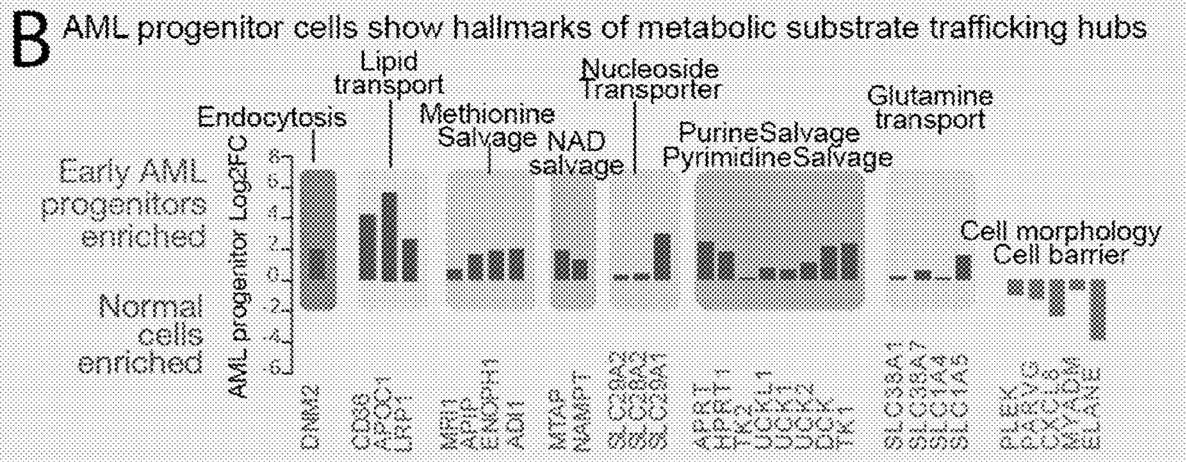
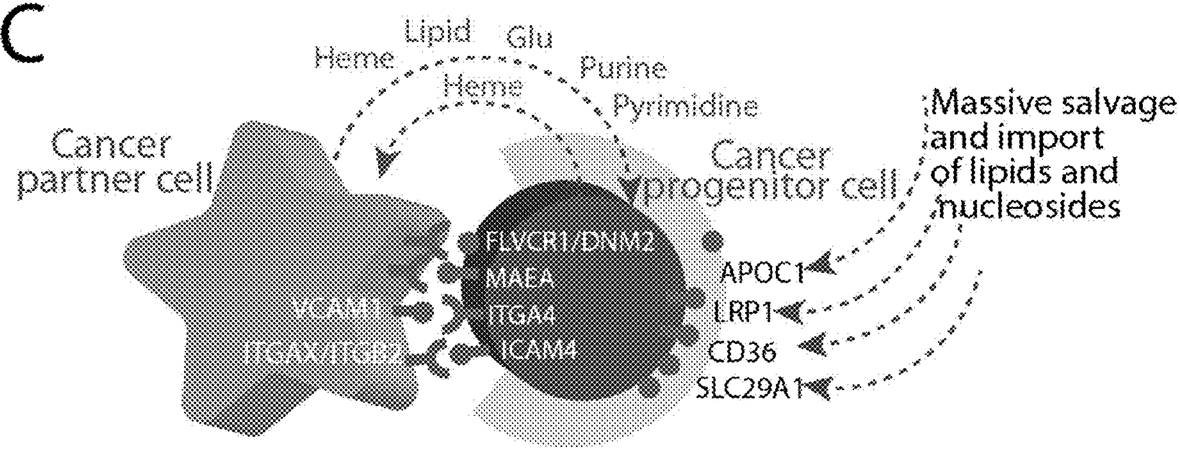
Figure 15A-C

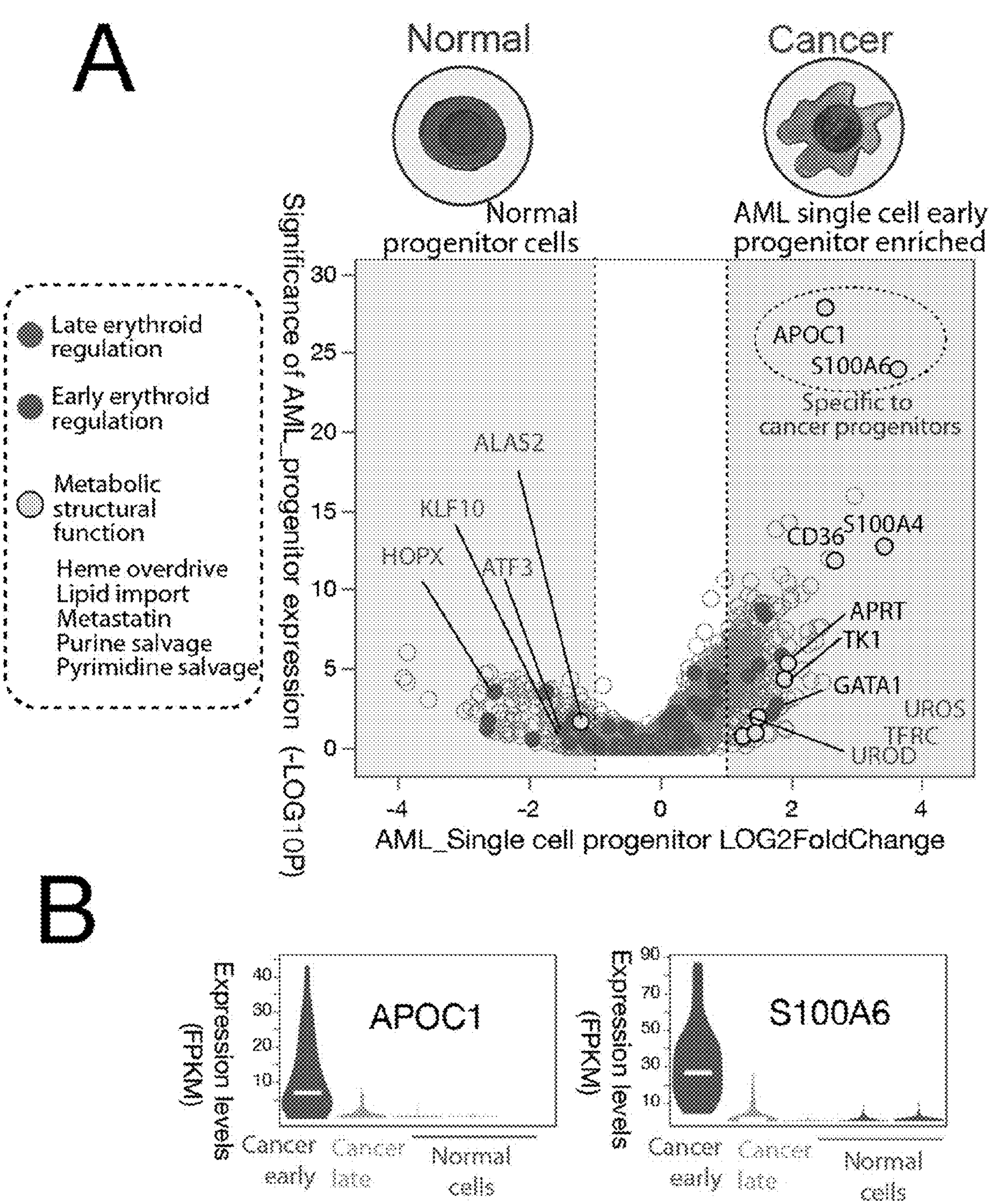
Figure 16A-B

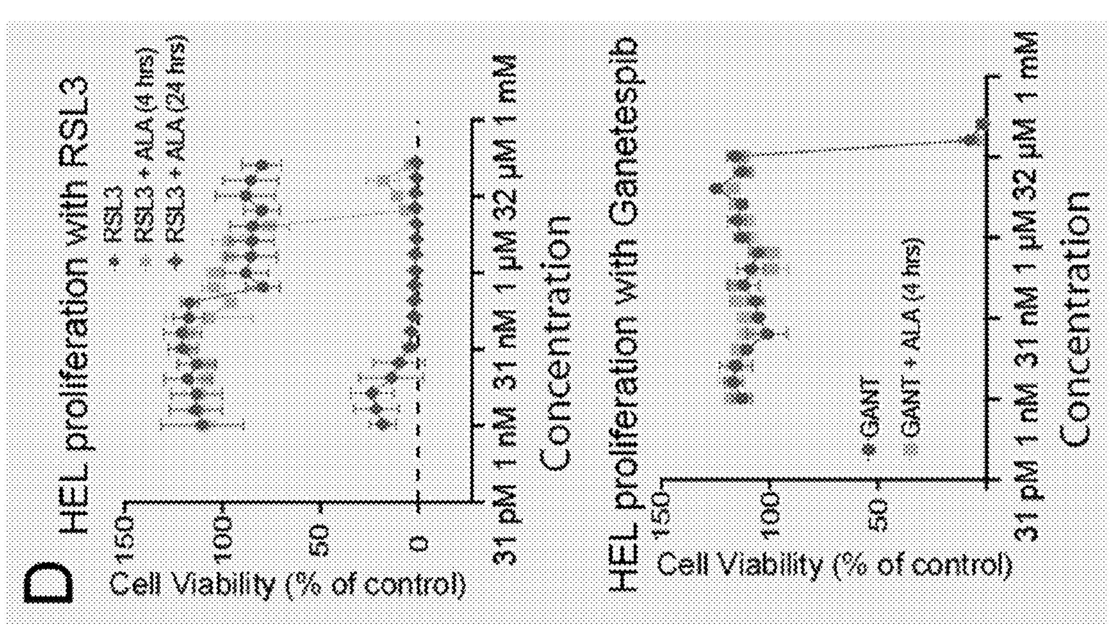
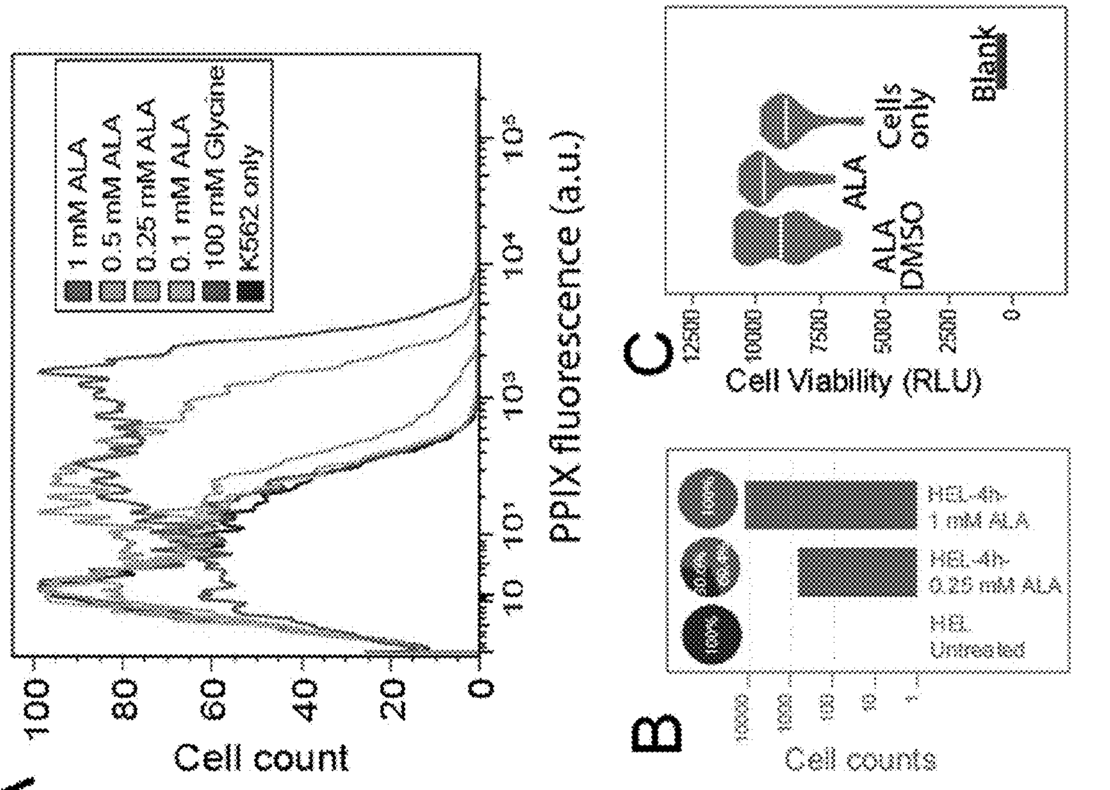
Figure 17A-D

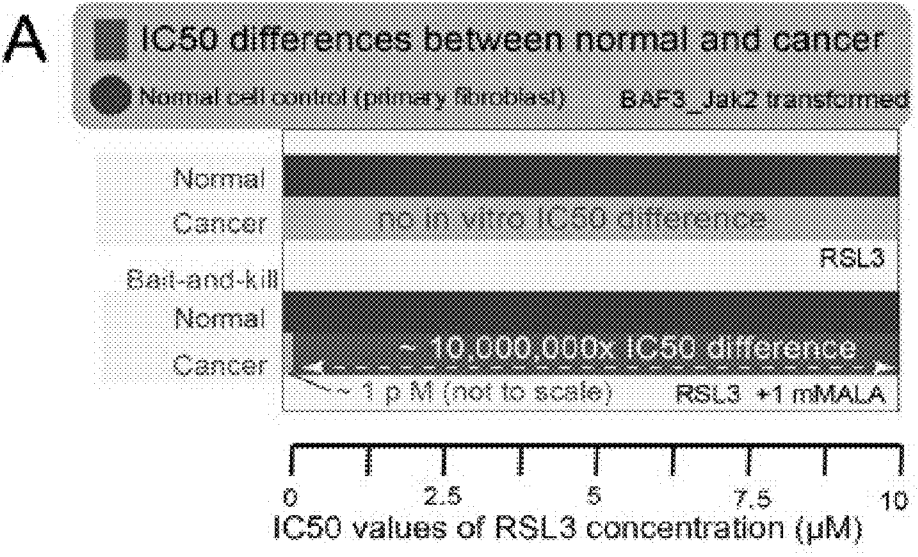
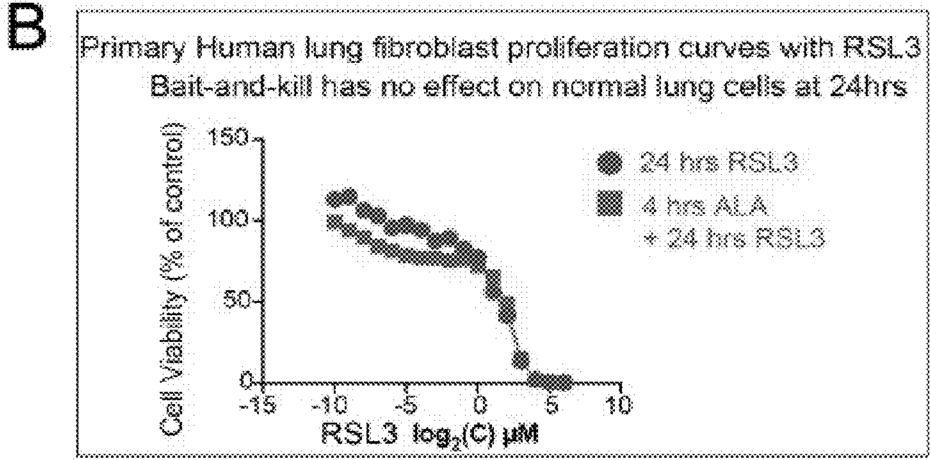
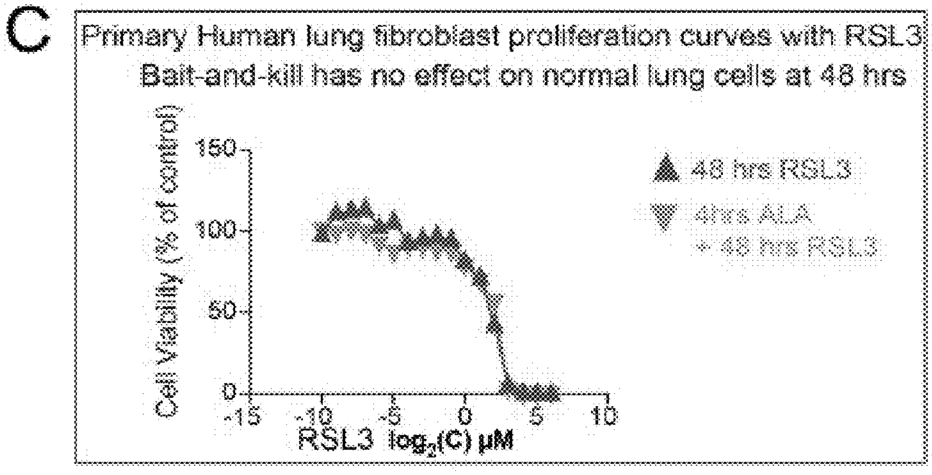
Figure 18A-C

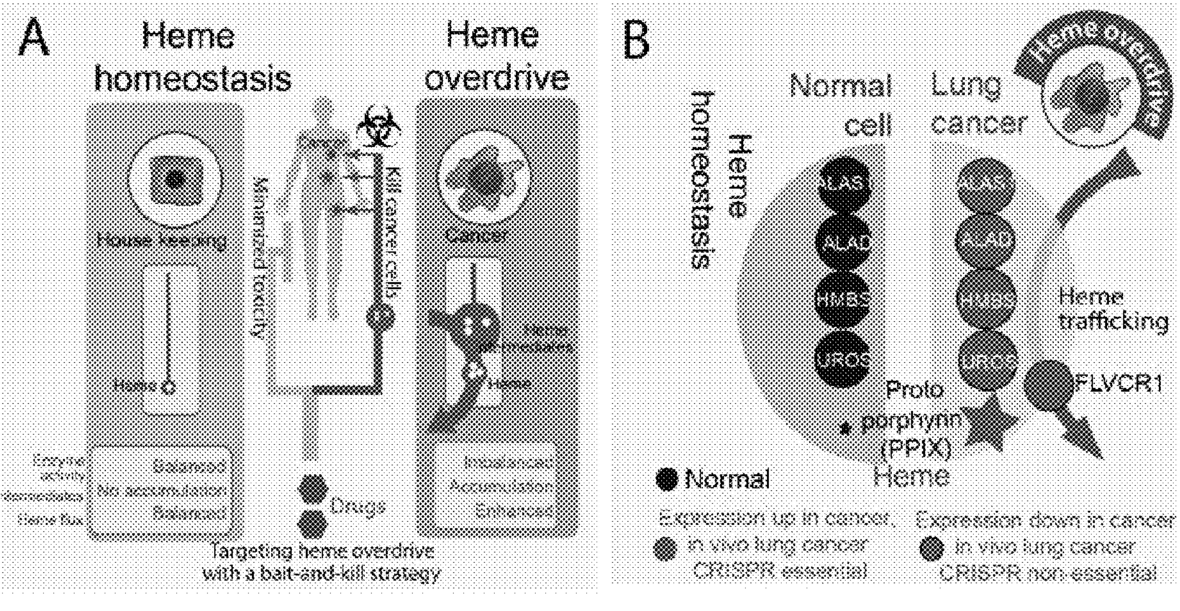
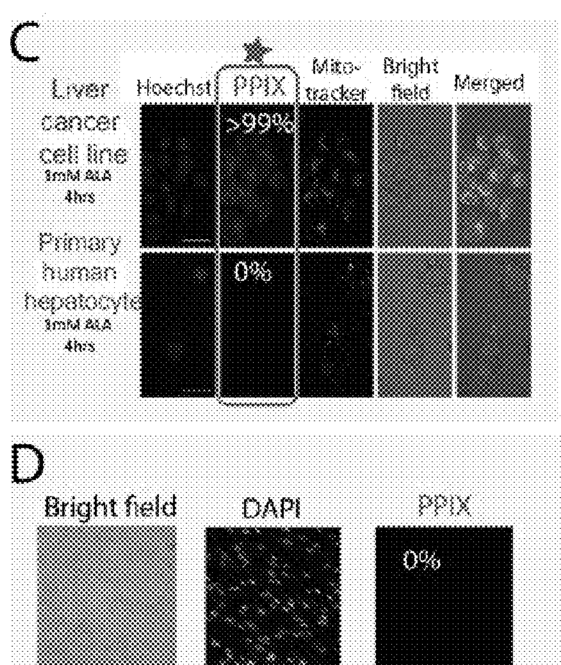
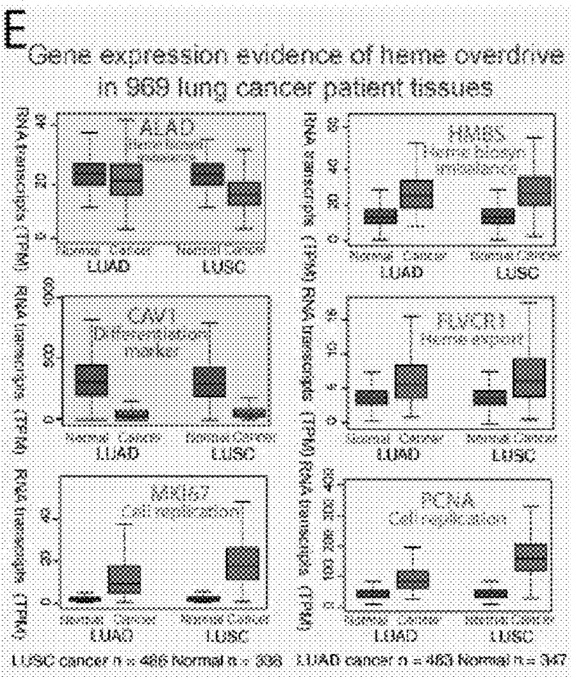
Figure 22A-E

Figure 25A-B

A CAFs from a lung adenocarcinoma patient show heme overdrive
Cell count
CAF only
CAF + ALA
PPIX fluorescence (a.u.)
CAF (heme overdrive)
No PPIX 0%
76%
ALA induced PPIX
24%
PPIX without ALA induction
Normalized CAF loses heme overdrive
ALA induced PPIX 0%
No PPIX 100%
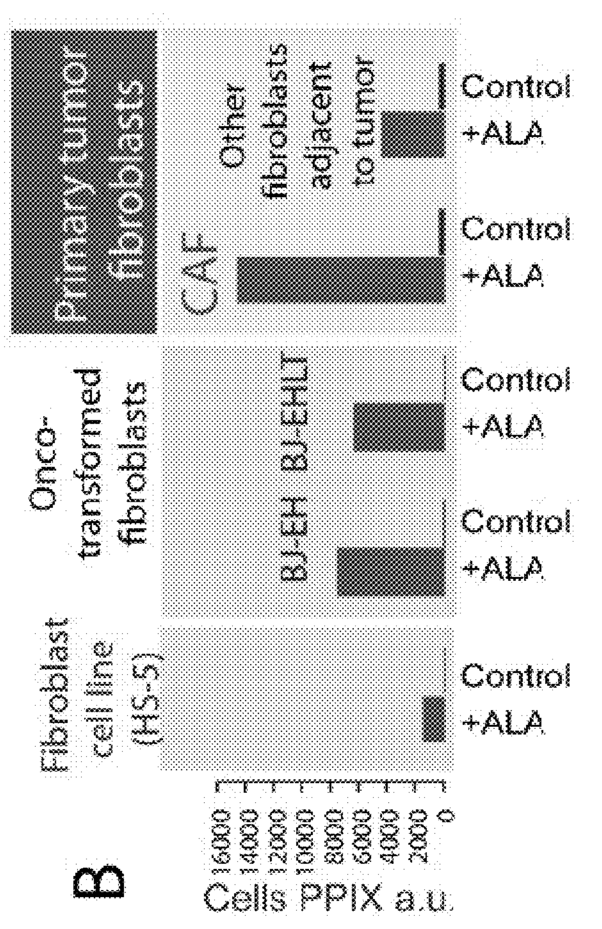
Figure 27A-B

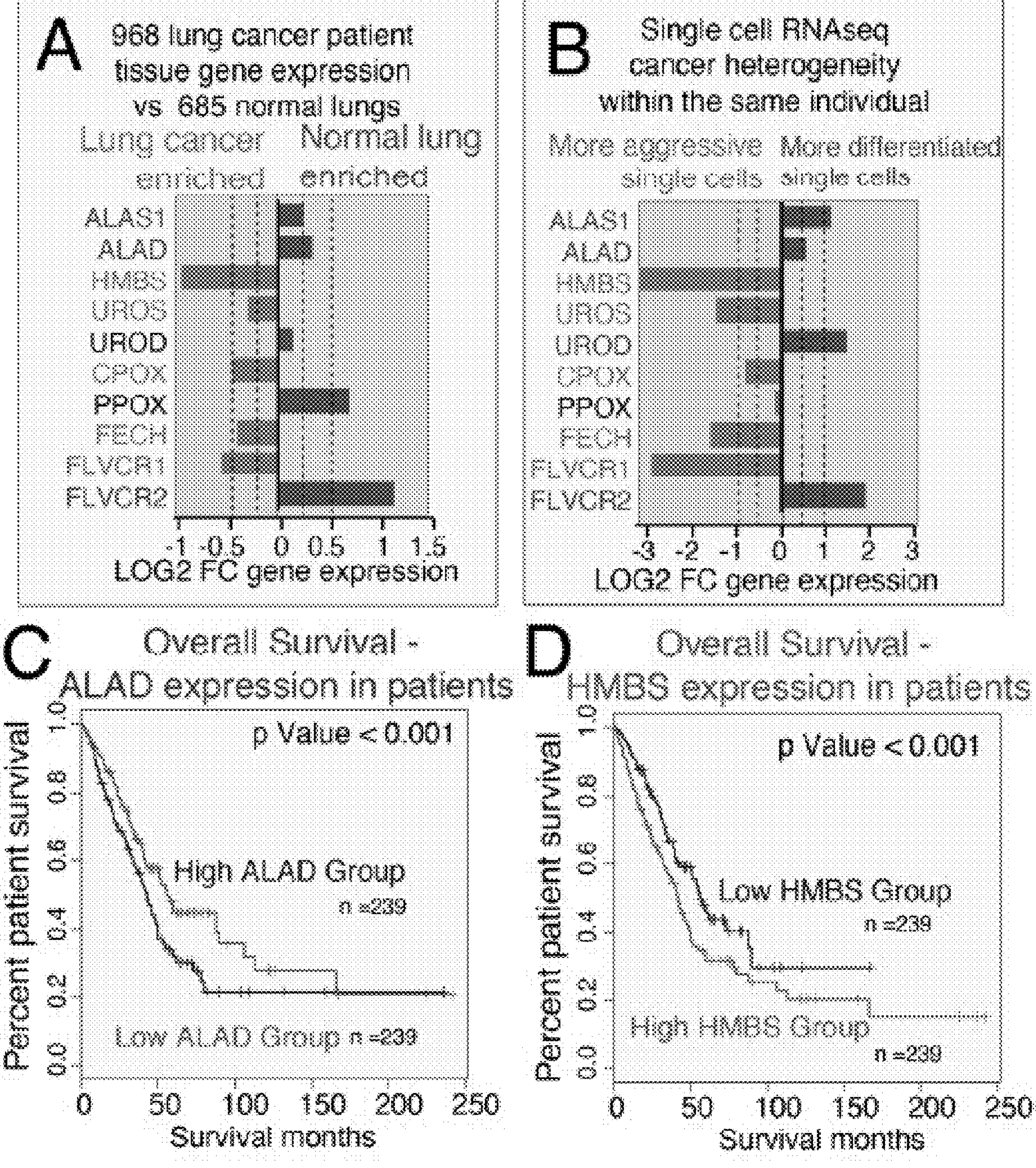
Figure 28A-D

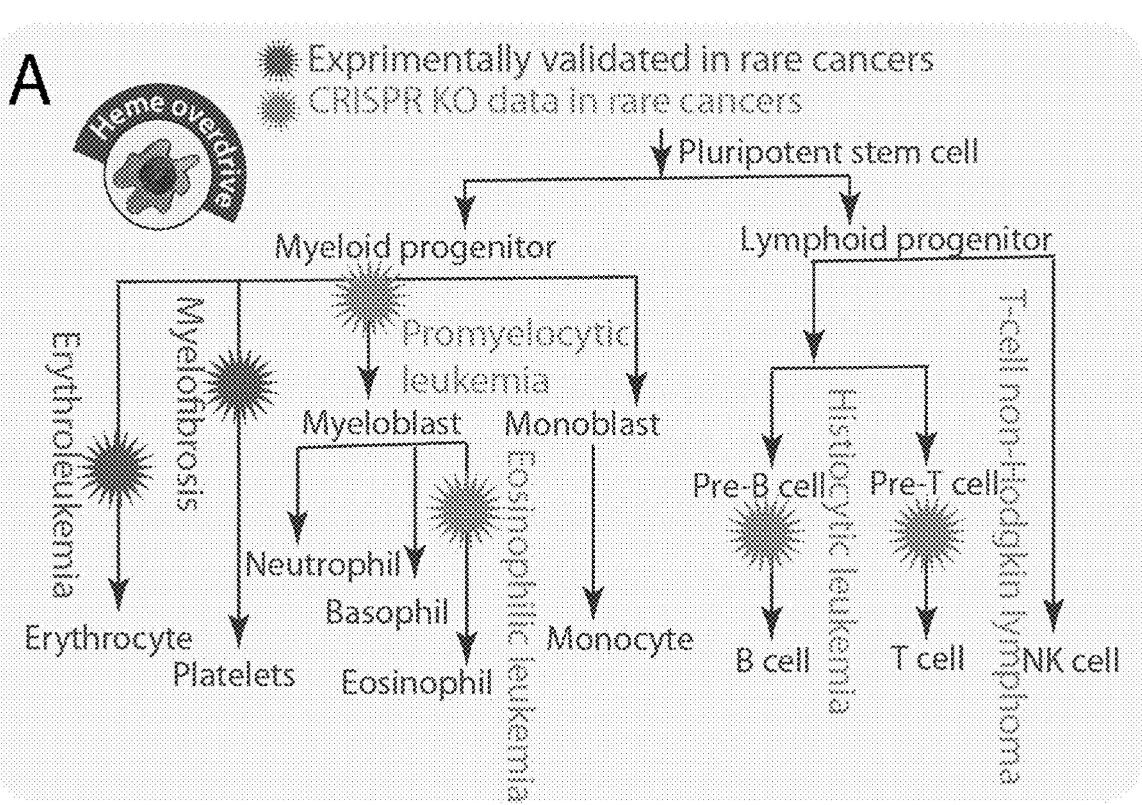
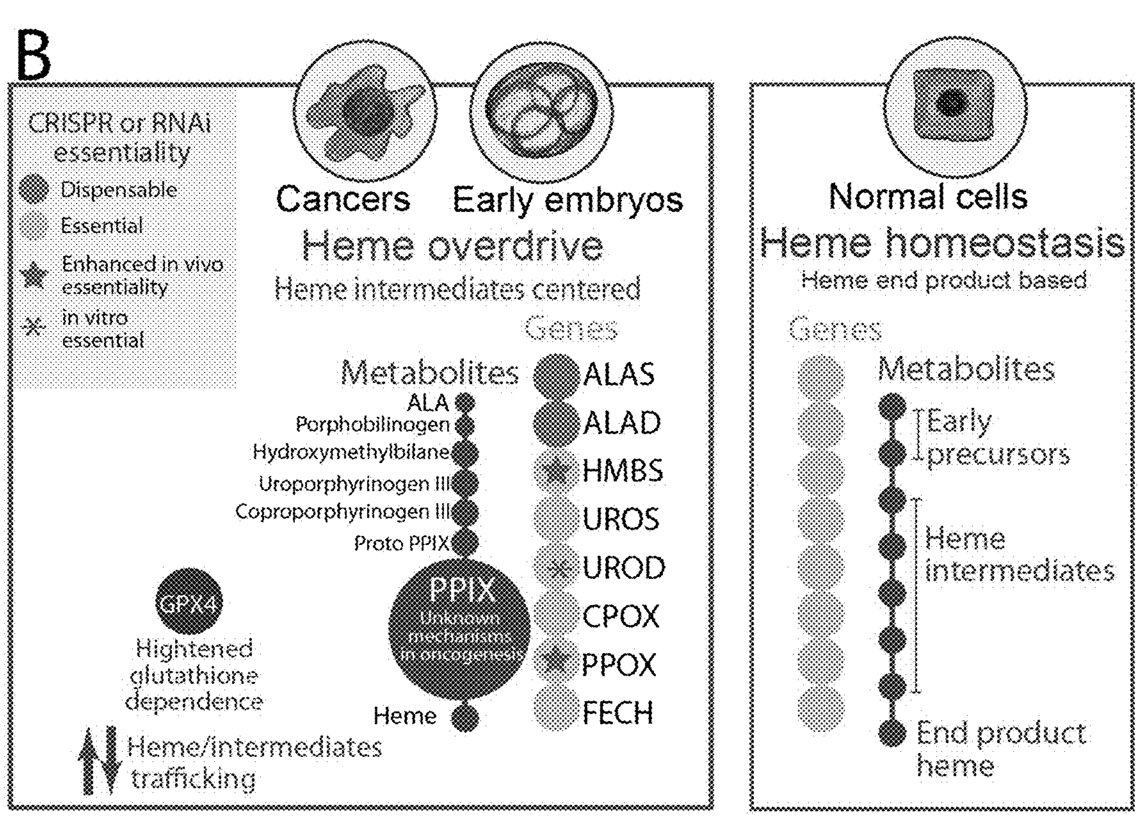
Figure 29A-B

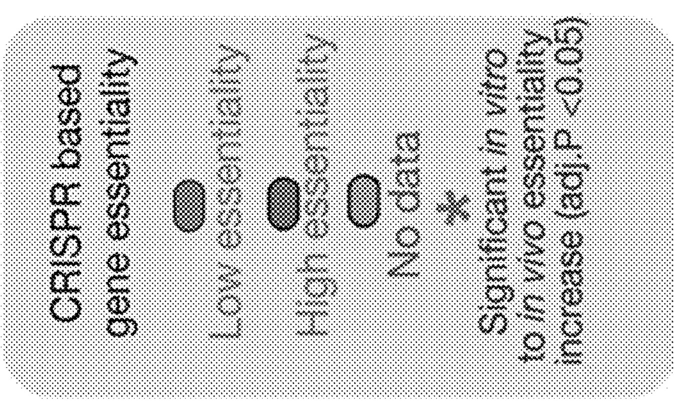
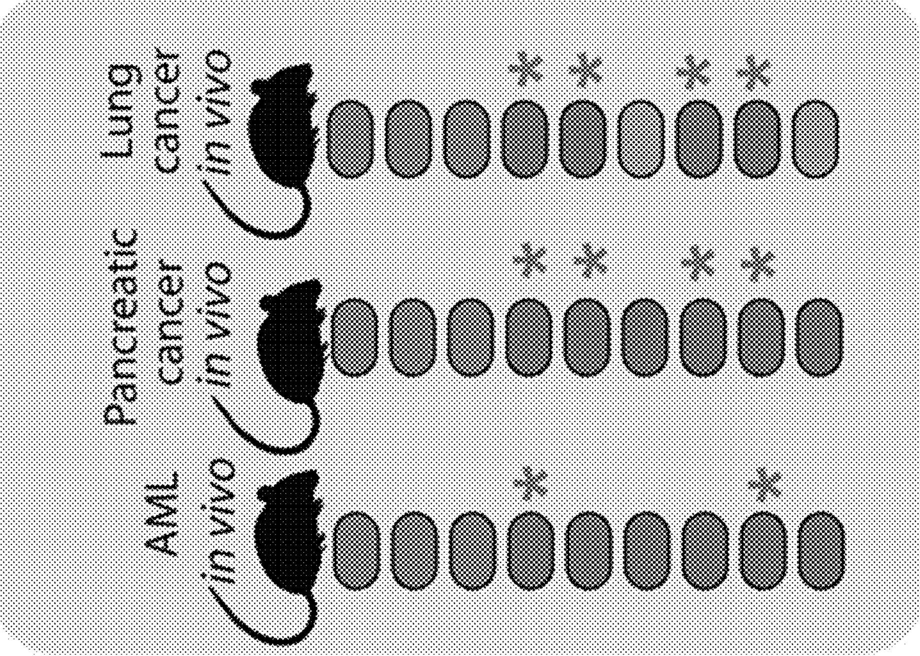
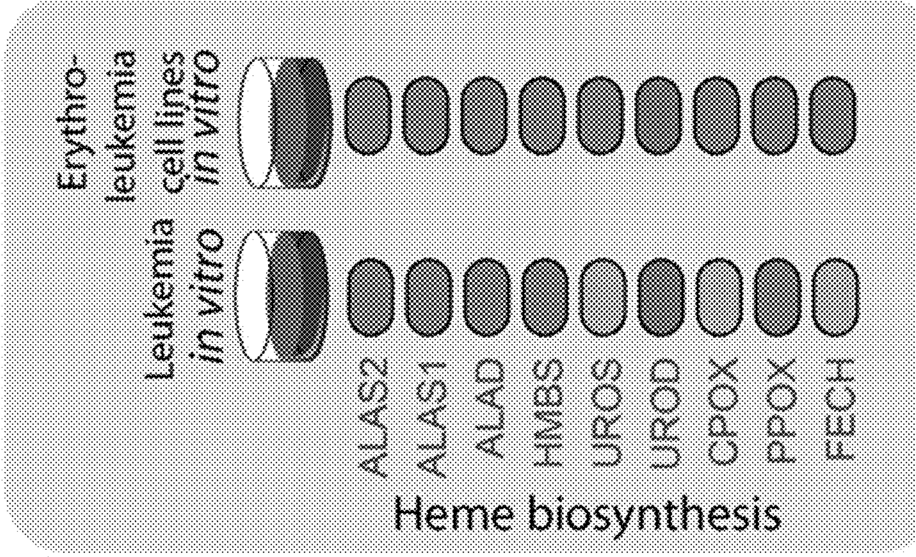
Figure 30

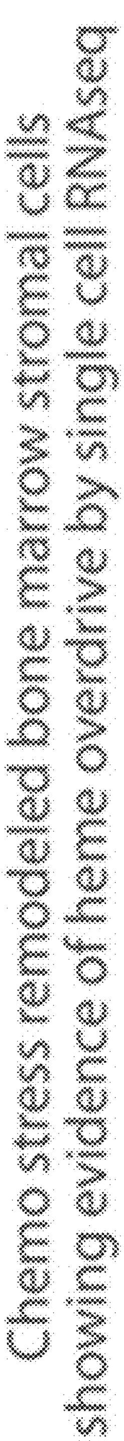
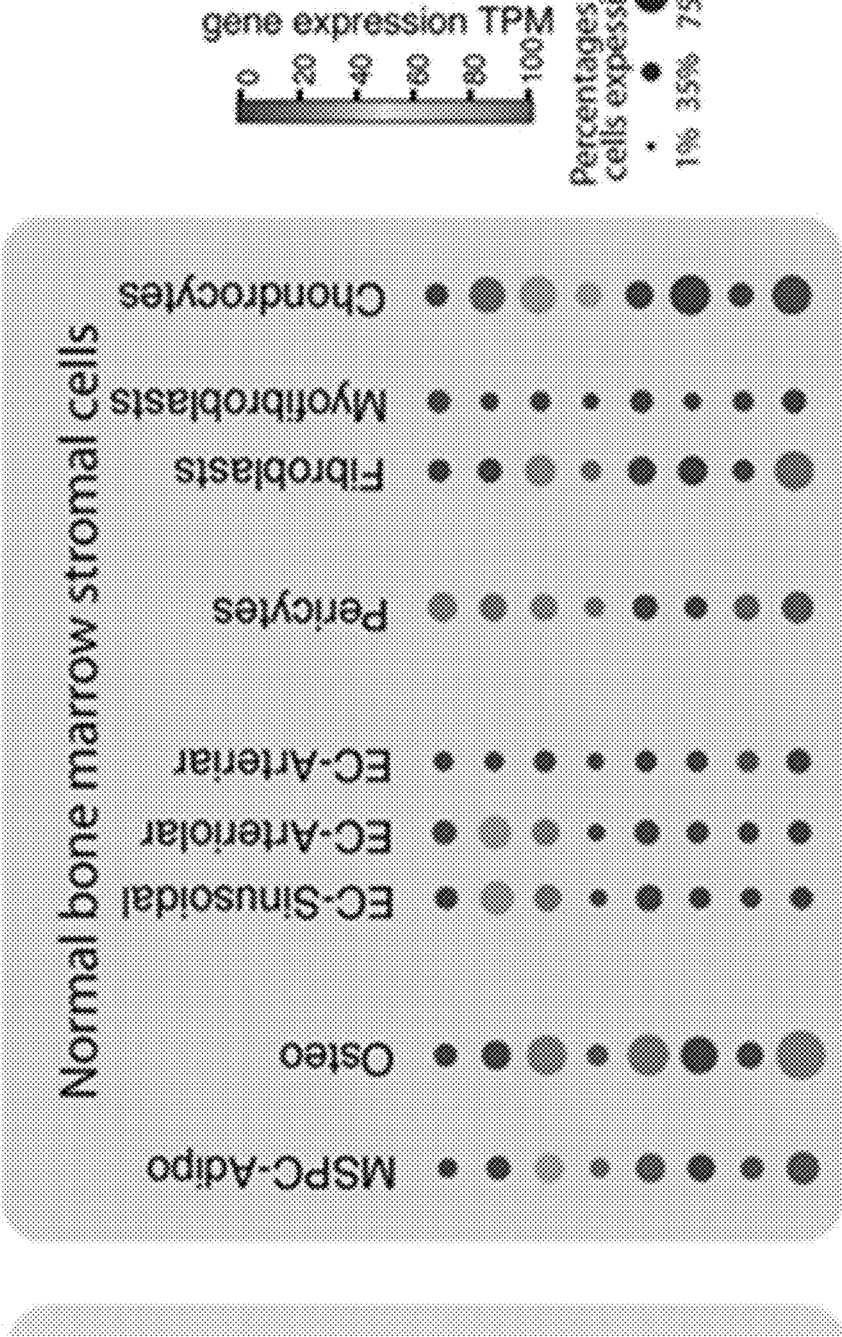
Figure 32

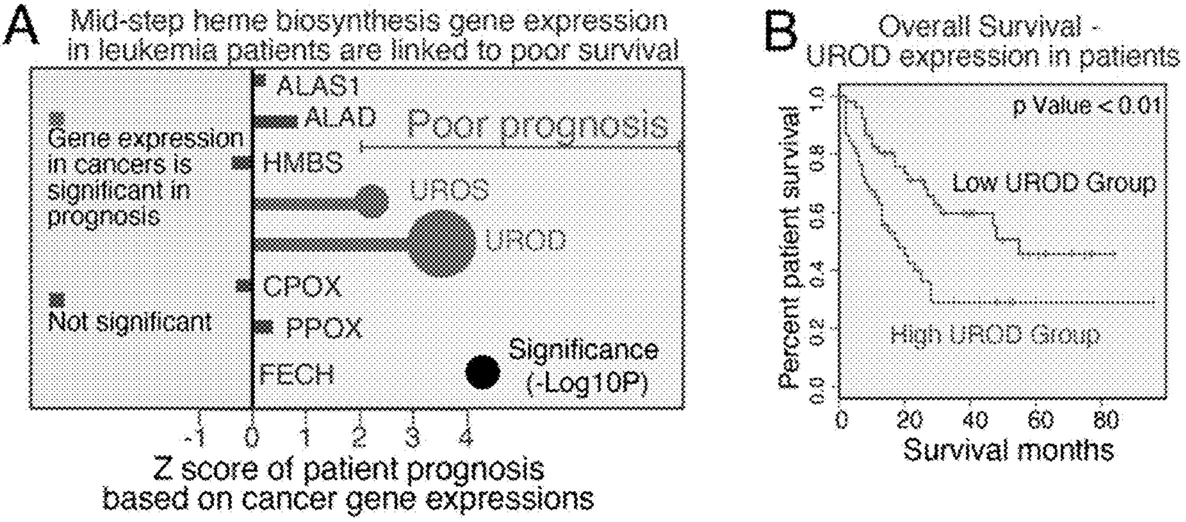
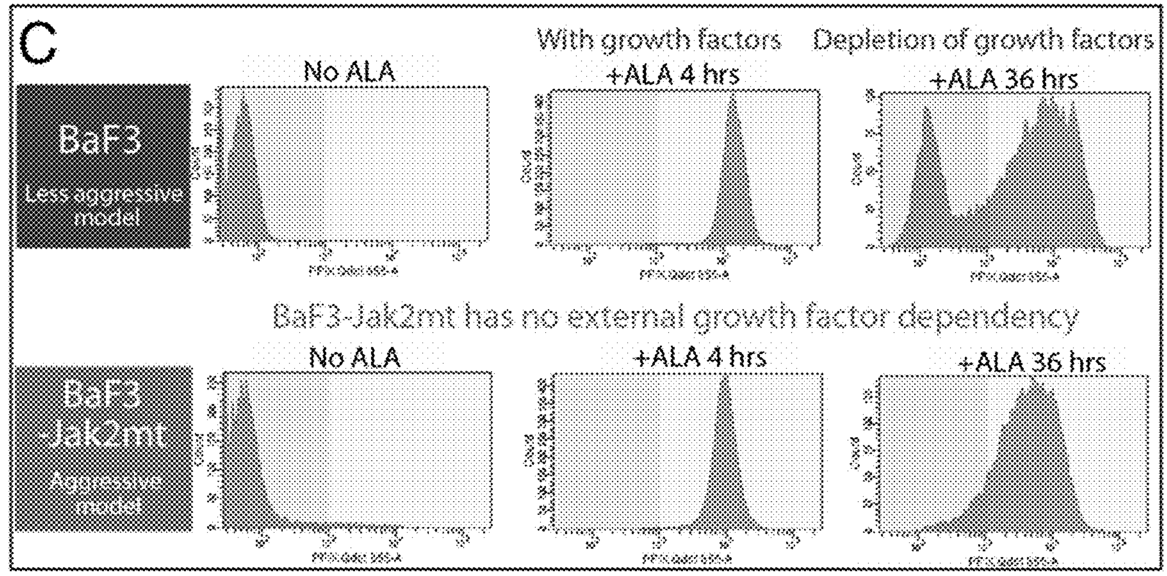
Figure 33A-C

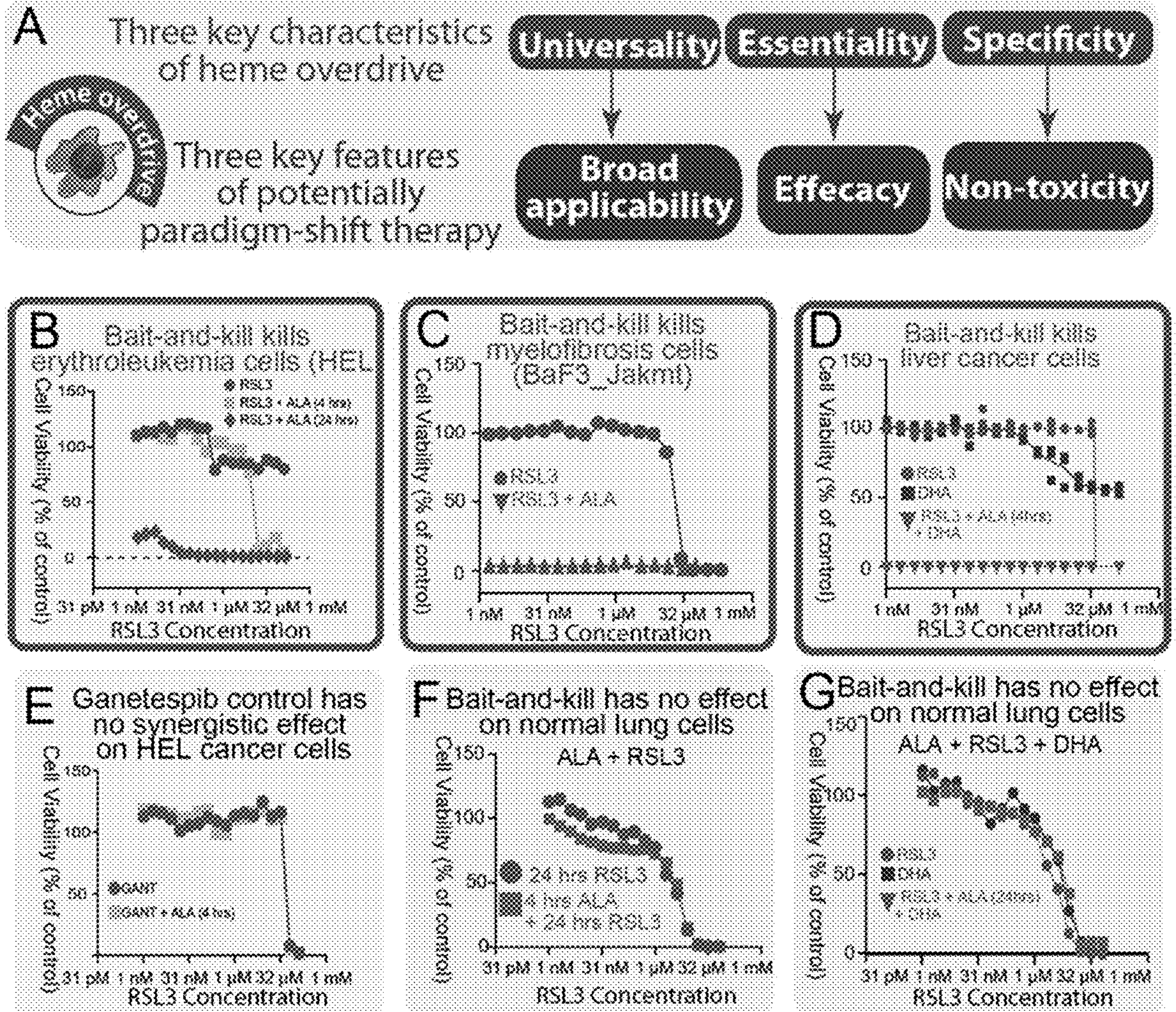
Figure 34A-G

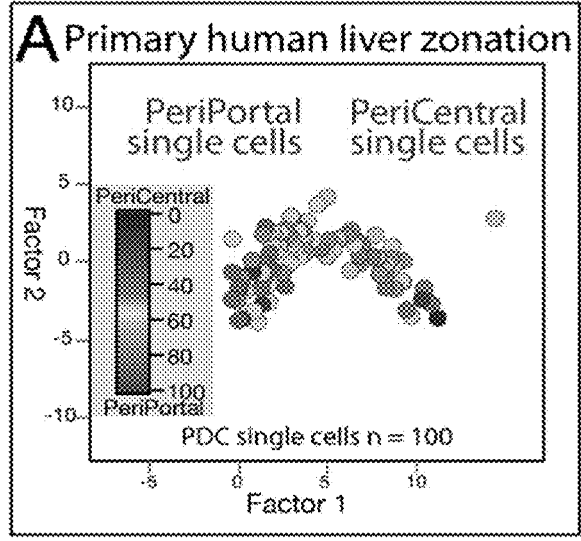
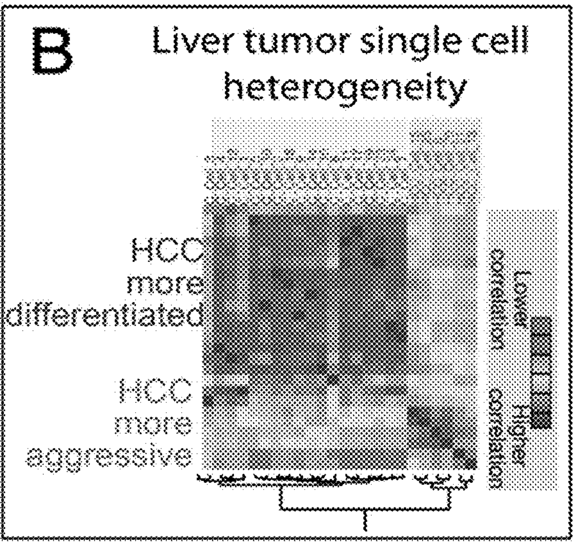
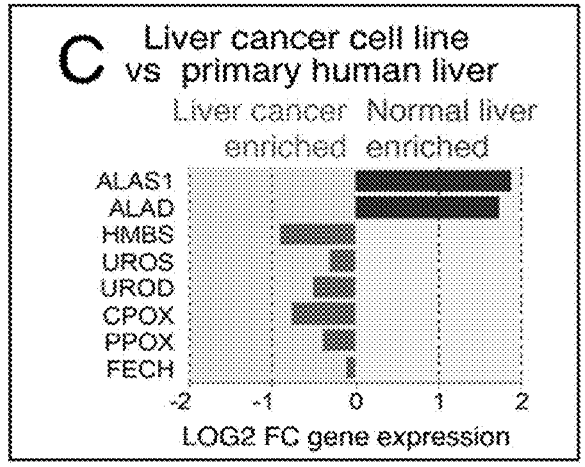
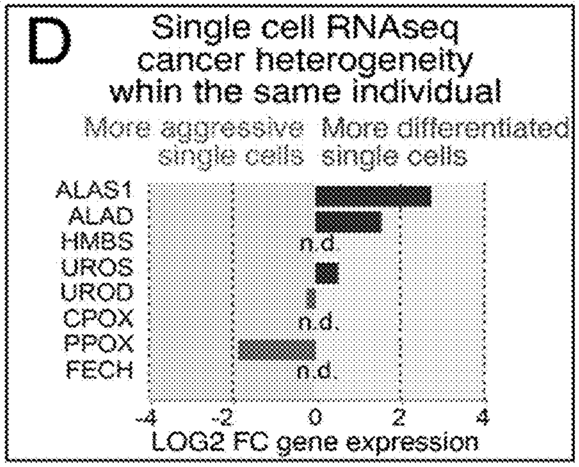
Figure 35A-D

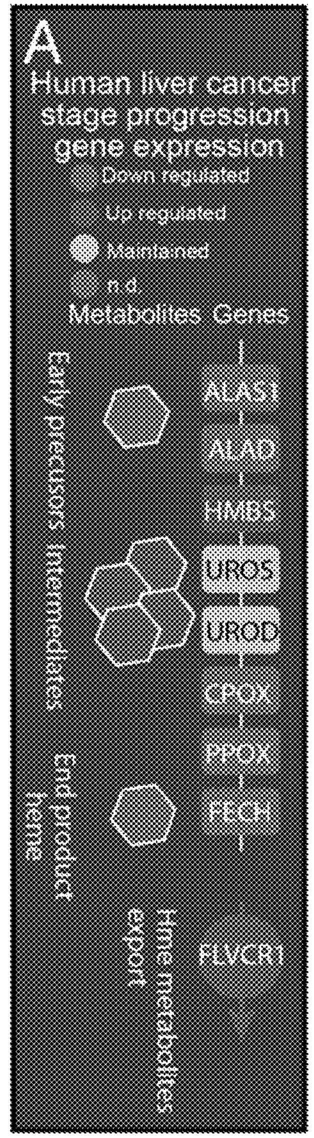
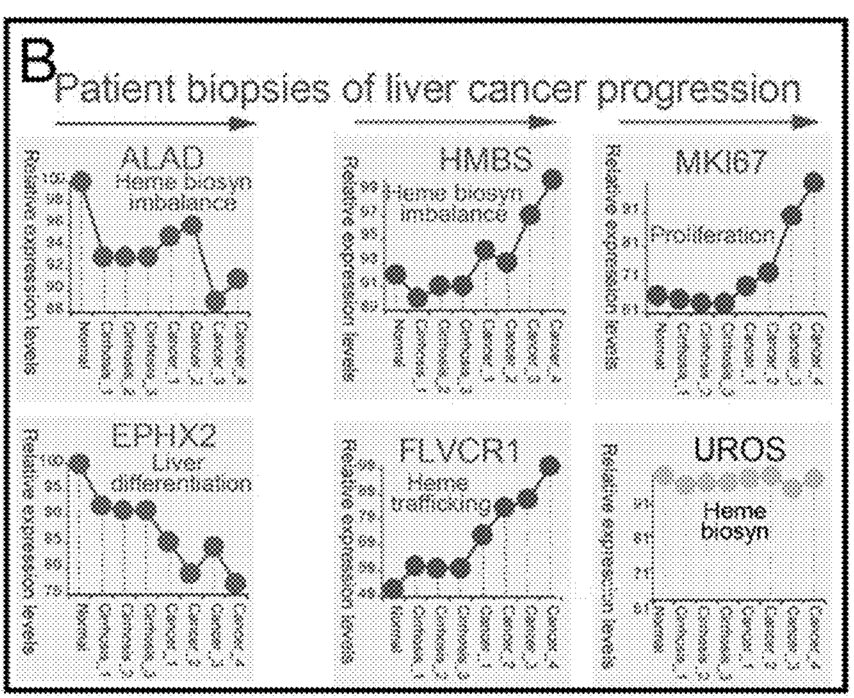
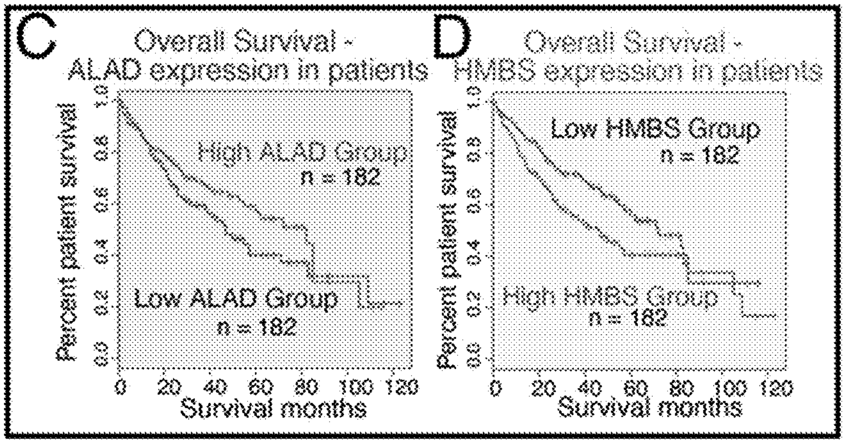
Figure 36A-D

HEME OVERDRIVE REWIRES PAN-CANCER CELL METABOLISM

CROSS REFERENCE TO RELATED APPLICATIONS

This application is a nonprovisional of and claims priority to U.S. Provisional Patent Application Ser. No. 63/269,073, entitled "Heme Overdrive Requires Pan-Cancer Cell Metabolism", filed Mar. 9, 2022, the contents of which are hereby incorporated by reference into this disclosure.

FIELD OF INVENTION

This invention relates to treatment of cancers. More specifically, the present invention provides therapeutic methods and compositions for treating cancer which target heme overdrive.

BACKGROUND OF THE INVENTION

Heme biosynthesis is one of the most efficient metabolic pathways in humans. A total of 270 million molecules of heme are produced for every red blood cell (RBC)[1], at a rate of over 2 million RBCs per second[2]. Heme, a porphyrin ring encaging most of the iron in humans, functions as an essential prosthetic group of numerous proteins with roles ranging from signal sensing, DNA binding, microRNA splicing and processing to enzymatic catalysis[3-21]. To ensure the enormous output of heme biosynthesis, the supply of substrates, intermediates and end-products in the pathway is tightly regulated and precisely balanced[7,22]. Heme is a double-edged sword for cell growth; it is essential in the "right amount"[23] and if not can be toxic[24,25] via unique forms of cell death.

Cancer cells reprogram metabolic pathways to fuel anabolic growth, rapid propagation, and efficient nutrient acquisition[26-28]. Although some studies have implicated heme in carcinogenesis through cytotoxic heme-derived compounds[29,30], lipid peroxidation[31], oxidative damage[32], intestinal flora toxicity[33] and energy production[34], little is known about how heme biosynthesis deregulation and heme trafficking alterations contribute to tumor dependence on heme for survival.

"The Warburg effect"[26,35] and "glutamine addiction"[36,37] are two altered forms of metabolism found in cancer cells. Therapeutic intervention based on these altered cancer metabolic pathways are challenging because glycolysis and glutamine metabolism are required in every cell and thus such therapeutic approaches lead to non-specific toxicity. By contrast, heme overdrive is an ideal cancer metabolic pathway for therapeutic targeting as the inventors have shown that it is: 1) cancer specific (i.e., it is absent in normal cells), 2) universal (i.e., it is present in all cancers), and 3) cancer cell essential (i.e., cancer cells are addicted to it).

Cancers rewire their metabolism to fuel oncogenic growth. Otto Warburg discovered cancer's universal heightened dependence on glycolysis over 100 years ago, yet it is challenging to target the Warburg effect due to its non-specificity and toxicity in normal cells. Similar therapeutic barriers exist in disrupting other non-specific biochemical pathways, such as targeting cancer's glutamine addiction.

End-stage cancers, either when the cancer has overtaken patient's hemopoietic and lymphatic systems, or when the solid tumors have metastasized to distant organs, are responsible for most of the cancer mortalities[166]. Chemo, targeted immune and radiation therapies remain the principal treatments combating cancer[167]. However, these therapies face the challenges of 1) limited efficacy particularly in end-stage cancer, 2) substantial drug-induced toxicity in patients, and/or transient efficacy in only a subset of patients[167].

There are over 100 major types of cancers recognized by National Cancer Institute (cancer.gov), each type constitutes an array of different molecular and histological sub-types, e.g., more than 200 distinct blood cancers are characterized by the current WHO guidelines[168]. Great strides have been made in new diagnosis and treatments, however, tackling diverse cancers effectively remains a major obstacle. Even in resource-rich countries such as the USA, precision oncology approaches collectively benefit less than 10% of all cancer patients[169,170]. An effective cancer therapy that is applicable to a broad range of cancer types does not exist, and yet would be transformative to human health. As such, there is an urgent need to develop broadly applicable, efficacious cancer therapies to improve the health and prevent the loss of life of cancer patients in diverse populations. What is needed is a method of specifically targeting cancer metabolism to better develop cancer therapeutics.

SUMMARY OF THE INVENTION

All cancer cells employ imbalanced and dynamic heme metabolic pathways essential for their oncogenic growth. The inventors have coined the term "heme overdrive" to refer to this phenomenon. Three key characteristics define heme overdrive, i.e., cancer universality, cancer essentiality, and cancer specificity. While heme overdrive is absent in diverse differentiated cells, including hematopoietic stem cells, metabolically active human primary liver cells, and rapidly dividing fibroblasts as well as somatic stem cells, it is present in hundreds of cancers, and is delineated in patient-derived tumor progenitor cells by single cell RNAseq. The only exception to heme overdrive in normal tissues is identified in preimplantation human embryos, where heme overdrive likely links to embryonic omnipotency. Among the major drivers are proteins involved in biosynthesis of heme intermediates (hydroxymethylbilane synthase (HMBS) and uroporphyrinogen decarboxylase (UROD)) and heme trafficking (FLVCR1). CRISPR/Cas9 editing to engineer leukemia cells with impaired heme biosynthesis steps confirmed the whole genomic data analyses that heme overdrive is linked to oncogenic states and cellular differentiation. The inventors developed a novel "bait-and-kill" strategy to target this cancer metabolic vulnerability. This specificity and inducibility of cancer heme overdrive offers elegant therapeutic potential to only kill cancer cells with minimal normal tissue toxicity.

In an embodiment, a method of treating cancer is presented comprising: administering, to the patient, a therapeutically effective amount of a first compound capable of inducing accumulation of heme precursor porphyrin metabolites, such as protoporphyrin IX (PPIX), and subsequently administering a therapeutically effective amount of a second compound capable of inducing cancer cell death.

The concentration of the heme precursor porphyrin metabolites may be at least 100-fold higher as compared to a control before the second compound is administered.

The first compound may be 5-aminolevulinate (ALA). The second compound may be a compound that targets glutathione dependent and independent antioxidant systems. The second compound may be a ferroptosis inducer such as: RSL3, ML210, iFSP1, erastin, artemisinin, chloroquine, dihydroartemisinin, and combinations thereof.

In an embodiment, a method of inducing cancer cell death is presented comprising: administering a therapeutically effective amount of a first compound to induce accumulation of heme precursor porphyrin metabolites, such as protoporphyrin IX (PPIX), and subsequently administering a therapeutically effective amount of a second compound to induce the cancer cell death.

The concentration of the heme precursor porphyrin metabolites may be at least 100-fold higher as compared to a control before the second compound is administered.

The first compound may be 5-aminolevulinate (ALA). The second compound may be a compound that targets glutathione dependent and independent antioxidant systems. The second compound may be a ferroptosis inducer such as: RSL3, ML 210, iFSP1, erastin, artemisinin, chloroquine, dihydroartemisinin, and combinations thereof.

In a further embodiment, a method of treating cancer by activating protoporphyrin IX (PPIX) induced cytotoxicity of cancer cells is presented comprising: administering a first compound, such as 5-aminolevulinate (ALA), capable of inducing PPIX accumulation higher than at least 100-fold concentration as compared to a control to the cancer cells and administering a second compound capable of producing intracellular chemiluminescence or radionuclide generated radiation to the cancer cells.

The second compound may be $^{18}$F-fluorodeoxyglucose ($^{18}$F-FDG), radiolabeled glutamine 4-$^{18}$F-(2S,4R)-fluoroglutamine ($^{18}$F-FGln), luminol, or combinations thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 3 is a table depicting CRISPR/Cas9 essentiality screens related to heme metabolism and oncogenesis.

FIG. 6 is a table depicting CRISPR/CAS9 essentiality scores of diverse cell lines related to heme biosynthesis genes.

FIG. 9A-B are a series of images depicting in vivo CRISPR/Cas9 loss-of-function studies confirm essentiality of cancer heme overdrive. (A) Heme overdrive, resulting from absence of heme metabolism hemostasis, is indicated by the essentiality of the genes for the intermediate enzymatic steps of heme biosynthesis in both murine pancreatic and lung cancer models. The figure shows the comparison of gene essentialities between in vitro and in vivo cancer models, and their statistically significant differences (column 3 of both panels) are indicated with *. The different shades of magenta indicate the different degrees of gene essentiality. The color scheme reflects the pancreatic essentiality in the study. Both in vitro and in vivo essentiality data were retrieved from Zhu et al. The increased gene essentiality, from in vitro to in vivo, of intermediate step of heme biosynthesis genes (HBMS, UROS, CPOX, PPOX) are the only shared metabolic essentiality between pancreatic and lung cancers are indicated with *. The in vitro gene essentiality data indicate that the functional intermediate enzymatic steps in heme biosynthesis are independent of tumor origin or tissue environment (Zhu et al 2021). (B) Analysis of ~2900 metabolic-related genes (retrieved from ref 9) show similar gene essentiality in the in vitro and in vivo settings, indicating that the survival of tumor cells depends on the examined encoded-metabolic enzymes both in vitro and in murine pancreatic and lung cancer models. [No statistically significant essential differences were observed for the essentialities of ALAS1, ALAS2, and FECH, the genes for the first and terminal enzymes of the heme biosynthetic pathway, in either of the in vivo murine cancer models. [adj, adjusted.]

FIG. 10 is a table depicting in vivo murine CRISPR/Cas9 screen gene essentiality scores in pancreatic and lung cancers.

FIG. 11A-C are a series of images depicting analyses of gene expression in tumors of patients with diverse types of cancer support cancer heme overdrive. (A) Up-regulation of gene expression for some enzymes of the heme biosynthetic pathway in ~10,000 patient-derived tumors. ALAS2 is only expressed in myeloid leukemias. (B) The genes for HMBS, the fourth enzyme of the heme biosynthetic pathway, and FLVCR1, the heme exporter, are among the most upregulated in over 80% of all tumors. Oncogenic signaling genes (in blue) AURKA, KRAS and MYC are upregulated in over 90%, 60% and 50% of all tumor types, respectively. Orange shading denotes upregulation of gene expression; blue shading denotes down-regulation of gene expression as compared to normal tissue. The scale of the Y-axis indicates the degree of over- or under-expression. (C) Expression of ALAD, encoding the second enzyme of the heme biosynthetic pathway, is downregulated in tumors, while the gene for the third enzyme of the pathway, HMBS, is overexpressed in most of the tumors. FLVCR1, encoding a heme exporter, is overexpressed in tumors, while HPX, for the heme scavenger hemopexin, is more abundantly expressed in normal tissues. Data are from the GTEx project and TCGA program. FC, fold change; scRNAseq, single-cell RNA sequencing.

FIG. 12 is a table depicting tissue-specific gene expression in patient-derived tumor samples (GTEX project and TGCA program) vs. normal individual samples.

FIG. 13A-F are a series of images depicting heme overdrive is unique to cancer cells and absent in normal cells. (A) Schematic illustrations of the key differences of heme metabolism in cancer vs. normal cells. Red, orange, and yellow shadings represent cancer gene essentiality as in FIG. 1B. Blue colors refer to the normal heme biosynthesis process (B) PPIX autofluorescence (red) is detected in HC-04 liver cancer cells but not in primary human hepatocytes (PHH) following ALA addition, indicating PPIX accumulation in cancer cells but not normal cells. Mitotracker green staining indicates viable cells. Over 1000 cells were assessed for each sample (representative cells shown). PPIX red was not observed in any normal cells. (C) Distinct heme metabolic gene essentiality in stem cells and cancer cells. [Gene essentiality represented as lethality after loss/deletion of a specific gene.] Human primary bone marrow stem cell gene knock down essentiality data are from Egan et al. Cancer CRISPR KO data are from pan-cancer essentiality analysis (Depmap) (D) Validation of K562-FECH KO cell line generated by CRISPR/Cas9 gene editing. Immunoblots of wild-type K562 and K562-FECH KO whole cell lysates show a complete loss of FECH protein in K562-FECH KO cells, with vinculin used as a loading control (top). A 107 bp out of frame CRISPR-induced deletion was identified in the ALAS2 gene (not shown) and due to in inability to identify a specific ALAS2 antibody for immunoblotting, presence of this deletion was confirmed in RT-PCR analysis of K562-ALAS2 KO cells (bottom). (E) Total viable K562 and K562-FECH KO cells (top) and K562 and K562-ALAS2 KO cells (bottom) were determined over time using trypan blue exclusion, and no growth differences were detected. (F) ALAS2 KO K562 cells are arrested in an undifferentiable state. K562 cells readily differentiated upon ROS induction (tert-butyl-hydroperoxide) and are committed into erythroid lineage within 48 hrs, as measured by activation of heme production and benzidine stain as a marker of differentiation. In contrast, ALAS2 KO cells do not respond to the ROS inducer (the first step of differentiation) nor commit to erythroid differentiation.

FIG. 14A-F are a series of images depicting single-cell RNA sequencing of human AML bone marrow samples supports heme overdrive as a hallmark of cancer cells. Single-cell transcriptomes were obtained from bone marrow biopsies of AML donors with over 60% blasts. (A) Single-cell population composition shows only a minor fraction of the cells are cancer progenitors, which are defined by transcriptome embedding and clustering analysis. (B) Identification of distinct single cell populations in the AML patient bone marrow samples by t-SNE (t-distributed Stochastic Neighbor Embedding) analysis. A total of 1349 high-quality transcriptomes from patient biopsies were used. (C) Representative genes for proteins associated with heme metabolism, normal early erythroid development, cell proliferation and erythroid commitment process are plotted. (D) UROD, the gene encoding the fifth enzyme of the heme biosynthetic pathway, is highly expressed in cancer early progenitors. HMS and UROS, which encode other intermediate step-catalyzing enzymes, are also over expressed in cancer progenitors. (E) Marker genes delineate cell populations from the patient samples. Note the complementary expression patterns of ALAS1 vs. ALAS2. (F) Solid tumor single cell RNAseq shows overexpression of the genes for the enzymes responsible for the intermediate heme biosynthetic pathway steps in breast cancer and melanoma.

FIG. 14G is an image depicting single-cell RNA sequencing of human AML bone marrow samples supports heme overdrive as a hallmark of cancer cells. Intermediate step enzyme genes are highly expressed in AML (upper). Intermediate step enzyme genes are highly expressed in pancreatic cancer by single-cell RNAseq (lower).

FIG. 15A-C are a series of images depicting cancer progenitor cells highly express cell niche interaction genes and show features of highly dynamic metabolic substrate trafficking hubs. (A) AML progenitor cells specifically express genes for interacting proteins (“interactors”) within the erythroblastic island, the specialized bone marrow niche where erythroid precursors proliferate, differentiate, and enucleate. The Y-axis indicates the $\log_2$-fold change of gene expression levels in early AML progenitor cells relative to other progenitor cells. Positive $\log_2$-fold change values indicate increased expression levels over those of the control, while negative values indicated decreased expression relatives relative to those of the control. Names of selected genes are indicated in the X-axis. FC: Fold change. (B) AML progenitor cells show hallmarks of metabolic substrate trafficking and abundant salvaging pathways. Genes associated with endocytosis, lipid transport, NAD salvage, nucleotide salvage are upregulated, while genes related to cell morphology and barrier formation are downregulated. (C) The cancer cell niche is inferred to present elevated gene expression for proteins involved in intracellular surface molecular interactions (e.g., VCAM1-ITGA4 and ITGAX/ITGB2-ICAM4). The schematic represents a reconstruction of a cancer partner cell-cancer progenitor cell interaction based on previously established molecular interactions (Socolovsky 2013).

FIG. 16A-B are a series of images depicting AML patient cancer progenitor cells show enhanced metabolic flux. (A) The cancer early progenitor cells represent only 2% of the AML patient sample cell population (see FIG. 3). Light blue shading represents down-regulated genes and light pink shading indicates upregulated genes. The $-\log_{10}$ (p values) in the Volcano plot represent the level of significance of each gene, while the $\log_2$-fold change values represent the difference between the levels of expression for each gene between the AML progenitor cells and other populations of cells. The genes related to metabolic flux are highlighted in yellow and include genes associated with the postulated heme overdrive, lipid import and macromolecule salvage. The canonical erythropoiesis master transcription regulators are colored as early (blue dots) and late (pink dots) stages based on their gene expression sequence during erythropoiesis. (B) The cancer progenitor specific gene expressions of APOC1 and S100A6 are shown in different cell populations. FPKM, fragments per kilobase million.

FIG. 17A-D are a series of images depicting Targeting heme overdrive in cancer cells with a bait-and-kill strategy. (A) The concentration of PPIX accumulated in K562 cells depends on the ALA concentration supplemented to the culture medium. K562 cells were cultured in the absence or presence of 100 mM glycine or ALA (0.1 mM, 0.25 mM, 0.5 mM, and 1.0 mM) at 37° C. for 24 h, and PPIX fluorescence was measured by flow cytometry. [a.u., arbitrary units](B) ALA-induced PPIX accumulation in HEL cells. PPIX accumulated in 100% of the HEL cells (n>10,000 cells) as detected by PPIX fluorescence 4 hours after treatment with 1.0 mM ALA. The red sectors of the pie chart above the graph bars indicate the percentage of PPIX-accumulating HEL cells, while those in blue indicate the percentage of cells with no accumulated PPIX. The normalized PPIX values (%) indicated on the pie charts were obtained by dividing the PPIX fluorescence by the PPIX fluorescence intensity value for HEL cells incubated in 1.0 mM ALA-containing medium for 4 h, which was arbitrarily assigned 100%. (C) Cell viability is unaffected using ALA (“bait”) as inducer of PPIX accumulation. HEL cells were cultured in the absence or presence of ALA (1 mM) or ALA (1 mM) and DMSO (0.1%) at 37° C. for 24 h, and their viability was calculated from the generated luminescence upon reaction with CellTiter-Glo. The assays were conducted in triplicate. [RLU, relative luminescence units]. (D) Dose-dependent response of HEL cell viability for cells treated with increasing concentrations of RSL3 (Top plot) or ganetespib (Bottom plot). Cell viability was determined following incubation with a wide concentration range of RSL3 (top plot) or ganetespib (GANT) (bottom plot) either in the absence or presence of ALA (1.0 mM) for 4 or 24 h. [Note that the concentration of either RSL3 or ganetespib spans a range from pM to 150 mM.]

FIG. 18A-C are a series of images depicting bait-and-kill has no synergistic cytotoxic effect on normal cells. A. The bait-and-kill strategy involving prior treatment of the cells with ALA significantly enhances the sensitivity of cancer cells to RSL3 compared to control cells. Similar results observed in all cells tested. Control normal human cells are primary human lung fibroblasts that showed no ALA-induced PPIX accumulation in >99% of the cells. B and C. There is no synergistic killing effect upon treatment of primary human lung fibroblasts with RSL3 for either 24 hours (panel B) or 48 hours (panel C). This contrasts to the pMol range for the IC50 values of RSL3 in cancer cells in FIG. 17. Both primary human lung fibroblast growth and proliferation are unaffected with 1 μM RSL3.

FIG. 22A-E are a series of images depicting heme overdrive operates in human lung cancers. A. Schematic illustration of the overall objectives (i.e. targeting cancer heme overdrive with non-toxic therapy development), and definitions of cancer heme overdrive. Heme homeostasis refers to the heme biosynthetic pathway in normal cells. Heme overdrive refers to the imbalanced (i.e., with aberrantly increased and suppressed enzymatic and transport/trafficking activities) pathway in cancer cells. Activities in heme overdrive are indicated by the different size of the product pools (red circle sizes). B. Schematic representation of heme overdrive in lung cancer as inferred from analyses of gene expression in tissues of a lung cancer patient, single cell RNAseq and CRISPR loss-of-function screens. A partial heme biosynthetic pathway (4 of the 8 enzymes), its penultimate intermediate, protoporphyrin (PPIX), and final product, heme, are indicated. C. Heme overdrive is absent in primary human lung fibroblasts. Accumulation of PPIX, which fluoresces red, is not detected (panel on the right). D. Heme overdrive is present in cancer cells. PPIX autofluorescence (red) is detected in HC-04 liver cancer cells but not in primary human hepatocytes (PHH) following ALA addition, indicating PPIX accumulation in cancer cells but not normal cells. Mitotracker green staining indicates viable cells. Over 1000 cells were assessed for each sample (representative cells shown). PPIX red was not detected in normal cells. E. Gene expression patterns from 969 lung cancer patients indicate imbalanced heme biosynthetic pathway and enhanced heme trafficking. Lung epithelial cell differentiation and cell proliferation related genes are plotted as controls. [Abbreviations: ALAS1, 5-aminolevulinate synthase 1; ALAD, ALA dehydratase (aka porphobilinogen synthase); HMBS, hydroxymethylbilane synthase; UROS, uroporphyrinogen III synthase; FLVCR, feline leukemia virus subgroup C receptor family. LUAD, lung adenocarcinoma; LUSC, lung squamous cell carcinoma.]

FIG. 27A-B are a series of images depicting primary CAFs show heme overdrive. A. The primary tumor is primary lung adenocarcinoma (female 55 years. TNM Staging: T26NOM0). The samples were from surgically excised samples, and the cancer-associated cells were isolated (BioIVT). Vimentin (IHC) >95%. ALA (1 mM final concentration) was added at least 4 hours prior to flowcytometry and PPIX quantification. Normalized CAFs, after 15 in vitro passages from the same lung cancer patient, maintained rigorous cell growth and cell division but lost heme overdrive (right panel). Heme overdrive, as estimated from PPIX accumulation, is present in over 99% of CAFs from primary lung adenocarcinoma (left panel). Even without ALA induction, PPIX accumulates in 24% of the CAFs (middle panel). B. Primary CAFs, onco-transformed fibroblasts and cancer cells show similar patterns of ALA induced PPIX.

FIG. 28A-D are a series of images depicting lung cancer heme overdrive is supported by both bulk and single cell RNAseq and is linked to the overall survival (OS) of patients. A and B. Patient tumor tissue RNAseq and single cell lung cancer RNAseq support heme overdrive. Genome analysis (shown in A.) was based on lung cancer data publicly available at The Cancer Genome Atlas (TGCA) and Genotype-Tissue Expression (GTEx) program. The single cell expression data from Zilionis et al. were used to study the expression differences in more aggressive vs. more differentiated lung cancer cell populations within the same tumor. C and D. Heme overdrive in lung cancer is related to the patients OS. The Kaplan-Meier estimator, a non-parametric statistic, was used to estimate the survival function from the lifetime data, and the generated Kaplan Meier curves were used for visual representation. Shown are the Kaplan-Meier curves for data of visualization of ALAD (panel C) and HMBS expression (panel D) in lung cancer patients. The expression data were from TCGA and were analyzed in relation to the OS of the respective patients (panels C and D). Expression of ALAD and HMBS (the genes for the second and third enzymes of the heme biosynthetic pathway, respectively) show contrasting prognostic results in patients OS, indicating that the greater the extent of heme overdrive (i.e., the larger the difference between ALAD and HMBS expression), the more aggressive the lung cancer is. The statistical difference between the groups is estimated by the log-rank test [FC, fold-change.]

FIG. 29A-B is a series of images depicting imbalanced heme biosynthesis/heme overdrive operates in diverse blood cancers. A. Cancer heme overdrive operates in major lineages of blood cancers. Rare blood cancers pertinent in the preliminary results are indicated in red. B. Cancer cells have imbalanced heme biosynthesis, leading to accumulation of heme intermediates. The 'severed' cancer heme biosynthesis pathway is contrasted with the complete biosynthesis in normal cells. HMBS, UROS, UROD, CPOX and PPOX: genes encoding 5 of the 8 heme biosynthesis enzymes that are essential for cancer survival.

FIG. 30 is an image depicting in vivo CRISPR/Cas9 loss-of-function studies confirm essentiality of cancer heme overdrive. Heme overdrive is indicated by the essentiality of the genes for the intermediate enzymatic steps of heme biosynthesis in murine, AML, pancreatic and lung cancer models. The increased essentialities of the genes for the enzymes governing the intermediate steps of heme biosynthesis (HBMS and PPOX) are the only shared metabolic essentialities between cancers in vivo. Note that, the increased essentiality of heme intermediate synthesis gene is exceptional, because analysis of ~2900 metabolic-related genes show similar gene essentiality in the in vitro and in vivo settings in solid tumors.

FIG. 32 is an image depicting primary TME cells show heme overdrive. Single cell transcriptomes of bone marrow niches show evidence of heme overdrive only in cells subjected to acute chemo stress.

FIG. 33A-C are a series of images depicting leukemia cancer heme overdrive is linked to patient overall survival (OS). A. Blood cancer progression transcriptome data indicates mid-step gene poor-prognosis. B. Heme overdrive relates to OS in leukemia patients. The Kaplan-Meier estimator was used on the lifetime data (from TCGA). UROD overexpression shows poor OS. C. Experimental validation of blood cancer aggressiveness linked to heme overdrive. Upon growth factor withdraw at 36 hrs, the less-aggressive cell line BaF3 reduces PPIX accumulation.

FIG. 34A-G are a series of images depicting targeting heme overdrive with Bait-and-Kill. A. Three key features of heme overdrive enables designing of potentially paradigm-shifting therapies. B-D, RSL3 after ALA treatment killed most cancer cells even at the lowest concentration. DHA: artemisinin E. No sensitizing effect was found for cells treated with Ganetespib. F-G. There is no synergistic effect of primary human lung fibroblasts.

FIG. 35A-D are a series of images depicting whole tumor and single cell transcriptome studies support heme overdrive in liver cancers. A. Healthy donor liver scRNAseq performed at USF. The inventors obtained >10,000 transcriptomes with 10× genomics. Liver zonation are found with most differentially expressed genes after data dimension al reduction with t-SNE. B. Single cell HCC analysis show cancer cells heterogeneity. C. Whole tumor D. Single cell, transcriptome data show evidence of heme overdrive.

FIG. 36A-D are a series of images depicting liver cancer heme overdrive is linked to patient overall survival (OS). A and B. Liver cancer progression transcriptome data support heme overdrive. C and D. Heme overdrive relates to OS. The Kaplan-Meier estimator was used on the lifetime data (from TCGA). The greater the extent of heme overdrive (i.e., the larger the difference between ALAD and HMBS expression), the more aggressive the liver cancer is.

DETAILED DESCRIPTION OF THE PREFERRED EMBODIMENT

Figure 1:
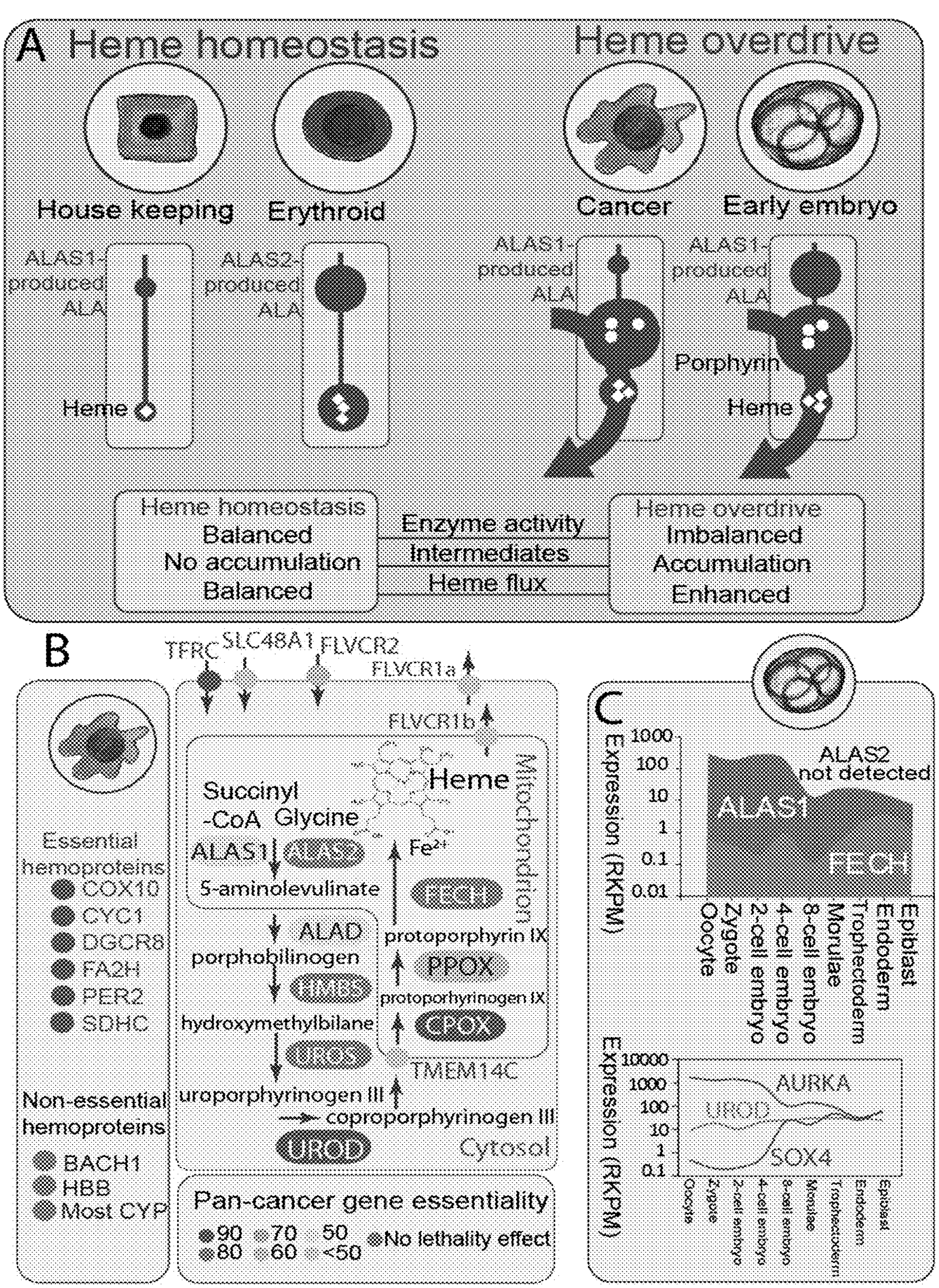
FIG. 1A-C are a series of images defining heme overdrive with CRISPR data and early human embryonic stem cell single cell RNAseq. (A) Schematic illustration of heme homeostasis and heme overdrive. Heme homeostasis refers to the heme biosynthetic pathway in normal cells, with the housekeeping enzyme ALAS1 catalyzing the first and rate-limiting step in all cells, except precursor erythroid cells, where the erythroid-specific ALAS isozyme ALAS2 catalyzes the rate-determining step. Heme overdrive refers to the imbalanced (i.e., with aberrantly increased and suppressed enzyme activities) pathway in cancer cells and early human embryonic stem cells, with the ALAS1 isozyme controlling ALA production regardless of the cell type. White circles and white diamonds represent porphyrin intermediates and heme, respectively; Erythroid refers to erythroid precursor cell. Imbalanced enzyme activities in heme overdrive are indicated by different size of product pools (dark red circle sizes). ALA, 5-aminolevulinate; ALAS, ALA synthase. (B) Defining heme overdrive with CRISPR KO-derived essentiality data in over 300 cancer cell lines. Analysis of CRISPR essentiality data enables mapping of heme overdrive in 27 major types of cancer. Color mapping indicates average cancer cell growth dependence revealed by CRISPR KO of a given gene. UROD has the highest pan-cancer essentiality. (C) Early human embryonic stem cells show features of heme overdrive. The expression levels for ALAS1 and FECH differ over 100-fold during the first rounds of embryonic stem cell divisions, but they normalize with the early embryonic development progression. AURKA and SOX4 show expected patterns of expression dynamics during embryogenesis. [Abbreviations: ALA, 5-aminolevulinate; ALAS1, housekeeping ALA synthase; ALAS2, erythroid-specific ALA synthase; ALAD, ALA dehydratase (aka porphobilinogen synthase); BACH, transcription regulator BACH (BTB and CNC homology); CPOX, coproporphyrinogen oxidase; COX10, cytochrome C oxidase assembly homolog 10; CYC1, cytochrome C1; CYP, cytochrome P450 family; DGCR8, DGCR8 microprocessor complex subunit; FAH2, fatty acid 2-hydroxylase 2; FECH, ferrochelatase; FLVCR, feline leukemia virus subgroup C receptor family; FLVCR1a, FLVCR member 1a; FLVCR1b, FLVCR member 1b; FLVCR2, FLVCR member 2; HBB, hemoglobin β-subunit; HMBS, hydroxymethylbilane synthase; PER2, period circadian regulator 2; PPOX, protoporphyrinogen oxidase; RKPM, reads per kilobase million; SDHC, succinate dehydrogenase complex subunit C; TFRC, transferrin receptor; TMEM14C, transmembrane protein 14C; UROD, uroporphyrinogen decarboxylase; UROS, uroporphyrinogen III synthase].

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention. The following description is not intended to limit the scope of the present description disclosed herein.

Abbreviations

ALA, 5-aminolevulinate;
ALAS1, housekeeping ALA synthase;
ALAS2, erythroid-specific ALA synthase;
ALAD, ALA dehydratase (aka porphobilinogen synthase);
AURKA, Aurora kinase A;
AURKB, Aurora kinase B;
BACH, transcription regulator BACH (BTB and CNC homology);
CPOX, coproporphyrinogen oxidase;
COX10, cytochrome C oxidase assembly homolog 10;
CYC1, cytochrome C1;
CYP, cytochrome P450 family;
DGCR8, DGCR8 microprocessor complex subunit;
FAH2, fatty acid 2-hydroxylase 2;
FECH, ferrochelatase;
FLVCR, feline leukemia virus subgroup C receptor family;
FLVCR1a, FLVCR member 1a;
FLVCR1b, FLVCR member 1b;
FLVCR2, FLVCR member 2;
HBB, hemoglobin β-subunit;
HMBS, hydroxymethylbilane synthase;
HMOX1, heme oxygenase 1;
HPX, hemopexin;
PER2, period circadian regulator 2;
PPOX, protoporphyrinogen oxidase;
RKPM, reads per kilobase million;
SDHC, succinate dehydrogenase complex subunit C;
TFRC, transferrin receptor;
TMEM14C, transmembrane protein 14C;
UROD, uroporphyrinogen decarboxylase;
UROS, uroporphyrinogen III synthase Definitions Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

All numerical designations, such as pH, temperature, time, concentration, and molecular weight, including ranges, are approximations which are varied up or down by increments of 1.0, 0.1, 0.01, or 0.001 as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

"Optional" or "optionally" means that the subsequently described event or circumstance may or may not occur, and that the description includes instances where said event or circumstance occurs and instances where it does not.

As used in the specification and claims, the singular form "a", "an" and "the" include plural references unless the context clearly dictates otherwise. For example, the term "a vector" includes a plurality of vectors.

As used in this specification and the appended claims, the term "or" is generally employed in its sense including "and/or" unless the context clearly dictates otherwise.

As used herein, "about" means approximately or nearly and in the context of a numerical value or range set forth means ±15% of the numerical.

As used herein "patient" is used to describe an animal, preferably a human, to whom treatment is administered, including prophylactic treatment with the compositions of the present invention.

As used herein "animal" means a multicellular, eukaryotic organism classified in the kingdom Animalia or Metazoa. The term includes, but is not limited to, mammals. Non-limiting examples include humans, rodents, mammals, aquatic mammals, domestic animals such as dogs and cats, farm animals such as sheep, pigs, cows and horses. Wherein the terms "animal" or the plural "animals" are used, it is contemplated that it also applies to any animals.

The terms "risk or susceptibility" as used herein refers to the determination as to whether a subject would or would not respond to a particular therapy or would or would not develop a particular disease or symptom.

The term "normal" as used herein refers to a sample or patient which are assessed as not having cancer.

"Sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof.

"Tissue sample" or "cell sample" means a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. For instance, a "tumor sample" is a tissue sample obtained from a tumor or other cancerous tissue. The tissue sample may contain a mixed population of cell types (e.g., tumor cells and non-tumor cells, cancerous cells and non-cancerous cells). The tissue sample may contain compounds which are not naturally intermixed with the tissue in nature such as preservatives, anticoagulants, buffers, fixatives, nutrients, antibiotics, or the like.

The term "cell" or "cells" is used synonymously herein and refers to in vitro cultures of mammalian cells grown and maintained as known in the art, as well as biological samples obtained from tumor specimens or normal specimens in vivo.

A "tumor cell" as used herein, refers to any tumor cell present in a tumor or a sample thereof. Tumor cells may be distinguished from other cells that may be present in a tumor sample, for example, stromal cells and tumor-infiltrating immune cells, using methods known in the art and/or described herein.

A "reference sample," "reference cell," "reference tissue," "control sample," "control cell," or "control tissue," as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, the reference sample, reference cell, reference tissue, control sample, control cell, or control tissue may be healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

The term "expression profile" as used herein refers to a genomic expression profile, for example an expression profile of microRNAs or proteins. The profiles may be generated by any means for determining a level of a nucleic acid sequence, e.g. quantitative hybridization of microRNA, labeled microRNA, amplified microRNA, cDNA, quantitative PCR, ELISA for quantitation, etc. For proteins, the profiles may be generated by any means for determining a level of a protein, e.g. Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners. The profile must allow for the analysis of differential gene expression between two samples.

The terms "overexpression" and "underexpression" as used herein refers to the expression of a gene of a patient at a greater or lesser level, respectively, than the normal or control expression of the gene, as measured by gene expression product expression such as mRNA or protein expression, in a sample that is greater than the standard of error of the assay used to assess the expression. A "significant" expression level may be a level which either meets or is above or below a predetermined score for a gene.

The term "compound" as used herein refers to a chemical formulation, either organic or inorganic, that induces a desired pharmacological and/or physiological effect on a subject when administered in a therapeutically effective amount. "Compound" is used interchangeably herein with "drug" and "therapeutic agent".

"Administration" or "administering" is used to describe the process in which compounds of the present invention, alone or in combination with other compounds, are delivered to a patient. The composition may be administered in various ways including, but not limited to, oral; parenteral; intrathecal; intramuscular; subcutaneous; etc. Each of these conditions may be readily treated using other administration routes of compounds of the present invention to treat a disease such as cancer.

"Parenteral administration" as used herein refers to modes of administration other than enteral and topical administration, usually by injection, and includes, but is not limited to, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

"Treatment" or "treating" as used herein refers to any of: the alleviation, amelioration, elimination and/or stabilization of a symptom, as well as delay in progression of a symptom of a particular disorder. For example, "treatment" of cancer may include any one or more of the following: amelioration and/or elimination of one or more symptoms associated with the cancer, reduction of one or more symptoms of the cancer, stabilization of symptoms of the cancer, and delay in progression of one or more symptoms of the cancer.

"Prevention" or "preventing" as used herein refers to any of: halting the effects of the cancer, reducing the effects of the cancer, reducing the incidence of the cancer, reducing the development of the cancer, delaying the onset of symptoms of the cancer, increasing the time to onset of symptoms of the cancer, and reducing the risk of development of the cancer.

The term "prognosis" refers to the determination or prediction of the course of disease or condition or to monitoring disease progression or regression from one biological state to another. Prognosis can include the determination of the time course of a disease, with or without treatment. Where treatment is included, the prognosis includes determining the efficacy of the treatment for the disease or condition.

"Ferroptosis" as used herein refers to an iron-dependent, oxidative cell death that is characterized by iron-dependent accumulation of reactive oxygen species (ROS) within the cell.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, $19^{th}$ ed.) describes formulations which can be used in connection with the subject invention.

For ease of administration, the subject compounds may be formulated into various pharmaceutical forms. As appropriate compositions there may be cited all compositions usually employed for systemically or topically administering drugs. To prepare the pharmaceutical compositions of this invention, the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment.

As used herein, the term "therapeutically effective amount" refers to that amount of a therapy (e.g., a therapeutic agent or vector) sufficient to result in the amelioration of cancer or one or more symptoms thereof, prevent advancement of cancer, or cause regression of cancer. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. The compositions used in the present invention may be administered individually, or in combination with or concurrently with one or more other therapeutics for cancer.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequently. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The term "cancer", "tumor", "cancerous", and malignant" as used herein, refer to the physiological condition in mammals that is typically characterized by unregulated cell growth. Since heme overdrive occurs in all cancers, treatment of all cancers by targeting the intermediates in the heme pathway is contemplated. Non-limiting examples of a cancer that can be treated with the intended use described herein include, but are not limited to, the following: pancreatic cancer such as, but not limited to, insulinoma, gastrinoma, glucagonoma, vipoma, somatostatin-secreting tumor, and carcinoid or islet cell tumor; leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's lymphoma, non-Hodgkin's lymphoma; multiple myelomas such as but not limited to smoldering multiple myeloma, nonsecretory myeloma, osteosclerotic myeloma, placancer cell leukemia, solitary placancercytoma and extramedullary placancercytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; glial brain tumors (i.e., gliomas) such as but not limited to, astrocytoma, ependymoma, oligodendroglioma, brain stem glioma, optic glioma, diffuse intrinsic pontine glioma, mixed glioma (i.e., oligoastrocytoma), glioblastoma, glioblastoma multiforme, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancercytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine,* 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

"Heme overdrive" as used herein refers to the mechanism in which cancer cells reprogram metabolism which is characterized by imbalanced and dynamic heme metabolic pathways essential for cancer cell growth. Specifically, cancer cells employ and depend on imbalanced dynamic heme metabolic pathways for oncogenic growth. Heme overdrive is absent in differentiated cells or somatic stem cells but is present in patient-derived tumor progenitor cells and in early embryogenesis. The major drivers are proteins involved in biosynthesis of heme intermediates and heme trafficking.

For over a century, the association between photosensitizing porphyrins and cancer has been recognized[84], and the preferential porphyrin accumulation in cancer cells has been used in the development of light-based therapies as early as 1911[85]. The results show that heme overdrive, characterized by an imbalanced and dynamic porphyrin production, is ubiquitous to cancer cells and provide the likely cellular basis for specific light-based therapies. With a new understanding of this aberrant metabolic pathway in cancer, heme overdrive may offer novel vulnerabilities and opportunities for cancer therapeutic intervention.

Cancer metabolic processes are often described in terms of aberrant gene regulation and epigenomic reconfiguration[86-88]. Heme overdrive likely operates through direct epigenetic regulation[89] with heme/porphyrin acting as a master regulator of chromatin, such as via binding to guanine quadruplex (G4) DNA structures[51]. Heme, a recognized molecular sensor[15], contributes—perhaps via a paracrine/autocrine mechanism,—to the regulation of genes associated with biological processes as diverse as angiogenesis, oxidative stress management, circadian rhythm adjustment[90], and anabolism[15]. Clearly, this recognition of heme as a signaling molecule has bolstered the understanding of the multifaceted roles of heme in cancer pathogenesis[91,92]. The findings provide a new line of evidence for the signaling power of heme/porphyrin, particularly in relation to cellular redox stress and growth.

Cancer cells often employ bio-energetically favorable mechanisms to fuel anabolism and growth[78]. For rapidly dividing cancer cells, this means a heavy reliance on utilization of salvage and scavenging[93] pathways to provide structural and energetic metabolic intermediates to fuel unchecked proliferation[78]. With the analysis of the data on human AML single-cell transcriptomes, the inventors found that cancer progenitor cells preferably express genes for enzymes involved in salvaging pathways for biomolecules such as NAD, purines, and pyrimidines. Interestingly, the genes SLC28A3 and SLC29A3, encoding nucleotide importers, are under direct heme epigenetic control[89]. Thus, to support the heavy metabolite trafficking activities, cancer heme overdrive is also probably associated with a wide range of cancer microenvironments.

Cancer cells do not exist in isolation: aggressive cancers successfully remodel not just their metabolism but also their immediate cellular environment. In fact, recently, cancer-associated stromal cells, such as cancer-associated fibroblasts (CAFs), were shown to shape the cancer cell niche and promote cancer progression[94,95] Preliminary evidence suggests that heme overdrive is present in cancer niche cells. As such, targeting heme overdrive can potentially kill both the cancer and the partner cells in the tumor microenvironment (based on the analysis of available single-cell solid tumor data (unpublished results)). Such dual lethality may be attributed to the fact that CAFs are highly anabolic and have increased collagen production and growth factor secretion[96,97], a set of features uniquely shared with cancer cells.

Cancer heme overdrive is similar, yet opposite in magnitude, to human porphyrias, a group of inborn genetic diseases mostly caused by reduced enzyme activities[98]. It is of interest to note that, except the erythroid lineage ALAS2 gain-of-function porphyria, no gain-of-function of human porphyria's (similar to cancers) have ever been reported[98], suggesting possible developmental lethality. Thus, cancer's imbalanced heme biosynthesis likely causes elevated pools of heme metabolites, while most porphyria's likely cause reduced heme synthesis.

The following non-limiting examples illustrate exemplary compositions and methods of treatment thereof in accordance with various embodiments of the disclosure. The examples are merely illustrative and are not intended to limit the disclosure in any way.

Example 1—Heme Overdrive in Cancer

Heme, a porphyrin ring encaging most of the iron in humans, functions as an essential prosthetic group of numerous proteins with roles ranging from signal sensing, DNA binding, microRNA splicing and processing to catalysis[15]. To ensure the enormous output of heme biosynthesis, the supply of substrates, intermediates and end-products in the pathway is tightly regulated and precisely balanced[7]. The inventors have found that cancers surprisingly forgo this highly regulated and efficient conventional heme biosynthesis pathway, and do not need to make their own heme.

Cancer is Characterized by Aberrant Heme Metabolism

Figure 2:
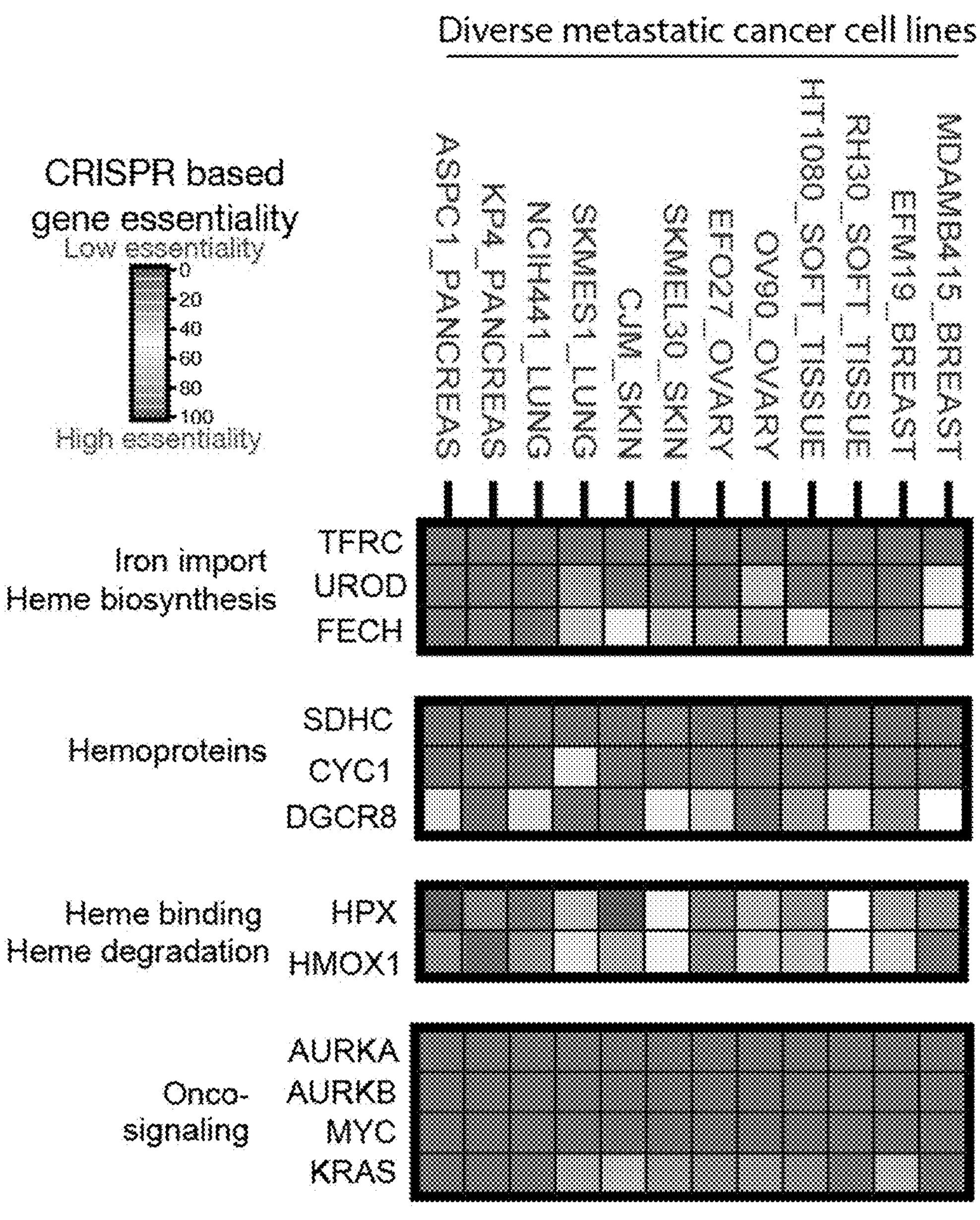
FIG. 2 is an image depicting dependency on heme metabolism in many metastatic types of cancer. The data for the CRISPR/Cas9-gene targeting of the genome-scale loss-of-function screens in a set of cancer cell lines were retrieved from DepMap. The columns refer to different cancer cell lines, while the rows refer to specific genes. Note the differences between the loss-of-function scores for specific proteins associated with heme biosynthesis (UROD and FECH) in this panel of metastatic cancer cell lines. [Abbreviations: AURKA, Aurora kinase A; AURKB, Aurora kinase B; CYC1, cytochrome c-1; DGCR8, DiGeorge syndrome critical region 8; FECH, ferrochelatase; HMOX1, heme oxygenase 1; HPX, hemopexin; SDHC, succinate dehydrogenase complex subunit C; TFRC, transferrin receptor; UROD, as uroporphyrinogen III decarboxylase].

Compared to normal cells, cancer cells have enhanced metabolic dependencies[26-28]. Cancer cells are dependent on imbalanced heme metabolism (FIG. 1A). The initial data analyses of genome-scale CRISPR/Cas9-gene loss-of-function from the publicly available project DepMap screens of cell lines derived from metastatic cancers[38] indicated that cancer cells depend on heme synthesis (FIGS. 2 and 3). Significantly, these metastatic cancers developed dependencies on heme metabolism-related proteins, such as uroporphyrinogen III decarboxylase (UROD), the enzyme that catalyzes the fifth step in the heme biosynthetic pathway. These cancers also depend on a set of hemoproteins, such as cytochrome c-1 (CYC1), succinate dehydrogenase complex subunit C (SDHC) for cellular respiration, and DGCR8 for microRNA biogenesis[39], each of which uses heme as a co-factor. Unexpectedly, the FECH gene that encodes ferrochelatase that catalyzes the final critical step of heme biosynthesis is dispensable in several cancers, suggesting that cancer cell lines are capable of bypassing endogenous biosynthesis of heme in vitro, yet are still dependent on genes encoding enzymes that mediate intermediate steps of heme biosynthesis.

Figure 4:
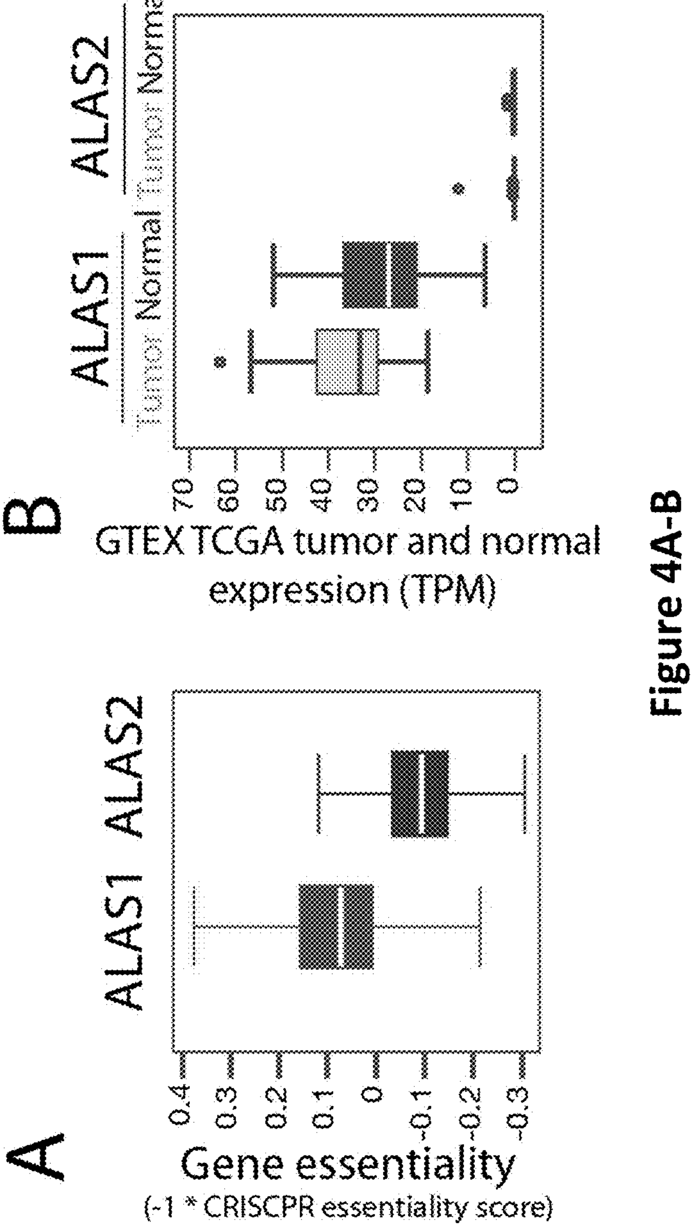
FIG. 4A-B are a series of images depicting ALAS1 and ALAS2 have different gene essentiality and pan-cancer gene expression patterns. (A) The isozyme gene pair ALAS1 and ALAS2 have different gene essentiality based on CRISPR/Cas9 loss-of-function results. ALAS2 was found not to be essential in any of the 27 major cancer types in over 300 cell lines, including erythroleukemia cell lines. The Y-axis label "CRISPR KO gene dependency" refers to the essentiality of ALAS1 or ALAS2. The essential score was used to evaluate the cell growth fitness. An essentiality score of 0, <0 and >0 indicates no fitness change, fitness loss and fitness gain under the same experimental conditions, respectively. (B) A study of ~10,000 patient derived tumors from GTEx and TCGA shows that ALAS1 expression is elevated in tumors compared to normal cells, while like in normal cells, ALAS2 expression is absent in most cells, except myeloid leukemia cells. However, the ALAS2 expression levels in normal erythroblasts do not significantly differ from those in cancer erythroblasts and myeloid leukemia cells. The dots indicate outliers of the samples with respect to ALAS expression. TPM, transcript per million.

Next, the inventors investigated the genes that encode proteins acting as gatekeepers for heme biosynthesis. The first committed and key regulatory step in mammalian heme biosynthesis is catalyzed by 5-aminolevulinic acid (ALA) synthase (ALAS; EC 2.3.1.37)[22,40]. Two chromosomally distinct genes, ALAS1 and ALAS2, encode the housekeeping and erythroid-specific ALAS isoforms, respectively[41]. While ALAS1 is expressed in every cell, the expression of ALAS2 is restricted to developing erythrocytes[40]. The inventors examined the data generated from genome-wide CRISPR-based screens of diverse cancer cell lines, which were designed to provide a complete gene essentiality data set for these cell lines[38,42]. In contrast to ALAS2, essentiality of ALAS1 is a feature of diverse cancer cell independent of cancer type (FIG. 4A). Consistent with these forward genetics results, the gene expression patterns in ~10,000 patient tumors from the Genotype-Tissue Expression (GTEx) 43,44 and The Cancer Genome Atlas (TCGA) 45 datasets show that ALAS2 expression is absent in most tumors except myeloid leukemias (FIG. 4B). These results show that, despite ALAS2 being responsible for the majority of heme production (~85%) in humans, many cancer cells, including erythroleukemia of red blood cell lineages (e.g. HEL), require ALAS1.

Heme Overdrive Operates in Diverse Cancers In Vitro and In Vivo

To better understand the molecular and genetic mechanisms underlying the cancer dependency on heme metabolism, the inventors determined gene essentiality from genome-scale CRISPR/Cas9 loss-of-function screens in over 300 human cancer cell lines covering different cell lineages and estimated gene dependency[38,42]. Then, the inventors focused on the gene dependencies associated with the eight enzymatic steps of the heme biosynthetic pathway by computing the respective pan-cancer essentiality scores, similar to the lethality scores used in the development of a cancer dependency map (DepMap)[42, 43] Gene essentiality was estimated from gene X dependency inferred from CRISPR/Cas9 gRNA gene X knockout. Lower score values indicate larger effect of gene X loss on cell viability, and hence cell lines with lowest and highest scores are most and least gene X-dependent, respectively. Consistent with recent cross-platform studies[46-47], over 5000 genes were defined as pan-cancer essential, based on the distribution of their essentiality scores in over 300 cancer lines derived from 27 of the most prevalent cancer types. The gene essentiality scores were confirmed by using the same method on the total DepMap collection (DepMap release 21Q3) of over 1000 cell lines (Pearson's $R>0.9$, $p<0.001$).

Figure 5:
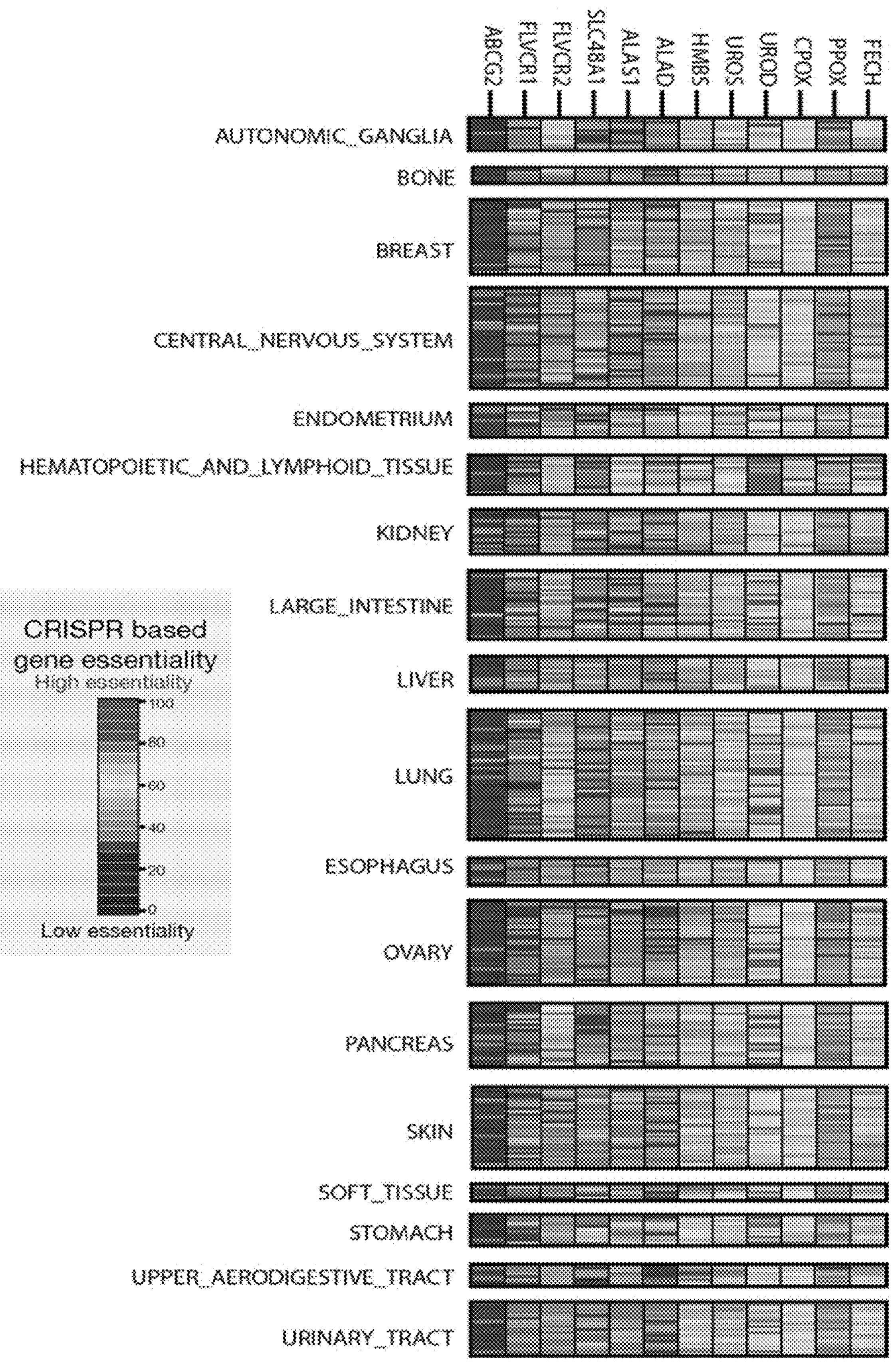
FIG. 5 is an image depicting CRISPR/Cas9 gene targeting and inferred gene essentiality in cancer cells exemplifies heme overdrive. A total of over 300 cancer cell lines from 27 major cancer types are analyzed. The data set represents 18 human tissue types that give rise to diverse groups of cancer. Whole genome loss-of-function growth phenotypes show most cancer cells only require a partial heme biosynthetic pathway to survive. Gene essentiality is estimated from gene X dependency inferred from CRISPR/Cas9 gRNA gene X knockout. Low and high cell viability with deletion of gene X indicate that the cancer cells have a high and low dependence on gene X for survival, respectively. Thus, the lowest and highest gene essentiality values are associated with the least and most profound dependence of the cells on the loss of gene X-dependent, respectively. The UROD gene for the fifth enzyme of the pathway has the highest essentiality in all types of cancers, while genes encoding other enzymes are dispensable in many cancer cell lines. Each of the rows in the 18 human tissue panels represents a distinct cancer cell line for the pertinent tissue. [ABCG2, ATP-binding cassette (ABC) transporter subfamily G, member 2; ALAD, ALA dehydratase (aka porphobilinogen synthase); ALAS1, 5-aminolevulinate synthase 1; CPOX, coproporphyrinogen oxidase; FECH, ferrochelatase; FLVCR, feline leukemia virus subgroup C receptor family; HMBS, hydroxymethylbilane synthase; PPOX, protoporphyrinogen oxidase; SLC48A1, solute carrier family 48, member 1, a.k.a heme transporter HRG1; UROD, uroporphyrinogen III decarboxylase; UROS, uroporphyrinogen III synthase]
Figure 7:
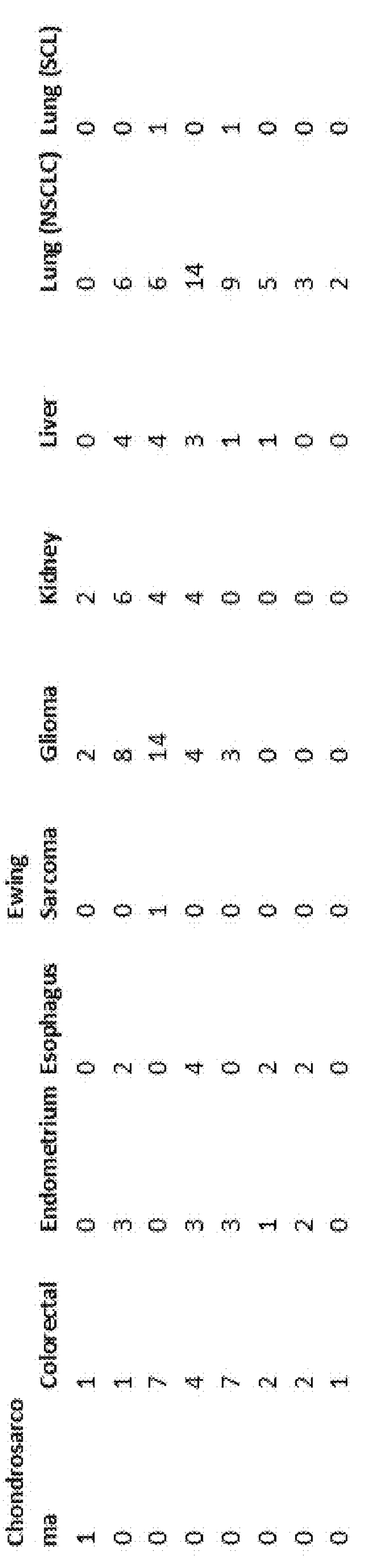
FIG. 7 is a table depicting partial heme biosynthetic pathway requirement for in vitro cancer cell growth.
Figure 7:
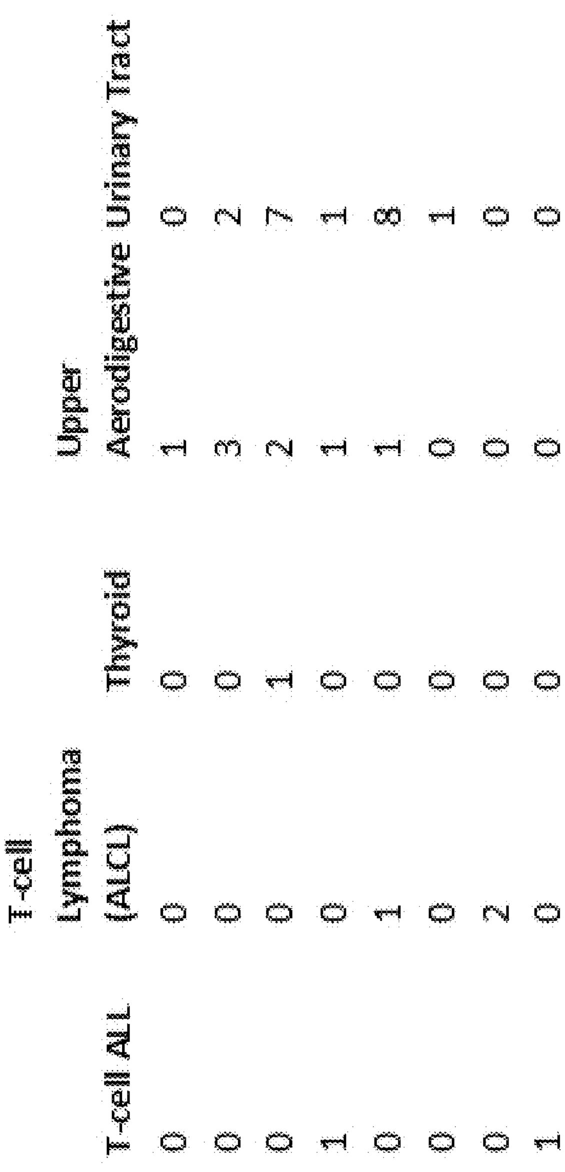
Figure 8:
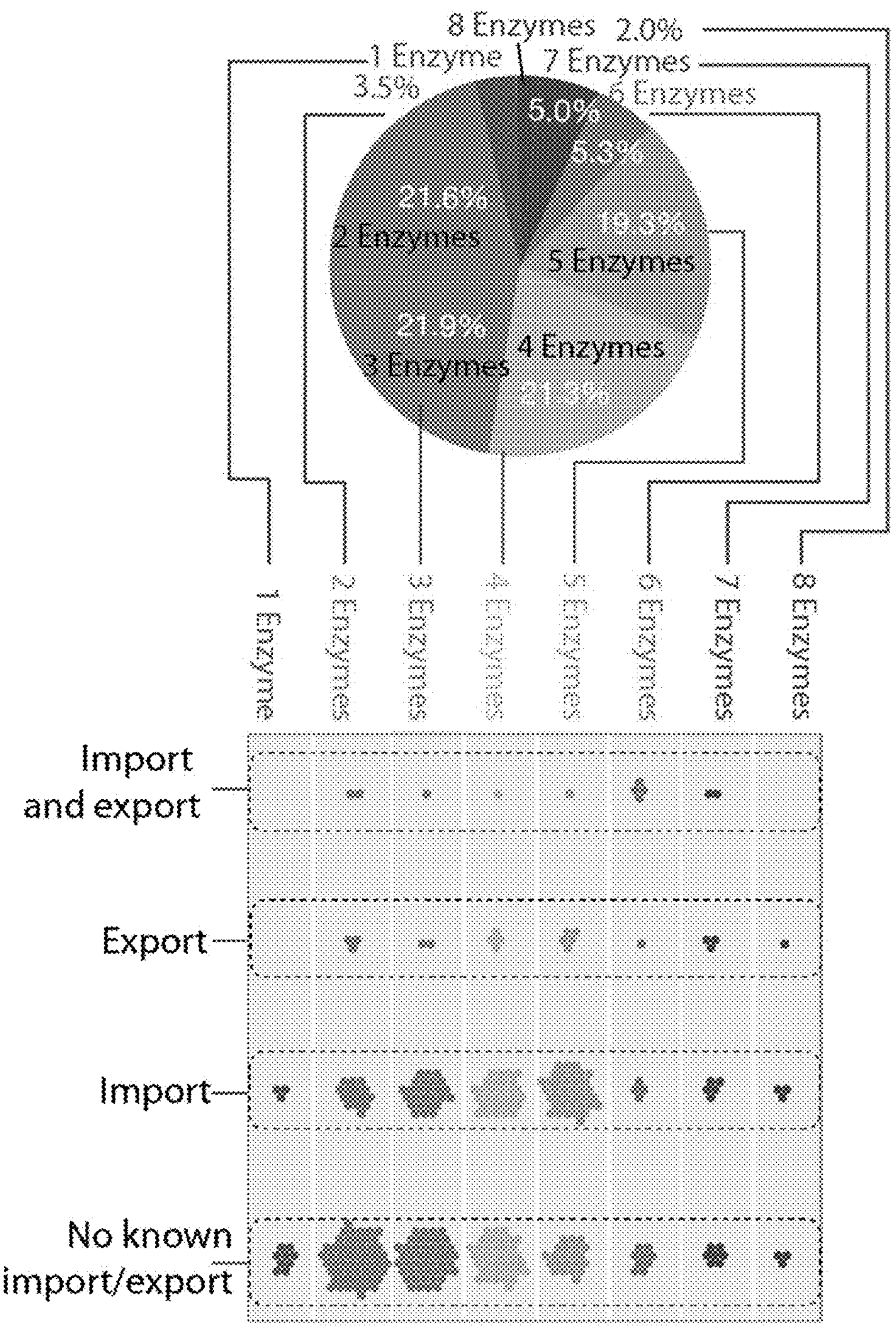
FIG. 8 is an image depicting analysis of heme overdrive in diverse cancer cell types. Most cancer cells from diverse lineages (27 major cancer types) representing 18 tissues show features of heme overdrive based on CRISPR KO gene essentiality analysis. There are 8 enzymatic steps for heme biosynthesis, represented by nine genes with 2 different genes for the first enzyme ALAS. ALAS2 was not included in this analysis because it is an erythroid lineage-specific gene. Classification of heme overdrive metabolism in eight groups is based on the number of essential enzyme-encoding genes in the heme biosynthetic pathway. Each of the groups is represented by a colored sector of the pie chart with an area corresponding to the percentage of the cancers with a specified partial number of functional heme biosynthesis enzymes as inferred from the gene essentiality results. For each of these groups, the gene essentiality of known heme importers (FLVCR2, SLC48A1) and exporters (FLVCR1, ABCG2) was also characterized. The number of trafficking genes is likely a conservative estimate as the field is still developing. Over 80% of the total cancer cells require only a "partial" heme biosynthetic pathway of 2-5 functional enzyme genes to survive, indicating the widespread 'incomplete' heme biosynthesis in cancer cells. One single enzymatic step suffices in 3.5% of all tested cancer cells, and the data reflect the heightened requirement of the intermediate enzyme/genes (e.g., HBMS, UROS, UROD and CPOX).

Strikingly, instead of finding the expected complete and balanced heme biosynthetic pathway, partial heme biosynthetic pathways were found in hundreds of different types of cancers (FIGS. 5-7). Specifically, as shown in FIG. 1B and FIG. 5, the pan-cancer gene essentiality is the highest for the genes encoding the enzymes responsible for the fifth and sixth steps of the pathway, UROD and coproporphyrinogen III oxidase (CPOX), respectively. This result was notably surprising, as the genes for the ALAS isoforms, which catalyze the initial and rate-limiting step in the pathway, and the gene for FECH, the final enzyme in the pathway that catalyzes heme production, had lower essentiality values and were dispensable in several cancers (FIG. 1B). Though the heme biosynthesis genetic dependences of 27 major forms of human cancer vary, the estimated patterns of essentiality across the cancer lines clearly revealed a range of heme and heme precursor requirements. These results uncovered the "imbalanced" nature of heme biosynthesis in cancer, with many cancers surviving without functional first and terminal enzymatic steps, but dependent on the intermediate steps such as UROD and CPOX (FIGS. 5 and 8). The gene essentiality analysis also highlighted the importance of heme trafficking (e.g., heme importer FLVCR2) and key hemoproteins (e.g., CYC1) in cancer cells survival (FIGS. 1B and 5).

To examine cancer heme metabolism in vivo, the inventors analyzed the in vivo mouse CRISPR/CAS9 loss-of-function and metabolic essentiality data from pancreatic and lung cancer models[48]. The genetic screen 48 indicates that the majority of metabolic gene essentialities were similar between the in vitro and in vivo settings, with the exception of the heightened requirement of the intermediate steps of heme biosynthesis in vivo. Strikingly, out of the ~2900 examined metabolic genes[48], the genetic dependencies of both murine pancreatic and lung cancers were only increased for genes that encode the heme metabolic enzymes responsible for the intermediate steps (HMBS, UROS, CPOX, and PPOX) of the heme biosynthesis pathway (FIGS. 9 and 10). The essentiality extent of either ALAS or FECH, which code for the first and terminal enzymes of the heme biosynthesis pathway, respectively, did not differ significantly between the in vivo murine cancer models. This analysis of the CRISPR/Cas 9 loss-of-function screens performed in mouse model systems revealed that aberrant heme metabolism has increased importance in vivo for cancer cell survival suggesting crosstalk of tumor cells and their TME with respect to aberrant heme metabolism (FIG. 9). Furthermore, this effect is independent of tumor origin or tissue environment in pancreatic and lung cancers.

To assess heme biosynthesis in patient tumor samples, the inventors analyzed and compared the gene expression patterns in ~10,000 tumors vs. those in normal tissues available from the GTEx project43,[44] and TCGA program[45]. Methods designed for pairwise comparative gene expression of GTEx and TCGA datasets[49] were used. In over 80% of all tumors, the genes for hydroxymethylbilane synthase (HMBS), the third enzyme of the heme biosynthetic pathway, and the heme exporter FLVCR1 were among the most upregulated (FIGS. 11A,B and 12). By the same criteria, the onco-signaling genes AURKA, KRAS and MYC were upregulated in over 90%, 60%, and 50% of all tumor types, respectively. In contrast, expression of the genes encoding the second and terminal enzymes of the heme biosynthetic pathway, aminolevulinate dehydratase (ALAD, a.k.a. porphobilinogen synthase) and ferrochelatase (FECH), respectively, are down-regulated suggesting buildup of intermediate heme precursors in tumors. HPX, the gene for the heme-binding and scavenger hemopexin[50], was also down-regulated in most of the tumors (FIG. 11C). This finding, which corroborates the previously reported role of hemopexin as a key player for the checkpoint in cancer growth and metastases[51], leads us to suggest that heme content is high in the tumor microenvironment[52]. ALAS2 belongs to the 10% of genes that were not expressed in most of the large tumor collections, except myeloid leukemias (<2% of total tumors). Overall, the comparative analysis of the differential gene expression in tumor tissues, spanning[31] cancer types, indicated that only a few of the nine heme biosynthesis enzyme-encoding genes were upregulated in cancer cells. The unbalanced expression of the genes for heme biosynthesis and heme transporters likely elicits a lack of heme homeostasis in cancer cells, where the insufficient heme supply from the dedicated biosynthetic pathway is compensated with an enhanced heme flux.

Based on the gene essentiality results both in vitro (FIGS. 1B, 5, and 8) and in vivo (FIG. 9) settings, the pan-cancer gene expression patterns (FIG. 11), the detected porphyrin accumulation in a wide range of tumors[30], and the determined elevated heme flux in diverse cancer cells[32,34,53], the inventors defined the salient heme overdrive-associated features. They are: 1) heme biosynthesis enzymes with aberrantly increased (HMBS, UROS and UROD) and suppressed (ALAD and FECH) activities, 2) accumulation of heme precursors (porphyrins), and 3) enhanced heme flux (FIGS. 1A and B). This cellular status contrasts with the tightly regulated steady-state or homeostasis, defined by a flawless enzyme-catalyzed channeling of substrates to products along the heme biosynthetic pathway and circumventing the toxicity and instability of the pathway intermediates, while ensuring that the cell heme requirements are met[7]. With heme overdrive, the production of heme precursor molecules exceeds that of heme, porphyrin intermediates accumulate, and "imbalanced" heme biosynthesis of increased porphyrin intermediates and decreased end-product arises. Likely, to compensate for the reduced amount of heme synthesized, heme flux is increased[30]. Cancer cells appear to have adopted a dependence on this seemingly "inefficient" metabolic pathway designed to produce aberrant levels of heme intermediates with unknown biological functions to date.

Heme Overdrive Operates in Preimplantation Human Embryos

Early embryonic stem cells represent a special metabolic state that bears similarities with that of cancer cells[54,55]. Therefore, the inventors also studied the expression of the heme biosynthetic enzyme-encoding genes in human preimplantation embryos and embryonic stem cells. Specifically, the inventors explored a high-resolution data set generated upon single-cell RNA-sequencing in human early embryonic cells and embryonic stem cells[56,57]. In the human zygote and early preimplantation embryos before the 8-cell stage, the heme biosynthesis genes show evidence of high level of imbalance that over 100-fold expression differences exist between the individual steps, e.g. the level of ALAS1 expression is 100-fold higher than that of FECH (FIG. 1C). This large difference in gene expression for two key enzymes in heme biosynthesis was observed in all 17 early human embryos examined. The significant difference in expression levels is restricted to very early embryos because it rapidly narrows to a 1-2 fold difference after initial rounds of embryonic cell division, e.g. via an increase in FECH expression and a decrease in ALAS1 expression. ALAS2 expression is not detected in any of the early human embryos, which is congruent with the non-essentiality of ALAS2 in all examined cancers. As a control, the genes AURKA and SOX4 show expected expression patterns during early embryogenesis 58,59. The similarity of these gene expression data with those observed in cancer cells supports the possibility that a form of heme overdrive operates in preimplantation human embryos, with high-levels heme-intermediates accumulating specifically the phase of embryonic omni-potency.

Heme Overdrive is Absent in Normal Cells

To evaluate if heme overdrive is specific to cancer cells, the inventors investigated and compared heme biosynthesis in diverse types of non-cancerous cells, i.e., normal differentiated cells, replicating fibroblasts, human primary hepatocytes, and human primary hematopoietic stem cells. The inventors searched for evidence of heme overdrive, defined by a nonhomeostatic, imbalanced heme biosynthetic pathways and heightened accumulation of heme pathway intermediates. Using published datasets, the inventors found that heme overdrive, observed in cancer cells, is absent in normal differentiated cells and somatic stem cells (FIG. 13A) First and consistent with this finding, normal human peripheral blood mononuclear cells (PBMCs) do not accumulate heme intermediates even upon ALA induction[60]. Second, colon cancer cells incubated with ALA to induce protoporphyrin IX (PPIX) production do accumulate PPIX, while no significant PPIX accumulation is observed in replicating human colon-derived fibroblasts (stromal cells) previously incubated with ALA[61]. Further, the increased HMBS activity in colon cancer cells relative to stromal cells[61] is consistent with a buildup of heme intermediates including PPIX. Third, with the previously described primary human hepatocyte system[62], the inventors demonstrated that normal, metabolically active, primary hepatocytes do not accumulate porphyrins as indicated by the absence of the PPIX fluorescence (FIG. 13B). By contrast, >99% of liver cancer cells produced and accrued PPIX upon induction with ALA, one of the canonical features of heme overdrive. The practice of ex-vivo purging of cancer hematopoietic progenitor cells, via ALA-induction/photodynamic therapy as a way to eradicate malignant cells while sparing hematopoietic stem cells[65] shows heme overdrive is absent in normal stem cells. Taken together, the markedly different porphyrin accumulation modes between cancer and non-cancerous cells indicate that heme overdrive is absent in normal cells.

To uncover the role of heme metabolism in normal human stem cells, the inventors analyzed the erythropoiesis data generated by RNAi-based knockdown of gene expression in human hematopoietic progenitor cells[63]. By mapping normal stem cell gene essentiality following the methods described in Egan et al.[63], the inventors showed that erythropoiesis is heme-dependent in both early progenitor (undifferentiated) cells and differentiated cells from normal human bone marrow-derived hematopoietic stem cells. In contrast to cancer cells, where ALAS2 is dispensable, normal human hematopoietic stem cells depend on ALAS2 for survival (FIG. 13C). The differential gene essentiality profiles between cancer and stem cells are consistent with the molecular basis for specific ex-vivo purging of cancer hematopoietic progenitor cells as a way to eradicate malignant cells that may contaminate an autologous graft and cause relapse after transplant[64,65]. Taken together, the distinct genetic essentialities and the markedly different porphyrin accumulation modes between cancer and non-cancerous cells indicate that heme overdrive is absent in somatic stem cells.

CRISPR/Cas9-Mediated Knockout of ALAS2 and FECH Validate Abnormal Heme Metabolism Underlying Cell Proliferation and Oncogenesis The inventors modified chronic myeloid leukemia K562 cells with CRISPR/Cas9-mediated knockout (KO) of the genes encoding FECH and ALAS2 (FIG. 13D). Under a heme homeostasis model, a cell line without FECH should not survive, because FECH is a single copy gene in humans and with no functional substitute[66-68]. Indeed, knockdown (KD) of FECH in human stem cells led to cell death[63]. However, under heme overdrive conditions, the inventors predicted that cancer cells rely on heme trafficking and are addicted to the porphyrin intermediates, and thus do not depend on the final step of heme biosynthesis for survival. As predicted, K562 cells with the FECH edited out (K562-FECH KO) (FIG. 13D) had normal growth (FIG. 13E) under standard culture conditions. The unimpeded growth of the K562-FECH KO cells presumably indicates that at least some cancer cell lines can metabolically function as heme auxotrophs.

As predicted, K562 cells with the ALAS2 deleted (K562-ALAS2 KO) (FIG. 13D) lost their differentiation capacity although their growth was not hindered (FIG. 13E, F). Given the proposal that oxidation stress, with the involvement of reactive oxygen species (ROS), is the first step in erythroid differentiation of K562 cells[69], the inventors used the organic peroxide tertbutyl hydroperoxide (t-BHP) to trigger ROS-mediated erythroid differentiation. As early as 30 minutes following t-BHP-mediated ROS induction, the parental K562 cells started synthesizing heme, an early step in cellular differentiation[69], while the K562-ALAS2 KO cells failed to initiate this metabolic step, indicated by the lack of heme production (FIG. 13F). Further, at 48 hours, the parental K562 cells readily differentiated into erythroid cells, but the K562-ALAS2 KO cells continued to proliferate and failed to differentiate, as expected because ALAS2 is required for erythroid differentiation. Conceivably, in the absence of endogenous production of heme destined to hemoglobin, the erythroid lineage commitment is blocked, forcing the K562-ALAS2 KO cells to an obligatory heme overdrive path and permanent arrest in a non-differentiable/proliferation or cancerous state.

Single-Cell Transcriptomics Reveal Heme Overdrive in AML Patient Biopsies

To study heme overdrive in primary cancer cells, the inventors performed single-cell RNAseq on biopsies from acute myeloid leukemia (AML) patients. For each patient, the inventors obtained around 2000 single-cell transcriptomes, and cells of various differentiation stages and cell types were analyzed. Interestingly, in 2 patients, only a minority of cells (5-10% of total cells) were identified as cancer progenitors with hyperproliferation features (FIG. 14A), and they exhibited hybrid features of mature erythroid cells (e.g. expressing the genes HBB and GYPA for hemoglobin b and glycophorin A, respectively) and stem cells (e.g. expressing SOX4). The cancer progenitor cells (FIG. 14B) had both mature cell features, e.g. HBB expression, and early progenitor properties, e.g. proliferative phenotype. Specifically, they were characterized by elevated iron and heme metabolic gene expression, cell proliferation markers, KRAS and anabolism process genes, yet they had reduced normal stem cell progenitor marker gene expression e.g., SOX4 and JUN (FIG. 14C)[70,71]. Additionally, cancer/AML progenitor cells exhibited imbalanced heme biosynthesis, exemplified by elevated gene expression for enzymes that catalyze the intermediate steps of heme biosynthesis, e.g. HMBS and UROD (FIGS. 14D and E). The cancer progenitor cells also had a higher expression level of genes related to heme trafficking such as FLVCR1 and DNM2 (FIG. 14C). The results showed that these cancer progenitor cells exhibit features of heme overdrive, consistent with the abnormal heme anabolism and endogenous PPIX accumulation upon ALA administration in leukemia cells compared to normal PBMCs[60]. Notably, in two solid tumors (FIG. 14F) with independently generated single cell transcriptomes[72,73], the genes encoding the enzymes for the intermediate steps of heme biosynthesis were similarly overexpressed in the cancer progenitor cells (FIG. 14F).

From the single cell transcriptome results, the inventors searched for clues of specialized oncogenic microenvironments that support enhanced substrate trafficking and molecular interactions. Interestingly, only the cancer progenitor cells highly express cell-to-cell interaction-related genes, e.g., ICAM4, MAEA, ITGA4 (FIG. 15A), which are critical in establishing the stem cell niche for erythropoiesis[74-75]. The specific expression of these niche interaction genes suggest that the cancer progenitor cells exist in a specialized niche with intimate contact with neighboring cells and extracellular matrix.

Expression was remarkably enhanced for genes encoding proteins involved in metabolic substrate trafficking processes in the cancer progenitor cells, including genes for key protein players in lipid import, purine and pyrimidine salvage pathways (FIG. 15B). These specific metabolic flux related genes, such as DNM2 (endocytosis), APOC1 (lipid transport), MRI1 (L-methionine salvage), MTAP (NAD salvage), and SLC29A1 (nucleoside import) indicate that the cancer progenitor cells represent hubs of metabolic trafficking activities. In particular, the lipid import gene APOC1 is expressed in cancer progenitor cells, but not in the other cell populations from the same patient samples (FIGS. 16, A and B). The metastatin S100 family members linked to tumor niche construction[76] are also enriched in the progenitors. These potential dynamic metabolic trafficking patterns inferred from the abundant expression of metabolites import genes in cancer early progenitors (FIG. 15C) are reminiscent of 'metabolic parasitism'[77], a bioenergetically favorable process[78] that utilizes energy-rich and pre-existing macromolecules to fuel robust cell proliferation.

Targeting Cancer Heme Overdrive with a "Bait-and-Kill" Strategy

Two aspects of cancer heme overdrive offer opportunities for therapeutic intervention. First, an imbalanced heme biosynthetic pathway (i.e., with aberrantly increased and suppressed enzyme activities) is absent in normal cells. Second, heme overdrive is inducible hundreds to thousands-fold in cancer cells, but not in non-cancerous cells. In fact, photodynamic therapy (PDT), which uses ALA to induce biosynthesis and accumulation of photosensitizing porphyrins, exemplifying the inducible principle of heme overdrive, has been used for imaging and treatment for decades[79-81]. Thus, heme overdrive is a unique metabolic reprogramming feature of cancer cells that can be therapeutically exploited. Since an imbalanced heme flux is fundamental to heme overdrive, cancer cells may be made particularly vulnerable to PPIX-induced cytotoxicity. Selective cancer cell death can be achieved by activating PPIX-induced cytotoxicity with a two-step "bait-and-kill" strategy.

Knowing that cancer cells readily take up the heme precursor ALA and bypass the first and rate-limiting step of porphyrin biosynthesis catalyzed by ALAS, the inventors assessed the engineered two-step process for cancer metabolic death. This two-step process involves first, to 'bait' with ALA to induce PPIX accumulation up to a few hundred-to-thousand-fold higher concentration as compared to control cells (FIGS. 17A and B), and second, to 'kill' with a compound that exploits the metabolic stress associated with porphyrin accumulation.

To exploit the metabolic stress (e.g., lipid peroxidation) associated with porphyrin accumulation, the human erythroleukemia HEL cell line was treated with a range of concentrations of RSL3, an inhibitor of the antioxidant enzyme glutathione peroxidase 4 (GPX4), a phospholipid hydroperoxidase that protects cells against membrane lipid peroxidation. As such, inhibition of GPX4 with RSL3 induces ferroptosis, an iron dependent form of programmed cell death highly relevant to iron and heme metabolism[82]. Pretreatment of HEL cells with ALA increased RSL3 sensitivity at least 1000-fold (FIGS. 17, C and D). Even at a RSL3 concentration of 100 mM, the viability of HEL cells remained similar to that of cells cultured in the absence of the RSL3 inhibitor. However, the viability of HEL cells grown in the presence of ALA for 4 h diminished with RSL3, reaching non-viability at a concentration of 17 mM. The decline was yet more acute when the incubation time of the HEL cells with ALA was extended to 24 h, and the cells became non-viable with 16 nM RSL3. In contrast, ALA pretreatment did not sensitize cells to ganetespib, a heat shock protein inhibitor with antineoplastic activity[83], suggesting that ALA is not a general inducer or sensitizer of cell death. Specifically, at ganetespib concentrations greater than 33 mM, HEL cells persist viably regardless of being grown in the presence or absence of ALA (FIG. 17D). Importantly, no synergistic cytotoxic effects are found in control primary human fibroblasts (FIG. 18). Normal cellular growth and replications are unaffected in mM range of IC50 of RSL3.

Materials and Methods

Cell Culture

The human chronic myelogenous leukemia cell line K562 (ATCC, Cat No. CCL-243) and human erythroleukemia cell line HEL 92.1.7 (ATCC, Cat No. TIB-180) were obtained from the American Type Culture Collection. Both the cells were grown in RPMI 1640 medium (Gibco) supplemented with 10% fetal bovine serum (Sigma), gentamicin (1000×, Fisher, Cat No. 15-710-072), PennStrepNeo solution (100×, Fisher, Cat No. 15640-055) and 2 mM L-glutamine at 37° C. in a humidified 5% $CO_2$ atmosphere. 5-Aminolevulinic acid hydrochloride (ALA), purchased from Alfa Aesar (Cat No. A16942ME), was dissolved in distilled water to yield a stock concentration of 1.0 M, and stored at −20° C. Glycine, purchased from Fisher Chemical (Cat No. BP381-500), was dissolved in phenol red-free culture medium purchased from Gibco (Cat No. 11835055) to give a stock concentration of 1 M.

Cell Growth and Quantification

K562 or HEL cells were plated at 1-2×$10^5$/mL, and cells were counted by trypan blue (Corning, Cat No. 25-900-CI) exclusion over time, with passage back to the starting cell density as needed. Total cell numbers were determined based on the passage dilution at each time point, on a disposable hemocytometer (Incyto, Cat No. DHC-N01).

Generation of Knockout Cell Lines by CRISPR

K562 cells containing deletions in ALAS2 or FECH were created using a multi-guide strategy via nucleofection (Lonza) of Cas9/RNP complexes (Gene Knockout Kit v2, Synthego) following manufacturer instructions. CRISPR/Cas9 deletions were confirmed following amplification of the genomic region of interest, Sanger sequencing of the amplified genomic region, and Inference of CRISPR Edits (ICE) analyses (Synthego). Cells were lysed in RIPA buffer with protease and phosphatase inhibitors and immunoblotted with antibodies that recognize ferrochelatase (SC-377377) and vinculin (SC-73614) (Santa Cruz Biotechnology). PCR amplification of first strand cDNA from K562 and K562-ALAS2 KO was used to confirm the presence of the homozygous 107 bp out-of-frame deletion that was detected in the ICE analyses of the edited genomic region in K562-ALAS2 KO cells.

In Vitro Erythropoiesis Protocols

In vitro erythropoiesis was monitored by following cellular differentiation of the cell lines (K562 and K562-ALAS2 KO) with benzidine staining. The benzidine solution was prepared by mixing 5 mL of 30% hydrogen peroxide ($H_2O_2$) with 1 mL of 0.2% benzidine dihydrochloride in 0.5 M acetic acid. Around one million cells were washed thrice with in Dulbecco's phosphate-buffered saline (DPBS, 1×; Corning, Cat No. 21-031-CV) before being resuspended in 250 μL of 1×DPBS mixed with 250 μL benzidine solution and incubated at room temperature for 10 minutes. The cells stained brown-blue were visually recognized and counted as positives, on a disposable hemocytometer (Incyto, Cat No. DHC-N01). The experiments were conducted in triplicates, and multiple microscopic fields were counted.

AML Patient Single Cell RNAseq and Heme Biosynthetic Pathway-Related Gene Expression Analysis Cells were obtained from human donors with over 60% blast expansions in marrow biopsies. Blast cells were washed and isolated according to standard tissue-banking protocols. Cells were carefully washed in in Dulbecco's phosphate-buffered saline (DPBS, 1×; Corning, Cat No. 21-031-CV) and resuspended at $10^6$ cells/mL to avoid cell aggregates. Cells were processed using the 10× Genomics Chromium controller and the Chromium single cell 3' library and gel bead kit (10× Genomics, Cat No. PN-1000075) following the standard manufacturer's protocols. First, gel beads-in-emulsion (GEMs) were generated by combining barcoded single cell 3' v3 gel beads, a master mix containing cells, and partitioning oil onto Chromium chip B. To achieve single cell resolution, cells were delivered at a limiting dilution, such that the majority (~90-99%) of generated GEMs contain no cells, while the remainder contain predominantly a single cell. Between 2,000-21,000 live cells were loaded onto the Chromium controller to recover between 1,500-15,000 cells for library preparation and sequencing. Immediately following GEM generation, the gel beads were dissolved, primers were released, and any co-partitioned cells were lysed. An Illumina TruSeq Read 1 (read 1 sequencing primer), 16 nt 10× barcode, 12 nt unique molecular identifier (UMI) and 30 nt poly(dT) sequence were mixed with the cell lysate and a master mix containing reverse transcription (RT) reagents. Incubation of the GEMs produces barcoded, full-length cDNAs from poly-adenylated mRNAs. Next, GEMs were broken, and cDNA was amplified and quantified using an Agilent high sensitivity DNA screentape (Agilent Technologies, Cat No. 5067-5592). SPRIselect magnetic beads (Beckman Coulter, Cat No. B23317) were used to purify the first-strand cDNA from the post GEM-RT reaction mixture, which included leftover biochemical reagents and primers. Barcoded, full-length cDNA was amplified via PCR to generate sufficient mass for library construction. Enzymatic fragmentation and size selection were used to optimize the cDNA amplicon size. TruSeq Read 1 (read 1 primer sequence) was added to the cDNAs during GEM incubation. P5, P7, a sample index, and TruSeq Read 2 (read 2 primer sequence) were added via end repair, A-tailing, adaptor ligation, and PCR. The final library quality was assessed using an Agilent Bioanalyzer high sensitivity chip. Samples were then sequenced on the Illumina NextSeq 550 with a target of 150,000 reads/cell.

The Cell Ranger Single-Cell software Suite (10× Genomics) was used for data processing, sample demultiplexing and gene expression quantification. For data analysis, genes with more than one unique molecular identifier (UMI) counts were used. The top 1000 most variably expressed genes were used for further clustering, and t-Distributed Stochastic Neighbor Embedding (t-SNE) analysis was performed to reduce the data dimension to a two-dimensional space, and k-means clustering was used to identify cell populations. The mean expression of genes in all cells in a given cluster was calculated, and the expression of each gene was compared with that of the same gene in all the other clusters. For cell classification, the mean expression profiles of all cells were first calculated, and then each cell was assigned to a subpopulation by the highest Spearman's correlation.

Heme Biosynthetic Pathway-Related Gene Expression Analysis

The gene expression patterns related to heme biosynthesis from patient-derived tumor samples were analyzed using the publicly available resources to study tissue-specific gene expression, the GTEx project[43, 44] and TCGA program[45]. The heme biosynthetic pathway gene expression patterns in 10,000 tumors vs. matched normal tissues were used for analysis.

CRISPR Pan-Cancer Gene Essentiality Analysis

The data from the DepMap Portal were used to calculate the gene essentiality scores in a similar manner to published methods[38, 99, 100]. The whole genome CRISPR/Cas9 datasets were used to identify significantly depleted mutant cells bearing a specific gene knock out in a pooled experiment. Gene essentiality was estimated from a given gene dependency inferred from CRISPR/Cas9 gRNA gene knockout. The essential score was used to evaluate the cell growth fitness. The lower the essentiality score value, the larger the gene loss effect on cell viability. Thus, a score of 0, <0 and >0 indicates no fitness change, fitness loss and fitness gain (i.e., possible growth advantage for the cell line) under the assay conditions, respectively). The method as described in Aguirre et al.[99] and Kim et al.[100] was employed to correct the copy number bias in whole genome CRISPR/Cas screens by computing the mean of sgRNAs vs. the control plasmid library. Commonly essential genes were required for the fitness of most cell lines across cancer types[46,47]. For in vivo gene essentiality analysis in pancreatic and lung cancer models, the published data[48] were used to specifically examine the genes encoding the heme biosynthetic pathway enzymes and heme transporters.

In Vitro Primary Human Hepatocyte Culture, Quantification, and Imaging

Sterilized 384-well plates (Greiner, Cat No. 781091) were unpackaged in a class II biosafety cabinet and placed in a secondary container (i.e., plates were placed in large assay pans) to serve as a lid and control evaporation. The day prior to hepatocyte seeding, wells were collagen coated with 40 μL of 15 μg $L^{-1}$ rat tail collagen I (Corning, Cat No. 354236) in sterile filtered 0.02 M acetic acid (Thermo Fisher Scientific, Cat No.), and kept at 37° C. overnight. Immediately prior to seeding the wells were washed thrice with sterile phosphate buffered saline (PBS) and then filled with 20 μL in vitro GRO® CP plate medium (BioIVT, Cat No. Z99029) supplemented with 1× Pen-Strep-Neo solution (100×, Fisher, Cat No. 15640-055) and 20 μM gentamicin (1000×, Fisher, Cat No. 15-710-072). Vials of cryopreserved (male) primary human hepatocytes (BioIVT, Cat No. M00995-P) were thawed by immersion in a 37° C. water bath for 2 minutes, sterilized with 70% ethanol in a sterile field, and the contents were added directly to 4 mL plate medium. Live and dead cells were quantified by trypan blue exclusion on a Neubauer improved hemocytometer. The hepatocyte density was set at $1\times10^3$ live cells $\mu L^{-1}$, and 18 μL cell suspension was added to each well. Medium was exchanged with the GRO® CP plating medium, described above, thrice weekly. The cells were incubated with 1.0 mM ALA at 37° C. for 4 hours. Both ALA treated and non-treated cells were handled under very low light conditions. During the last 45 min of incubation, a staining solution diluted in phenol-free, serum-free RPMI (Gibco, Cat No. 11835055) containing Hoechst 33342 (Life Technologies, Cat No. H3570) at a final concentration of 10 μM, was added to the cells. Live cell imaging was performed on a CellInsight CX7 High-Content Screening Platform (Thermo Fisher Scientific), and each plate well was counted for hepatocytes nuclei staining.

In Vitro Hepatocyte Cell Line HC-04 Culture, Quantification, and Imaging

Cryopreserved HC-04 hepatocyte cells were thawed, suspended into a previously prepared hepatocyte culture medium, and transferred to a T75 flask coated with collagen (Corning, Cat No. 354236) at 5 μg/cm$^2$. The previously prepared hepatocyte cell-line culture medium consisted of a mixture of F12 base medium (Invitrogen, Cat No. 11765-054) and MEM base medium (Invitrogen, Cat No. A10490-01) on 1:1 (v/v) ratio, containing 10% FBS (Hyclone, Cat No. SH30070), 1.0 M HEPES (Invitrogen, Cat No. 15630-080) and 200 mM glutamine (Invitrogen, Cat No. 25030-081)[102]. Cells were allowed to grow until reaching 70% confluence, and the medium was changed every other day. Then, the cells were trypsin-hydrolyzed with TrypLE™ Express Enzyme (1×) (Gibco, Cat No. 12605028) and washed with hepatocyte culture medium. The HC-04 cells were seeded at a density of 6000 cells/well and cultured in 384-well plates (Greiner, Cat No. 781091) in 20 μl of the above medium/well. Cells were incubated either in the absence or presence of 1.0 mM ALA at 37° C. for 4 hours. Both ALA treated and non-treated cells were handled under very low light conditions. During the last 45 min of incubation, a staining solution diluted in phenol-free, serum-free RPMI (Gibco, Cat No. 11835055) containing Hoechst 33342 (Life Technologies, Cat No. H3570) at a final concentration of M, was added to the cells. Live cell imaging was performed on a CellInsight CX7 High-Content Screening Platform (Thermo Fisher Scientific), and each plate well covering 15 fields at 20× was counted for hepatocytes nuclei staining.

Cellular PPIX Quantification, TBHP-Induced Oxidative Stress, and Cell Viability Assay Protoporphyrin (PPIX) accumulation was determined using fluorescence-activated cell sorting (FACS) as previously described in Fratz et al.[40] K562 and K562-ALAS2 KO cells were independently seeded in 24-well plates for suspension culture (Greiner, Cat No. 662102) overnight at a density of 1.2×10$^5$ cells/well. The K562 and K562-ALAS2 KO cells were incubated in medium (described in the Cell Culture section) containing 1.0 mM ALA, at 37° C. for 4 hours. Preparation of either 5-ALA-treated cells or control (non-ALA-treated) cells was under very low light conditions. Following incubation, cells were washed thrice with Dulbecco's phosphate-buffered saline (DPBS, 1×, Ca$^{2+}$- and Mg$^{2+}$-free; Corning, Cat No. 21-031-CV) and resuspended in 250 μL of 1×DPBS. Briefly, cells were washed once with serum-free medium (Gibco, Cat No. 11835055) and incubated in 6-well plates containing the medium (described in the Cell Culture section) in either the absence or presence of 100 mM glycine or ALA (0.1 mM, 0.25 mM, 0.5 mM, and 1.0 mM) at 37° C. Intracellular PPIX concentration was measured 18 hours later by FACS. The cell suspension was passed through a 40-μm Flowmi™ Cell Strainer to eliminate clumps and debris prior to transferring to BD Falcon tubes under very low light conditions to minimize phototoxicity caused by PPIX accumulation. FACS analyses were performed using a BD LSR II Analyzer (Becton, Dickinson, and Company) and FACSDiva Version 6.1.3 software. To eliminate any background red fluorescence, the 633 nm-red laser was blocked during the collection of the PPIX emission data. PPIX emission was determined in the 619 nm and 641 nm range (630/22BP filter) upon excitation of the cells with the 405 nm laser. Forward-scatter (FSC) versus side-scatter (SSC) dot plots were used to gate the whole cells and thus remove the contribution of the cell debris from the population being examined. A minimum of 10,000 of the gated cells was then depicted in dot plots of SSC vs. PPIX fluorescence; the gate was defined based on wild-type K562 cells without any perturbation as negative controls.

Cellular Reactive Oxygen Species (ROS) Detection and Cell Viability Assays

Both K562 and K562-ALAS2 KO cultures were seeded in 24-well plates for suspension culture (Greiner, Cat No. 662102) at a density of 1.2×10$^5$ cells/well in the medium described in the Cell Culture section, at 37° C. overnight. After the incubation, cells were washed thrice with Dulbecco's phosphate-buffered saline (DPBS, 1×, Ca$^{2+}$- and Mg$^{2+}$-free; Corning, Cat No. 21-031-CV) and resuspended in 250 μL of 1×DPBS and stained for 30 min at 37° C. with 500 nM CellROX green reagent (Life Technologies, Cat No. C10444). During the last 15 min of staining, 1 μl of the 5 μM SYTOX Blue Dead Cell stain (Life Technologies, Cat No. S34857) was added to distinguish live from dead cells. Cells were immediately analyzed by fluorescence-activated cell sorting (FACS) using a BD LSR II Analyzer (Becton, Dickinson, and Company) and FACSDiva Version 6.1.3 software. Emission of the oxidized fluorogenic CellROX™ green was measured at 525 nm (530/30 BP filter) upon excitation of the cells using the 488 nm laser. K562 cells treated with 250 μM tert-butyl hydroperoxide (TBHP, Thermo Scientific, Cat No. 180340050) for 15 min were used as a positive control. K562 cells treated with 1 mM ALA for 4 hours as "PPIX fluorescence positive control". Both ALA-treated and non-treated cells are handled under very low light conditions.

Drug ("Bait-and-Kill") Assays

The compounds RSL3 (MedChemExpress, Cat No. HY-100218A) and ganetespib (MedChemExpress, Cat No. HY-15205) were dissolved in 100% DSMO (ATCC, Cat No. 4-X) to yield 10 mM stocks, which were stored at −80° C. until further use. HEL cells were seeded in 38-well plates (Greiner, Cat No. 781091) at a density of 6000 cells/well and in 20 μl of medium (described in the Cell Culture section) per well. The cells were allowed to proliferate for the next 48 hours. Both ALA treated and non-treated cells were handled under very low light conditions throughout the assay. The cells were treated with 1 mM ALA in individual plates for 4 hours and 24 hours. Both ALA-treated and non-treated plates were tested with the compounds RSL3 and Ganetespib in triplicate wells using an 18-point concentration format with 2-fold dilutions (final concentrations of 132 μM to 1 nM) bringing the total volume to 25.6 μl per well. Cell proliferation was measured utilizing the CellTiter-Glo 2.0 reagent (Promega, Cat No. G9243) to quantify cellular ATP according to manufacturer's instructions by adding 25.6 μl of the reagent per well. Luminescence was measured with a Clariostar Plus Microplate Reader (BMG Labtech). For each assay plate, a DMSO control (0.1%), a positive control, a negative control and blanks were added, and a minimum of 12 wells per plate were analyzed. Data were reported as arbitrary luminometric units (ALU).

Conclusion

In conclusion, through whole genome CRISPR KO analysis, single-cell transcriptomics using patient-derived tumor cells, and characterization of the heme biosynthetic pathway in engineered mammalian cells, the inventors found an unrecognized pivotal role of imbalanced and dynamic heme metabolism in oncogenesis. Heme overdrive is a process that is universal in cancer, cancer-specific and required for cancer cell survival, and can be exploitable with novel therapeutic approaches. For example, porphyrin accumulation due to heme overdrive and the resulting oxidative stress presents a vulnerability of cancer cells that can be amenable to novel therapeutic strategies to specifically destroy cancer cells. Finally, the studies provide a basis for exploring new avenues of research on the metabolic features of cancer cells and tumor microenvironments.

Example 2—Targeting Heme Overdrive in Cancer Cells

Figure 19:
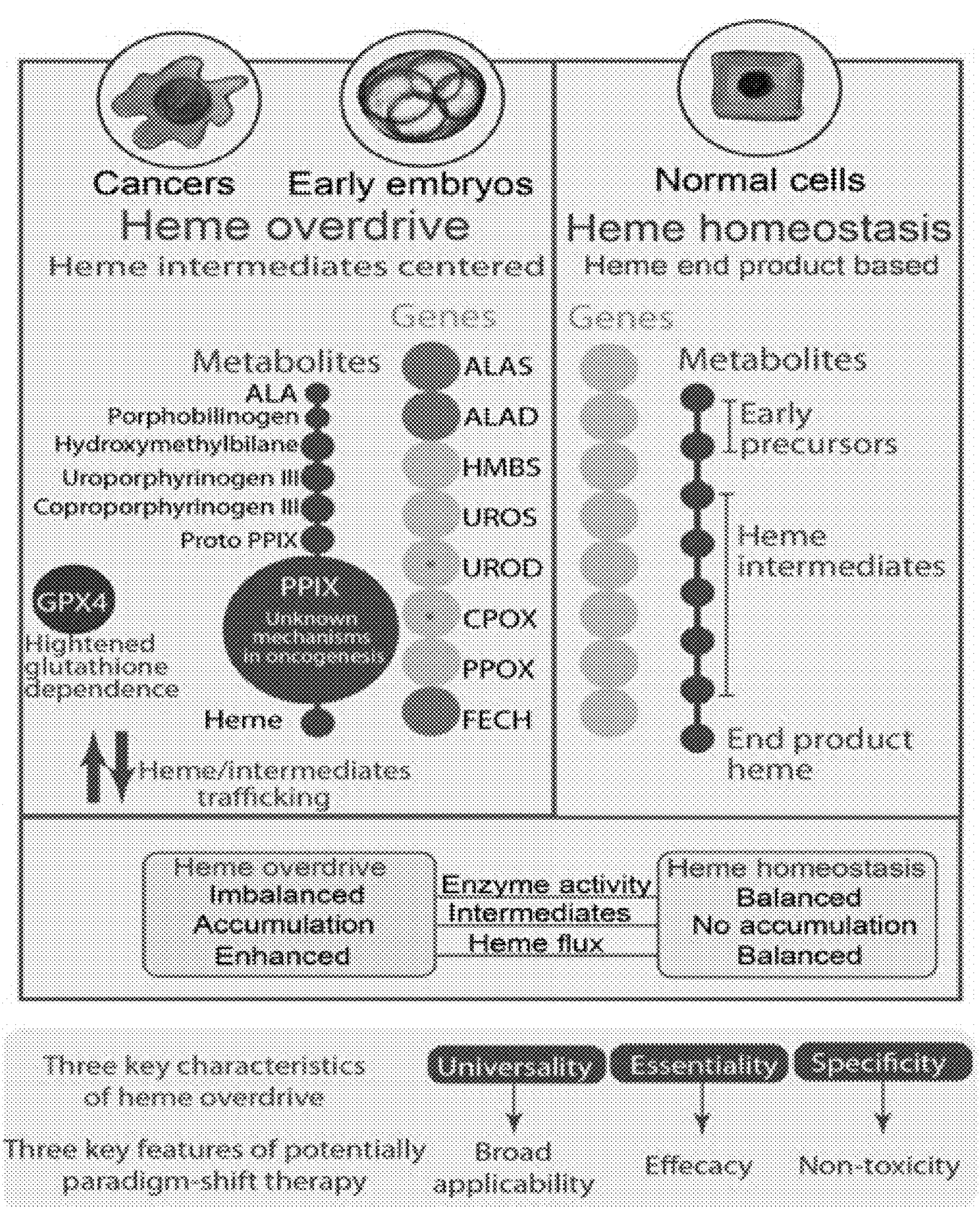
FIG. 19 is an image depicting heme homeostasis refers to the heme biosynthetic pathway in normal cells. The 8 enzymes of the linear heme biosynthesis pathway are drawn. The product of each enzymatic step are grouped as early precursors, heme intermediates, and end product heme. Heme overdrive refers to the imbalanced (i.e. with aberrantly increased and suppressed enzyme activities) pathway in cancer cells and early human embryonic cells. Heme intermediates have a universal yet unknown role in oncogenesis. The essentiality of genes are shown, yellow refers to essential; grey non-essential. The genetic essentiality data are based on in vivo CRISPR loss-of-function in cancers, normal stem cell genetic knock down loss of function in normal cells. The red stars in the cancer gene shows in vitro cancer cell line essentiality.

As discussed in Example 1, the inventors have discovered a cancer cell metabolic reprogramming that affects heme homeostasis. In normal cells, heme biosynthesis pathways (FIG. 19) consist of 8 enzymatic steps under tight regulation with the first step occurring in mitochondria and catalyzed by 5'-aminoLevulinic Acid (ALA) synthase (ALAS). Subsequent enzymatic steps occur in the cytosol and result in early precursors (e.g., delta-aminolevulinate (ALA), porphobilinogen), heme intermediates (e.g., hydroxymethylbilane, uroporphyrinogen III, coproporphyrinogen III, protoporphyrin IX (PPIX)) and heme end product (i.e., an iron ion coordinated to a porphyrin). This process is balanced leading to heme homeostasis that is critical to several cellular functions in normal cells (FIG. 19).

In contrast to normal cells, heme biosynthesis is altered in several ways in cancer cells. Unlike normal cells which require the enzymes for every single step of the heme biosynthetic pathway, cancer cells do not, and instead display a high dependency on a subset of these enzymes including HMBS (which catalyzes the 3$^{rd}$ step in the biosynthetic pathway), UROS (4$^{th}$ step), UROD (5$^{th}$ step) and CPOX (6$^{th}$ step) and low dependency on others (ALAS1) (FIG. 19). Heme transporters are also required for cancer cells, thus there is an imbalanced requirement for enzymes in this pathway and a requirement for heme precursor metabolites (called porphyrins, e.g., PPIX) beyond the synthesis of heme, as shown in Example 1 that there is an aberrant accumulation of heme precursors (e.g., PPIX) in cancer cells. The genetics and genomics data show that, a) cancer cells require genes for accumulation of heme intermediates (e.g., PPIX) for survival; b) they do not need genes to biosynthesize either early precursor (e.g., ALA, porphobilinogen), or heme end products for survival. and c) they only require genes encoding HMBS (3$^{rd}$ step), UROS (4$^{th}$ step), UROD (5$^{th}$ step) and CPOX (6$^{th}$ step) for survival.

There is a novel cancer cell metabolic reprogramming characterized by a requirement of heme-biosynthetic steps for a purpose other than producing heme that is essential for cancer cells but not normal cells. As noted in Example 1, the inventors refer to this imbalanced high dependence on a subset of heme biosynthetic steps as "heme overdrive" (FIG. 19). Remarkably, evidence for this altered dependency on heme metabolic enzymes is detectable in all cancer types. As such, heme-precursor metabolites may have a unique role in cancer cell properties.

As noted in Example 1, cancer, but not normal, cells are dependent on heme biosynthetic enzymes that make heme-precursor metabolites, yet cancer cells, unlike normal cells, are not dependent on the synthesis of heme itself to survive. Because this dependence on genes encoding these enzymes is present in all cancers and absent in all normal cells, heme intermediates have a universal role in oncogenesis. Importantly, heme overdrive provides an ideal cancer therapeutic target, as it is: 1) cancer universal (i.e., it is present in all cancers), 2) cancer cell essential (i.e., cancer cells require it), and 3) cancer specific (i.e., it is absent in normal cells). A cancer therapy that targets a cancer cell dependency with these three features can be effective, with low toxicity, in a broad range of cancers. Further, the therapy can be inducible hundreds to thousands fold only in cancer cells. In fact, as discussed previously, photodynamic therapy (PDT), which uses ALA—the first committed intermediate in the heme biosynthetic pathway, to induce photosensitizer porphyrins, has historically been used for cancer imaging. PDT effectively demonstrates the safe inducibility of heme-precursor/porphyrin accumulation in humans.

Heme Overdrive Contributes to Oncogenesis

The human heme biosynthesis pathway to producing heme is astonishingly efficient and throughput, however diverse types of cancers required a faulty and seemingly inefficient heme biosynthesis pathway to survive. The inventors believe the accumulation of heme intermediates (e.g., PPIX) in cancer heme overdrive contributes to oncogenesis. The labile heme metabolite PPIX pool, not the bound heme, acts to promote oncogenesis. In response to the cellular milieu, uncommitted and labile heme/intermediate PPIX can bind to specific apoproteins endowing them with signal sensing properties (which may be critical in oncogenesis), such as P53, PGRMC1, Rev-erbA and Rev-erbB[15]. By contrast to these heme-responsive sensors, tightly heme-bound proteins or hemoproteins, such as hemoglobin, typically perform redox or catalytic functions.

Figure 20:
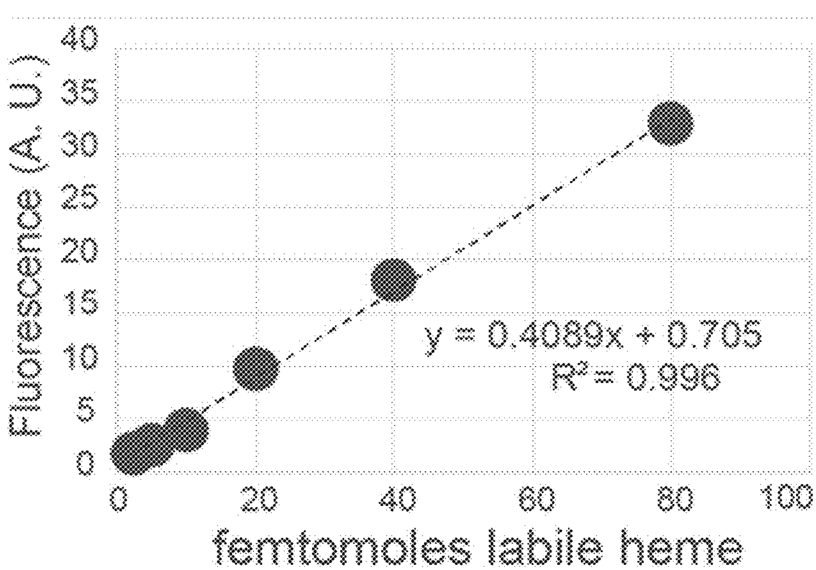
FIG. 20 is an image depicting high resolution labile heme quantification. The assay quantitates labile heme by determining the heme that apo-horseradish peroxidase can access and use to oxidize a chromogenic substrate. The graph is based on heme spiked and un-spiked K562 cell lysates.

There are two pools of heme in cells, bound and labile[15]. The bound form accounts for the bulk of heme in humans. The majority of this heme is tightly bound to proteins to form hemoproteins e.g., hemoglobin and cytochromes. Labile heme, by contrast, is present in low quantities of nano molar ranges in normal cells, but possesses a wide range of signaling roles in e.g., regulating transcription, translation, micro RNA processing, circadian rhythm[15]. As a first step to evaluate whether labile heme/intermediates and bound heme/intermediates contribute distinctly to oncogenesis, the inventors determine and quantify the two forms of heme in various cellular settings, i.e., leukemia cancer cells of K562, pancreatic cancer cell MiaPaCa2 and normal human fibroblasts using the ultra-sensitive (femto mole) heme assays (FIG. 20) for precise labile heme quantification.

Figure 21:
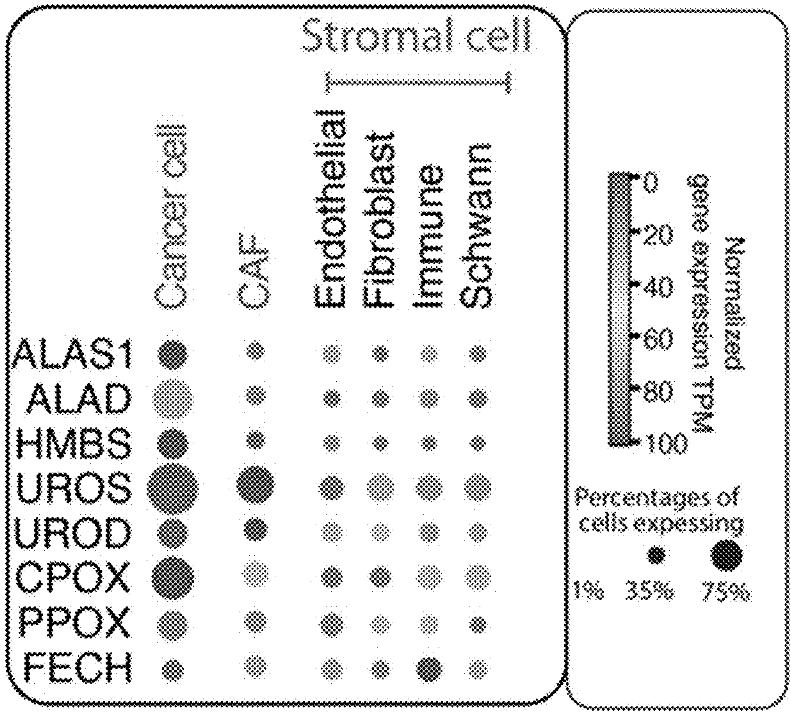
FIG. 21 is an image depicting primary CAFs show heme overdrive. Single cell analysis shows cancers and CAFs have evidence of heme overdrive in pancreatic cancer.

The inventors quantify labile heme vs. total heme in the following conditions: a) control, b) external heme depletion[103], and c) heme overdrive induction with ALA. The inventors quantify total cellular labile heme using the recently developed high sensitivity (nM resolution) labile heme assay that uses peroxidase to oxidize chromogenic substrates (FIG. 21). Additionally, for the detailed biochemical characterization of the heme biosynthesis pathway intermediates (both early and later precursor porphyrins) and total final product (heme), HPLC or ultra-performance liquid chromatography (UPLC) are used along with and well-established clinical protocols extensively used in the diagnoses of porphyria subtypes[104,105] Briefly, a UPLC system equipped with a reverse phase C18 column, a photodiode array detector and a fluorescence detector will be used to determine total heme and protoporphyrin IX (PPIX). Since during sample preparation heme ($Fe^{2+}$-PPIX) is oxidized to hemin ($Fe^{3+}$-PPIX), hemin chloride and PPIX will be used as standards for quantitation. To analyze porphyrin precursors (e.g., uroporphyrin III, coproporphyrin and protoporphyrin IX), the porphyrins and heme are separated on a reverse-phase C18 column (UPCL) and visualized fluorimetrically. Porphyrins (high quality reagents) are commercially available (Frontier Scientific, Logan, UT) and will be used as standards. Each of the porphyrins to be analyzed has well-defined molar absorptivities and $\lambda_{exc}$ and $\lambda_{em}$ maxima for the proposed assay conditions[106], and thus, their quantitation using spectroscopy (fluorescence or UV-visible absorption) is straightforward[107-117]. These studies are conducted by the inventors heme chemistry research group. The results of the experiments involving heme/intermediates depletion vs. porphyrin induction defines the role of labile heme/intermediates vs. total heme in oncogenesis. The inventors expect that external heme depletion stops cancer cell growth but not normal cell growth; and induction sustains cell growth via intermediates accumulation in cancers, in contrast to enhanced end-product synthesis in normal cells.

The inventors determine the epigenome associated with heme overdrive and heme depletion. Heme intermediate (e.g., PPIX) in cancer heme overdrive is linked to epigenetic regulation of essential processes of oncogenesis as supported by previously published work[118] which shows 1) diverse cancer cell lines share a core set of large-scale epigenome changes; 2) pre-implantation embryo epigenomes (the only normal cell supporting heme overdrive) possess striking architectural resemblance with pan-cancer epigenomes (not shown). To uncover the role of heme intermediates (e.g., PPIX) in interactions with cancer epigenomes, the chromatin status is examined, under the following experimental conditions: 1) heme/intermediates depletion by inhibiting the $2^{nd}$ enzyme of the pathway, and 2) heme overdrive with ALA induction in leukemia cell K562 and pancreatic cell line MiaCaPa2. ATAC-seq, histone variant studies, are performed and an additional set of selected epigenetic markers of H3K4me3, H3K9ac, H3K27ac, H3K27me3 and H3K9me3 are included to examine both activated and repressed chromatin regions. As a complementary approach, RNAseq is generated from the same sample set, with identical biomaterial source and experimental conditions, to evaluate the epigenetic changes with respect to cellular transcriptomic changes. For epigenome data generation, a total of half million cells is used for each marker, and cell nuclei are harvested and prepared for NextSe500 sequencing. For the epigenetic peak calling and analysis, the R package chromVAR[119], CHiPseeker[120] and DESeq2[121] is used. The significantly differential peak signals are assigned to the nearest genes based on the starting sites. The inventors expect that depletion and accumulation of heme intermediates lead to opposing epigenome rewiring patterns, with the presence of these intermediate metabolites linked to epigenetic changes that are associated with oncogenesis.

Figure 13G:
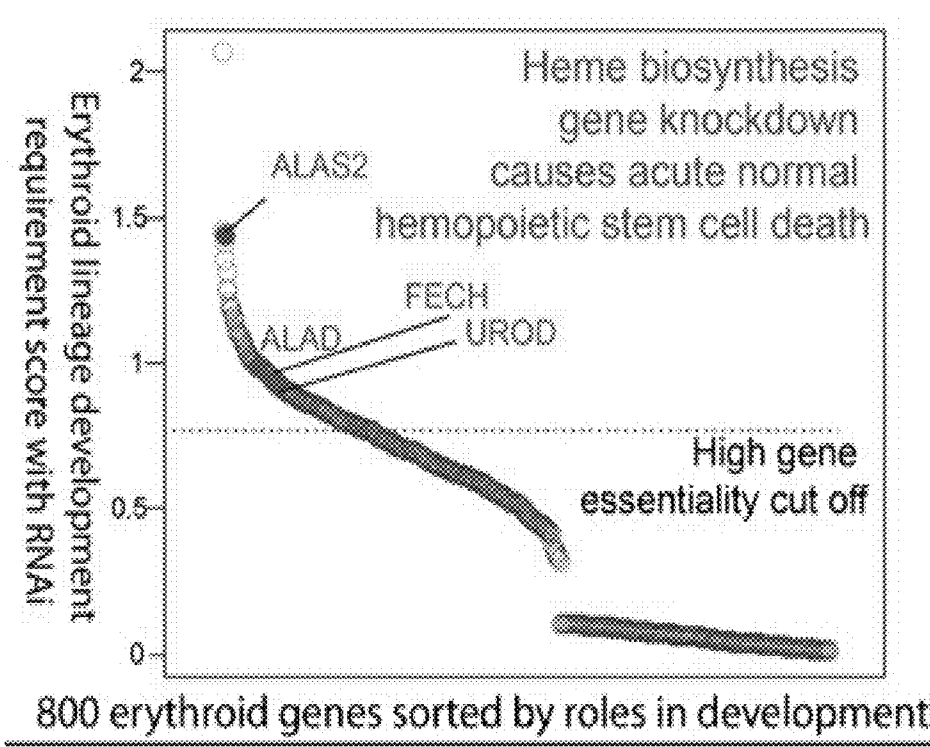
FIG. 13G is an image depicting normal human bone marrow stem cells suffer cell death upon shRNA knock down of ALAS2, ALAD, UROD, and FECH.

In Example 1, the inventors verified that cancer cells do not need to synthesize their own heme (FIG. 13D-E). CRISPR knock-out (KO) of the genes encoding FECH and ALAS2 were generated in K562 cells (FIG. 13D-E). Under a heme homeostasis model, a FECH KO mutant should not survive, because it is a single copy gene in humans and with no known functional substitute. Indeed, a prior human stem cell KD experiment showed cell death upon FECH KD[63]. However, under heme overdrive, cancers rely on heme trafficking and require porphyrin intermediates, and the final step of heme synthesis is not essential. Indeed, the FECH KO has normal growth (FIG. 13E) and no apparent abnormality under standard culture conditions, confirming the previous gene essentiality screen data. The dispensability of ALAS and FECH is in sharp contrast with normal stem cell's requirement for ALAS and FECH (FIG. 13G). The previously generated shRNA knock down results[63] from human bone marrow hemopoietic stem cells demonstrates normal cell dependency on all the heme biosynthesis genes tested.

To further explore the mechanisms of heme overdrive, new cell KO mutants are generated of the major driver genes that were identified, i.e., genes for the enzymes that catalyze the third and fifth steps of the heme biosynthetic pathway, hydroxymethylbilane synthase (HMBS) and UROD, respectively. Attenuation or elimination of these driver proteins diminishes cancer survival related to heme biosynthesis. These mutants are generated and characterized with methods presented in Example 1. Immunoblotting to confirm protein loss and sequencing to confirm deleterious editing is performed. The findings are confirmed in additional cells lines, such as HEL or TF1 cells, and expanded to cell lines representing solid tumors such as human pancreatic cancer cell lines MiaPaCa2, Panc0203 and Panc1. To directly evaluate the oncogenic potential of metabolites associated with heme overdrive, and to investigate the effect of deregulation of the heme biosynthetic pathway on oncogenic phenotypes, the intermediate step HMBS enzyme in primary fibroblasts is over-expressed. The effect of overexpression of HMBS is determined with respect to changes in cell proliferation rates and transcriptomic analysis is performed to detect dedifferentiation marker expressions[122], and canonical genes associated with oncogenesis[123]. These experiments determine the role of the drivers of heme overdrive in cancer cell survival, and the oncogenic potential of heme overdrive. The inventors expect genetic disruption of heme intermediates generation hampers cancer cell growth, and genetically induced heme intermediates accumulation in normal cells leads to de-differentiation process.

Tumor Microenvironment (TME) Supports Heme Overdrive in Tumor Cells

Cancer cells do not exist in isolation. The flux aspect of heme overdrive (i.e., enhanced heme and intermediates trafficking), is evidenced by 1) enhanced expression of heme trafficking genes in tumors[124-127], and 2) hemoprotein gene essentiality despite that cancer cells survive without the complete biosynthesis pathway (FIG. 5). It is remarkable that even cancers do not need to synthesize their own heme to grow (FIGS. 5 and 13), the heme/intermediates export gene is elevated across diverse tumors[124-127], suggesting exporting activities are of essential function. The feature of heme/intermediates flux necessitates a specialized cancer microenvironment for metabolite trafficking. However, there is currently no understanding of either the source or the fate of trafficked heme metabolites in the tumor microenvironment (TME). Heme trafficking is under strict control in the normal marrow environment due to the potential toxicity of heme accumulations[128-130]. In cancers, heme overdrive is likely fostered by the specific cancer microenvironment optimized for heme transport and heme detoxification.

As noted in Example 1, to study heme overdrive in primary patient tissues, single-cell RNAseq on biopsies from acute myeloid leukemia (AML) patients (n=3) were performed. For each patient, around 2000 single-cell transcriptomes were obtained, and cells of various differentiation stages and cell types were analyzed. Interestingly, in two independently generated patient biopsy samples, only a minority of cells, about 5-10% of total cells, were identified as cancer progenitors (FIG. 14B). They bore hybrid features of both mature, e.g., hemoglobin production, and immature, e.g., proliferation, cells (not shown). The cancer progenitor cells exhibited differential expression of heme biosynthetic enzymes, with notable elevated gene expression for enzymes that catalyze the intermediate steps of heme biosynthesis, e.g., HMBS and UROD (FIG. 14G). The results show that these cancer progenitor cells have heme overdrive, and are consistent with ex vivo ALA heme induction studies in AML transplant studies[60]. The inventors extended the single-cell analysis to solid tumors, and identified similar overexpression patterns for the genes encoding the enzymes for the intermediate steps of the heme biosynthetic pathway (i.e., HMBS, UROD and CPOX) of in single pancreatic cancer cells[131] (FIG. 14G).

To study cancer cells and TME at single cell resolution, the inventors used single-cell cancer transcriptomes generated from pancreatic cancer[131], and analyzed for heme biosynthesis and trafficking in diverse cell populations present in the tumor. HMBS and UROS were the most upregulated heme biosynthesis genes in tumor cells and CAFs (FIG. 21). Cancer cells and primary tumor cancer-associated fibroblasts (CAFs) exhibit features of heme overdrive, consistent with the abnormal endogenous PPIX accumulation upon ALA administration in cancer cells compared to normal cells[60]. By contrast, major groups of stromal and immune cell populations do not show evidence of imbalanced heme biosynthesis or heme trafficking with these cell populations (FIG. 21).

Heme overdrive in TME implies that targeting heme overdrive kills both cancer cells and CAFs. The inventors examine isolated solid tumor derived CAFs in pancreatic cancers. The isolated primary CAFs and matching normal fibroblast pairs will be purchased (BioreclamationIVT), and for each CAF vs. normal pair, the inventors i) conduct ALA induction experiments with PPIX quantifications, ii) perform transcriptomics on cell populations with different PPIX levels, to reveal the cellular expression profiles of heme metabolic enzymes, and iii) quantify extracellular (media) vs. intracellular PPIX (cellular) levels at nanomolar resolution.

For liquid tumors, CAFs are currently not clearly defined[132]. To identify the relevant stromal cells, the inventors perform unbiased single cell RNAseq on the bone marrow-derived cell populations and identify all tumor associated bone marrow derived cell populations, based on surface markers and aberrant metabolic pathways. The inventors perform flow cytometry-based enrichment using the molecular profiles (cell surface markers, e.g., CD163 for macrophages, CD71 for erythroid, CD143 for endothelial cells, CD87/CD44 for fibroblasts) to isolate the cells. Subsequently, the inventors conduct single cell RNAseq on the fractionated samples. For the single cell RNAseq (10× Genomics), similar methods to those used to obtain the data shown in FIG. 14 are used. For quality control, each cell must have at least 200,000 reads mapped to references, and less than 50% mapped to the External RNA Controls. The single-cell developmental lineage is reconstructed from individual cell transcriptomes. Critical heme overdrive-related enzymes and transporters, e.g., major drivers of heme overdrive and elevated glycolysis, are monitored to assess the metabolic status of the cancer progenitor and stromal cells. AML samples (n=3) with expanded erythroid progenitors are studied, and tumor associated cell populations are identified. The inventors expect to identify both the malignant progenitors, and among other cancer associated stromal cell populations in AML TMEs.

The inventors study the TME and its association with heme/intermediates flux with a pancreatic cancer PDO model[133-137] that preserves human TME from pancreatic patients. A prior study[138] showed surgically removed gliomas exhibiting PPIX accumulations after ALA induction which correlated with WHO tumor grades, as did Ki-67 staining. The inventors use a mouse PDX model to emulate the same process, and to examine PPIX production, transcriptome heterogeneities, metabolites partitioning with single cell multi-omics. The inventors induce PPIX accumulation with ALA induction in pancreatic cancer KRAS G12D and/or KRAS G12V PDO models representing high tumor grades. After 24 hours, the tumor is cryopreserved and tissue sections are prepared, for a) fluorometric quantification of in situ PPIX; b) spatial single cell transcriptomics; and c) spatial global metabolites quantification with matrix-assisted laser desorption/ionization time-of-flight (MALDI-TOF) mass spectrometry imaging[139]. Integration of the information of heme production, transcriptomics and core set of metabolites pinpoints the cell populations exhibiting heme overdrive and metabolite production profiles. As a complementary approach to the PDX TME experiment, the inventors use dissociated solid tumor tissues for heme quantifications and single cell RNAseq. The inventors obtain patient-derived, dissociated pancreatic solid tumor tissues (n=2) (BioreclamationIVT), to perform experiments of a) ALA-induction and PPIX quantification, b) unbiased single-cell RNAseq. The inventors expect to find consistent metabolites trafficking patterns in distinct tumors. This approach uses well-established protocols, albeit the physical locations of the single cell population are reconstructed computationally based on published methods[140,141].

Bait-and-Kill Strategy to Target Heme Overdrive in Cancer Cells

The characteristics of heme overdrive provide targets for interventions that offer cancer universality, specificity and essentiality. The inventors present three cancer cell targeting strategies based on the biochemical and biophysical vulnerabilities intrinsic to mechanisms of cancer heme overdrive.

Cancer cells are susceptible to “baiting” in which rapid accumulation of heme precursor porphyrin metabolites (e.g. PPIX) is induced, due to the imbalanced heme biosynthesis enzymatic activities. For ‘bait’, cells readily take up the heme precursor ALA and bypass the first and rate-limiting step of porphyrin biosynthesis catalyzed by ALAS1. As an exogenously provided precursor, ALA has multiple import routes into the cell. The induction with ALA to induce porphyrin accumulation in cancers has been clinically and safely used in PDT for decades[66, 142-146]. As noted in Example 1, the inventors designed a two-step process to engineer cancer cell metabolic death: first, ‘bait’ with ALA to induce PPIX accumulation to up to a few hundred-to-thousand-fold higher concentration as compared to control cells, and second, ‘kill’ with a compound that exploits the metabolic oxidative stress of porphyrin accumulation.

As noted in Example 1, to exploit the metabolic stress of porphyrin accumulation, the inventors treated the human leukemia HEL cell line with a range of concentrations of RSL3. First, ALA pre-treatment leads to accumulations of intermediates PPIX that can cause membrane lipid peroxidation. Cancer cells likely have elevated dependence on the antioxidant enzyme glutathione peroxidase 4 (GPX4), which is a phospholipid hydroperoxidase that protects cells against peroxidation. Subsequently, inhibition of GPX4 with RSL3 induces acute redox stress and cell death. Pretreatment of HEL cells with ALA increased RSL3 sensitivity at least 1000-fold (FIG. 17D). In contrast, ALA pretreatment did not sensitize cells to the heat shock protein inhibitor ganetespib suggesting ALA is not a general sensitizer to induction of cell death (FIG. 17D). The inventors also performed the same bait-and-kill approach in primary human lung fibroblasts and found no increased sensitivity to RSL3 at either 24 hours or 48 hours (FIG. 18). This non-toxic effect in normal cells stands in stark contrast with the sub-nM range of IC50 of drugs with similar bait-and-kill strategies in various cancer cell lines (e.g., HEL, K562, K562-FECH-KO, K562-ALAS2-KO, BAF3-Jak2mt). These experiments show cell growth and viability of non-cancer cells are not impaired by the bait and kill strategy, in contrast to cancer cell lines.

The inventors perform RNA-seq studies on each of the below candidate bait and kill strategies (control, ALA-treated, RSL3-treated/antimalarial-treated, and the combination of the two) to begin to evaluate if cell death by bait and kill involves unique transcriptomic changes that may shed light on the cellular/mechanistic effects of bait and kill. The inventors also perform MALDI-TOF cell-based assays to assess metabolic changes and gain mechanistic insight into effects of the bait and kill strategies[147, 148]. These experiments highlight potential mechanisms by which a bait and kill approach based on heme overdrive can be refined and improved, such as delineating the most vulnerable cancer cellular component, perhaps by utilizing other targeted therapeutics.

The inventors also assess the most promising candidate bait and kill strategies in 1) AML mice model[149, 150], 2) pancreatic cancer KRAS G12D and/or KRAS G12V PDO models[133-137] for in vivo evaluation. This includes 4 treatment arms: untreated (vehicle) and treatment with ALA, the candidate ferroptosis inducer, and the combination of ALA and ferroptosis inducer (the bait and kill test arm of the experiments). Tumor burden/size is measured over time as described previously. Following treatment tumors are examined for PPIX accumulation (PPIX fluorescence) and immunohistochemical staining for cell proliferation markers (e.g., Ki-67)[151], glutathione levels[152] and lipid peroxidation[153].

Attacking Defense Strategy

A first strategy of the bait and kill method is the "attacking defense" based strategy. Because heme overdrive leads to accumulation of reactive heme precursors (e.g., PPIX) with heightened redox stress[98, 154], cellular defense systems such as the GPX4 glutathione antioxidant system are antagonized. The ferroptosis inducer RSL3 has shown drastically enhanced cytotoxic effects against HEL AML cells following the induction of heme intermediates with ALA, which may be due to the imbalanced heme metabolism inherent to cancer heme overdrive. The inventors assess a panel of compounds to exacerbate cellular redox stress that sensitize cells to ferroptosis. These compounds include approaches to attack glutathione dependent and independent antioxidant systems including erastin (which inhibits the import of cystine, a precursor to glutathione synthesis, and thus erastin decreases intracellular glutathione levels, and exacerbates glutathione supply stress for counteracting heme intermediate PPIX buildup), glutathione peroxidase 4 (GPX4) inhibitors RSL3 and ML 210 (which inhibits GPX4, thus leading to elevated cellular redox stress and aggravated PPIX induced oxidation), and iFSP1 (which inhibits the ferroptosis suppressor protein I, a glutathione-independent protector against lipid peroxidation, thus leading to elevated lipid redox stress, and enhancing PPIX lipid oxidation effect)[155]. The unique aspect of cancer universality of heme overdrive suggests this aberrant cancer metabolic process could be a target for therapy in a wide variety of cancer types. Studies are expanded in the two cancer cell models, i.e., AML and pancreatic cancer, previously used in Example 1. Concentration-response studies are performed using compounds in the absence and presence of ALA treatment to induce the accumulation of heme precursor metabolites such as PPIX. Relative cell viability is assessed, and cytosolic and lipid peroxidation is monitored by flow cytometry using the fluorescent probes $H_2$DCFDA and C11-BODIPY, and ferroptosis is confirmed using deferoxamine (DFO), which chelates intracellular iron, preventing ferroptosis, as described[156]. Normal, non-transformed cells (e.g., healthy PBMCs, CD34+ cells, pancreatic cells) are used as controls to confirm the sensitization to ferroptosis induction upon induction of porphyrin (heme precursor) accumulation by ALA treatment is specific to cancer cells. Promising results and healthy control experiments are confirmed in replicated experiments (n>=3). These experiments ascertain the extent to which enhancing redox stress with ALA pretreatment sensitizes cancer cells to induction of cell death via ferroptosis.

Trojan Horse Strategy

External blue light has been used to excite accumulation of the heme intermediate PPIX to generate toxic free radicals for killing cancer cells[157]. The inventors substitute an external light source with intracellular chemiluminescence or radionuclide generated radiation, as an internal source of light, to activate intracellular heme intermediates PPIX phototoxicity. These activators can be delivered via heightened cancer uptake of glucose or glutamine, which is widely used in cancer imaging. This strategy takes advantage of both the Warburg effect and heme overdrive, as both are universal cancer metabolic processes: glucose-uptake is used for cancer imaging and PPIX is used in surgical resurrections. The standard cancer imaging agent $^{18}$F-fluorodeoxyglucose ($^{18}$F-FDG) is able to activate a photosensitizer toxicity via emission of Cherenkov light[158] (which is blue) and causes cancer cell killing in a metastatic myeloma mouse model[59], due to phototoxicity of PPIX. Agents to be tested include: i) radionuclides such as $^{18}$F-FDG, and ii) radiolabeled glutamine 4-$^{18}$F-(2S,4R)-fluoroglutamine ($^{18}$F-FGln), which is taken up by tumor cells selectively over non-cancerous normal tissue in vivo[160], and iii) chemiluminescence with luminol, which induces light in the presence of $H_2O_2$, and is used for deep tissue imaging[161] and has demonstrated cytotoxic effects in combination with hematoporphyrin treated leukemia cells[162]. The internal light generated by $^{18}$F-FDG, $^{18}$F-FGln and Luminol can activate PPIX and generate free radicals to kill cancers. Experiments are performed as described in the "attacking defense" strategy above and results confirmed in replicated experiments (n>=3). Normal, non-transformed cells (e.g., healthy PBMCs, CD34+ cells, pancreatic cells) are used as controls to confirm cancer cell selectivity.

Lethal Heme Adduct Strategy

Heme molecules (PPIX and heme) can be directly activated by chemical agents to unleash radical damage[163, 164]. Heme detoxification is essential for survival of malarial parasites in human red blood cells, and a range of antimalarial compounds exploit heme toxicity to kill these parasites[163, 164]. The inventors use compounds whose mode of action involves heme activation, i.e., free heme or accumulating PPIX forming adducts with antimalarials to generate free radicals to kill cells. In an in vivo mouse model, the antimalarial compound dihydroartemisinin can sensitize cancer cells to ferroptosis and mediate significant tumor reductions[165]. Agents to be tested include chloroquine and artemisinin derivatives such as dihydroartemisinin. Experiments will be performed as in the "attacking defense" strategy and results confirmed in replicated experiments (n>=3). Normal, non-transformed cells are used to confirm cancer selectivity.

To further enhance the efficacy, a combination approach of ferroptosis inducers can be considered in testing the effect of the bait and kill strategies. Cancer heme overdrive does not appear specific to certain cancers, but cells with different driving mutations may respond differently to the above strategies. The studies can be expanded to evaluate the role of genetic drivers, e.g., HMBS, in the response of cancer cells to the heme overdrive targeting strategies. Other in vivo as well as solid tumor organoid models can be used to further evaluate the bait and kill strategies.

Conclusion

The inventors are the first to describe how diverse cancers become addicted to a seemingly inefficient heme biosynthetic pathway for tumor survival and uncover a potential fundamental role of heme precursor intermediates in promoting oncogenesis. The inventors are also the first to describe how tumor microenvironments contribute to cancer heme overdrive, thus providing unique potential for targeting both cancers and their microenvironment. The inventors utilize novel strategies to target heme overdrive, by exploiting distinct biochemical and biophysical vulnerabilities intrinsic to the mechanisms of this potential metabolic vulnerability that is present in all cancer types. The inventors approach harnesses the large amount of clinical PDT experience of using ALA as inducer of protoporphyrin (a photosensitizer) production in diverse cancers and taps into the power of the rapidly developing field of tumor medical imaging to deliver non-toxic imaging chemiluminescent and radionuclide as precision in situ 'kill' agents in a spatiotemporal-controlled manner that is defined by cancer cells themselves.

Example 3—Heme Overdrive in Lung Cancer

Lung cancer is the leading cause of cancer death globally; and cancer metastasis is responsible for most of the mortalities. Chemotherapies remain one of the principal treatments combating lung cancer[167]. However, these therapies face the challenges of 1) limited efficacy particularly in end-stage cancer, 2) and substantial drug-induced toxicity in patients[167]. Immunotherapies and genomics-based therapies[167] are the other options offering targeted, better-tolerated treatment plans, yet they are still of limited use for different types and stages of lung cancers. Thus, novel approaches are needed to fight this deadly disease.

As noted in the previous examples, cancer cells use imbalanced heme metabolic pathways ("heme overdrive") and do not need to synthesize their own heme end-product, but must rely on the pathway mid-steps to accumulate heme intermediates. These heme intermediates have a universal role for oncogenesis and heme overdrive provides an ideal anti-cancer target, given that it is: 1) universal (i.e., present in all cancers), 2) essential (i.e., cancer cells require it), and 3) specific (i.e., absent in normal cells). Heme overdrive is absent in all normal human cells (except pre-implantation human embryos), which offers elegant approaches to only kill cancer cells. With respect to lung cancer, the inventors have shown that heme overdrive is present in 1) metastatic lung cancer cell lines, 2) the lung cancer tumor microenvironment (TME), 3) end-stage solid tumors, and 4) single-cell lung cancer progenitor cells. By contrast, heme overdrive was absent in normal cells, including match normal tissue from the same patient. The inventors propose a novel onco-metabolic drug therapy to kill both (1) lung cancer cells and (2) tumor-supportive microenvironment (TME) cells, with minimal toxicity to normal cells. (FIG. 22A).

Heme Overdrive is Absent in Normal Cells

As noted in Example 1, the inventors compared heme biosynthesis in diverse types of non-cancerous cells, i.e., normal differentiated cells, replicating fibroblasts, human primary hepatocytes, and human primary hematopoietic stem cells. The inventors looked for evidence of heme overdrive, defined by a non-homeostatic, imbalanced heme biosynthetic pathways and heightened accumulation of heme pathway intermediates. It was found that heme overdrive is absent in normal differentiated cells and somatic stem cells. For example, normal peripheral blood mononuclear cells (PBMCs) do not accumulate heme intermediates even upon ALA-induction. Colon cancer cells incubated with ALA to induce protoporphyrin IX (PPIX) production do accumulate PPIX, while no significant PPIX accumulation is observed in replicating human colon-derived fibroblasts (stromal cells) previously incubated with ALA. Increased HMBS activity in colon cancer cells relative to stromal cells is consistent with an accumulation of heme intermediates, including PPIX. Further, normal, metabolically active, primary hepatocytes do not accumulate porphyrins as indicated by the absence of the PPIX fluorescence (FIG. 22C). By contrast, >99% of liver cancer cells produced and accrued PPIX upon induction with ALA, demonstrating a canonical feature of heme overdrive (FIG. 22C).

The inventors also validated that primary human lung fibroblasts lack heme overdrive, the inventors showed >99% tested normal lung cells are negative in PPIX accumulation after ALA induction (FIG. 22D). The inventors studied the data for both 969 lung cancer tumors and matching normal tissue and discovered evidence of an imbalanced heme biosynthesis pathway, and enhanced trafficking, which are canonical features of heme overdrive. The ALAD gene (encoding the enzyme for the second step in the heme biosynthetic pathway) is down-regulated in patient tumors, while the third step HMBS gene and the heme-metabolite trafficking gene FLVCR1 are upregulated in patient tumors, as compared to normal lung tissues which lacks these features of heme overdrive (FIG. 22E). The same analysis indicates cell differentiation and cell proliferation genes to be down and upregulated, respectively, in tumor samples (FIG. 22E).

Metastatic Cancer Cell Lines Display Heme Overdrive

Figure 23:
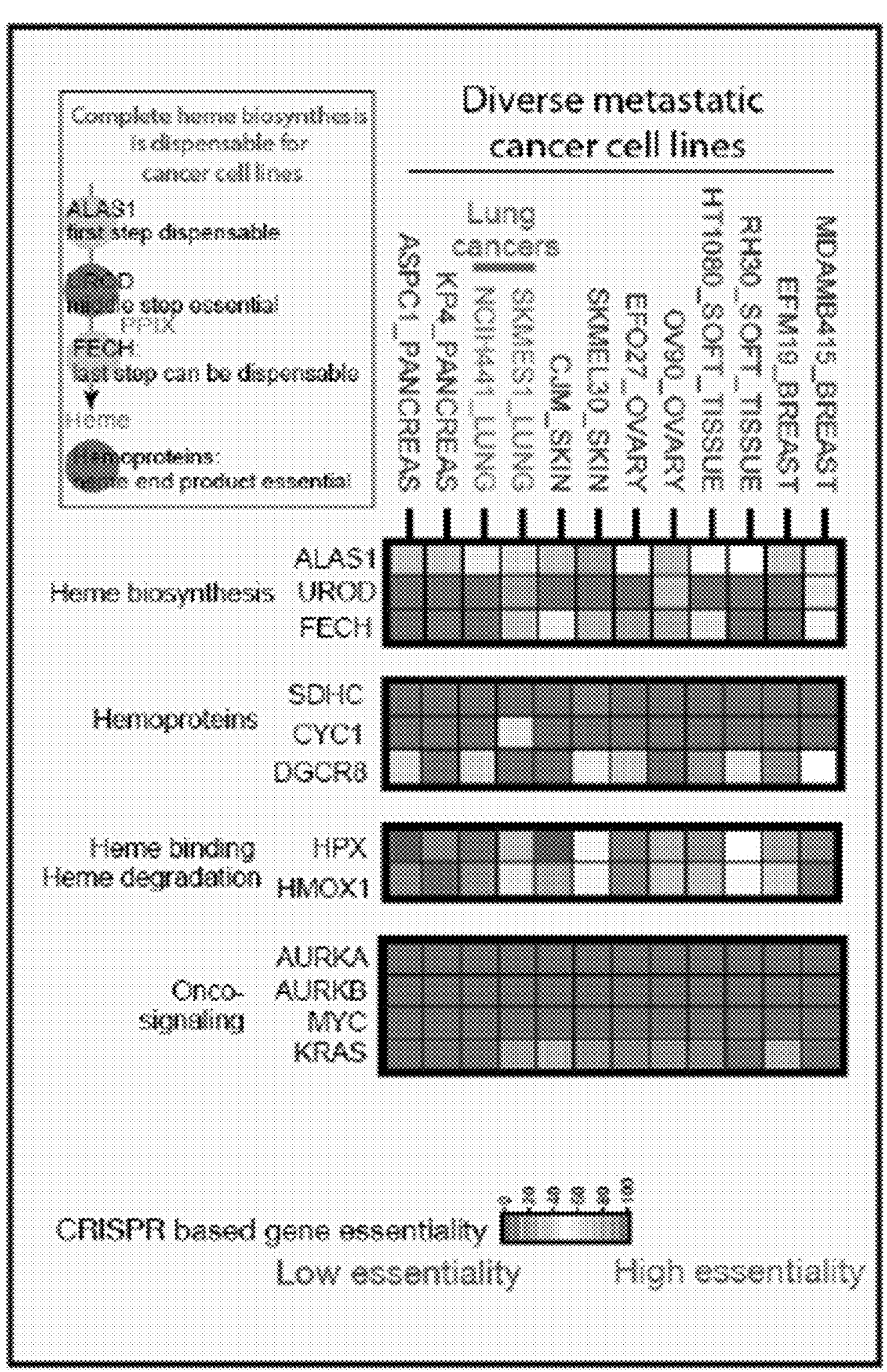
FIG. 23 is an image depicting heme metabolism dependence in diverse metastatic types of cancer. The data for the CRISPR/Cas9-gene targeting of the genome-scale loss-of-function screens in a set of cancer cell lines were retrieved from DepMap. The columns refer to different cancer cell lines, while the rows refer to specific genes. Note the differences between the loss-of-function scores for specific proteins associated with heme biosynthesis (ALAS1, UROD and FECH) in this panel of metastatic cancer cell lines.

As noted in Example 1, the initial data analyses of genome-scale CRISPR/Cas9-gene loss-of-function from the publicly available project DepMap screens of cell lines derived from metastatic cancers[38] indicated that cancer cells depend on some, but not all, of the genes that encode enzymes in the heme biosynthetic pathway (FIGS. 23 and 13). Significantly, these metastatic cancers developed dependencies on heme metabolism-related proteins, such as uroporphyrinogen III decarboxylase (UROD), the enzyme that catalyzes the fifth step in the heme biosynthetic pathway (FIGS. 23 and 13). These cancers also depend on a set of hemoproteins, such as cytochrome c-1 (CYC1), succinate dehydrogenase complex subunit C (SDHC) for cellular respiration, and DGCR8 for microRNA biogenesis[39], each of which uses heme as a co-factor (FIGS. 23 and 13). Unexpectedly, the FECH gene, encoding ferrochelatase that catalyzes the final critical step of heme biosynthesis, is dispensable in several cancer cell lines, suggesting that cancer cell lines are capable of bypassing endogenous biosynthesis of heme in vitro, yet are still dependent on genes encoding enzymes that mediate intermediate steps of heme biosynthesis (FIG. 23). This initial analysis suggests that cancer is dependent on imbalanced heme metabolism. Notably, metastatic lung cancer cell lines (n=10), e.g., SKMES1 and NCIH441, exhibit this imbalanced heme metabolism based on CRISPR loss-of-function analysis (FIG. 23).

As detailed in the previous examples, to better understand the molecular and genetic mechanisms underlying the cancer dependency on heme metabolism, gene essentiality was determined from genome-scale CRISPR/Cas9 loss-of-function screens human lung cancer cell lines[38,42]. Then, the inventors focused on the gene dependencies associated with the eight enzymatic steps of the heme biosynthetic pathway by computing the respective pan-cancer essentiality scores, similar to the lethality scores used in the development of a cancer dependency map (DepMap)[22,23]. Gene essentiality score values lower than zero indicate decreased cell growth/viability with loss of gene X, and hence the lower the X gene essentiality score, the more dependent cells are on the X gene. Consistent with recent cross-platform studies[40,47], over 2000 genes were defined as pan-cancer essential, based on the distribution of their essentiality scores. The gene essentiality scores were confirmed by using the same method on the total DepMap collection (DepMap release 21Q3) of over 1000 cell lines (Pearson's $R>0.9$, $p<0.001$).

Figure 24:
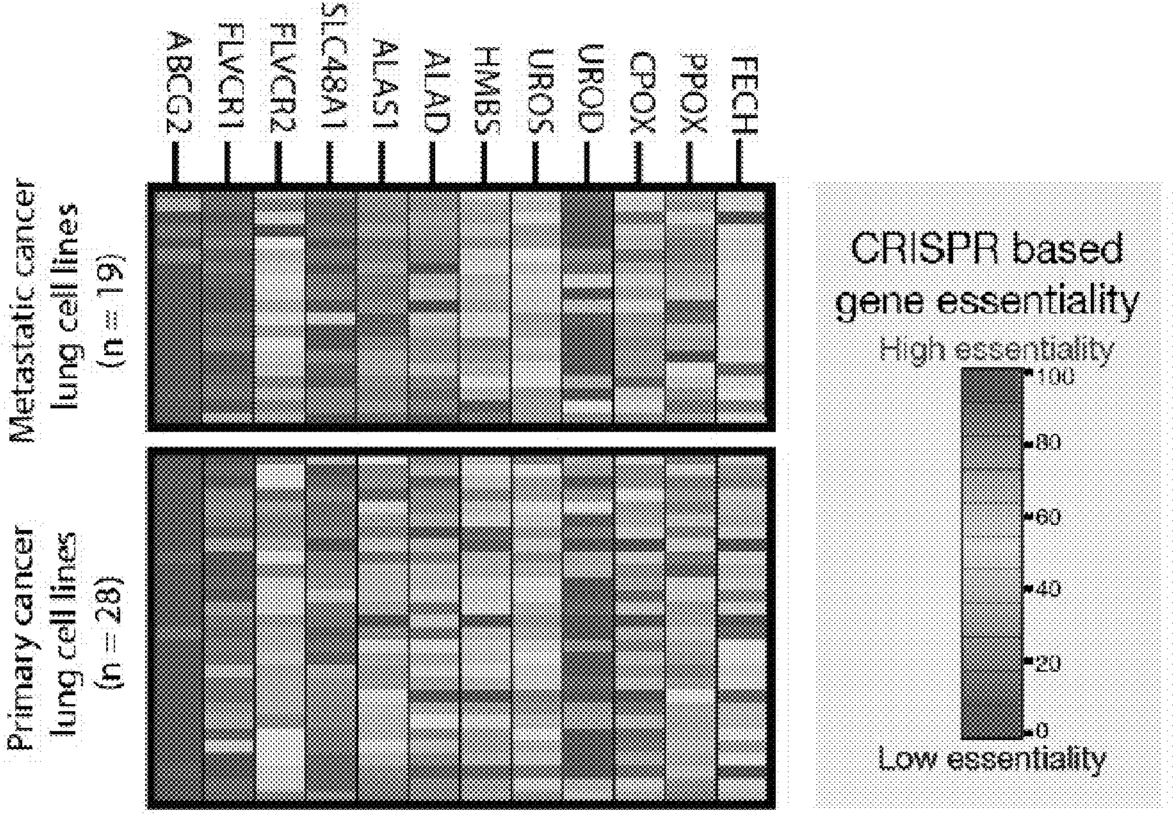
FIG. 24 is an image depicting CRISPR/Cas9 gene targeting and inferred gene essentiality in lung cancer cells exemplify heme overdrive. Whole genome loss-of-function growth phenotypes show that most cancer cells only require a partial heme biosynthetic pathway to survive. Gene essentiality is estimated from gene X dependency inferred from CRISPR/Cas9 gRNA gene X knockout. Low and high cell viability with deletion of gene X indicate that the cancer cells have a high and low dependence on gene X for survival, respectively. Thus, the lowest and highest gene essentiality values are associated with the least and most profound dependence of the cells on the loss of gene Xt, respectively. The UROD gene for the fifth enzyme of the pathway has the highest essentiality in all types of cancers, while genes encoding other enzymes are dispensable in many cancer cell lines. Each of the rows represents a distinct cancer cell line from primary and metastatic tumors. [ABCG2, ATP-binding cassette (ABC) transporter subfamily G, member 2; ALAD, ALA dehydratase (aka porphobilinogen synthase); ALAS1, 5-aminolevulinate synthase 1; CPOX, coproporphyrinogen oxidase; FECH, ferrochelatase; FLVCR, feline leukemia virus subgroup C receptor family; HMBS, hydroxymethylbilane synthase; PPOX, protoporphyrinogen oxidase; SLC48A1, solute carrier family 48, member 1, a.k.a heme transporter HRG1; UROD, uroporphyrinogen III decarboxylase; UROS, uroporphyrinogen III synthase]

Strikingly, instead of finding the expected complete and balanced heme biosynthetic pathway characteristic of normal cells, the inventors discovered that the survival of cancer cells depends on the various steps of the heme biosynthetic pathway in a "non-balanced" manner (FIG. 24). In both primary and metastatic lung cancer cell lines, the tumor cells particularly rely on the intermediate enzymatic steps of heme biosynthesis, as assessed by loss of cellular viability upon CRISPR/Cas9-mediated gene ablation in whole genome loss-of-function screens, the pan-cancer gene essentiality is the highest for the genes encoding the enzymes responsible for the fifth and sixth steps of the pathway, UROD and coproporphyrinogen III oxidase (CPOX), respectively. This result was notably surprising, as the genes for the ALAS isoforms, which catalyze the initial and rate-limiting step in the pathway, and the gene for FECH, the final enzyme in the pathway that catalyzes heme production, had lower essentiality values and were dispensable in several cancers. Though the heme biosynthesis genetic dependences of the set of human lung cancer vary, the estimated patterns of essentiality across the cancer lines clearly revealed a range of heme and heme precursor requirements. These results indicate an "unbalanced" nature of heme biosynthesis in cancer cells, with many cancer cells surviving without functional first and terminal enzymatic steps but depending on the intermediate steps. The gene essentiality analysis also highlighted the importance of heme trafficking (e.g., heme importer FLVCR2) and key hemoproteins (e.g., CYC1) in cancer cells in vitro survival (FIGS. 23 and 24).

As noted in Example 1, chronic myeloid leukemia K562 cells were modified with CRISPR/Cas9-mediated knockout (KO) of the genes encoding FECH and ALAS2, the erythroid ALAS isoform (FIG. 13D). Under a heme homeostasis model, a cell line without FECH should not survive, because FECH is a single copy gene in humans with no functional substitute[3]. Indeed, knockdown (KD) of FECH in human stem cells led to cell death[63]. However, under heme overdrive conditions, cancer cells rely on heme trafficking and are addicted to the porphyrin intermediates, and thus do not depend on the final step of heme biosynthesis for survival as shown by K562 cells with the FECH edited out (K562-FECH KO) had normal growth under standard culture conditions (FIG. 13E). The unimpeded growth of the K562-FECH KO cells presumably indicates that at least some cancer cell lines can metabolically function as heme auxotrophs.

Heme Overdrive Contributes to In Vivo Tumorigenesis and Establishing TME

As noted in Example 1, in examining loss of function and metabolic essentiality data from pancreatic and lung cancer models, it was found that most metabolic gene essentialities were similar between the in vitro and in vivo settings, with the exception of the heightened requirement of the intermediate steps of heme biosynthesis in vivo (FIG. 9A). Strikingly, out of the ~2900 examined metabolic genes, the genetic dependencies of both murine pancreatic and lung cancers to grow in vivo were only increased for genes that encode heme metabolic enzymes responsible for the intermediate biosynthesis steps (HMBS, UROS, CPOX, and PPOX) (FIG. 9A,B). The essentiality of either ALAS or FECH, which encode for the first and terminal enzymes of the heme biosynthesis pathway, respectively, did not differ significantly between the in vivo murine cancer models. The analysis revealed that aberrant heme metabolic requirement has increased importance in vivo for cancer cell survival, suggesting potential crosstalk of tumor cells and their TME with respect to aberrant heme metabolism. Furthermore, this requirement is conserved in cancer, as the increased in vivo essentiality of the mid-step heme biosynthesis genes (HMBS, UROS, CPOX, and PPOX) is independent of tumor origin in pancreatic and lung cancers (FIG. 9A).

Essential Heme Intermediate Function

Figure 25:
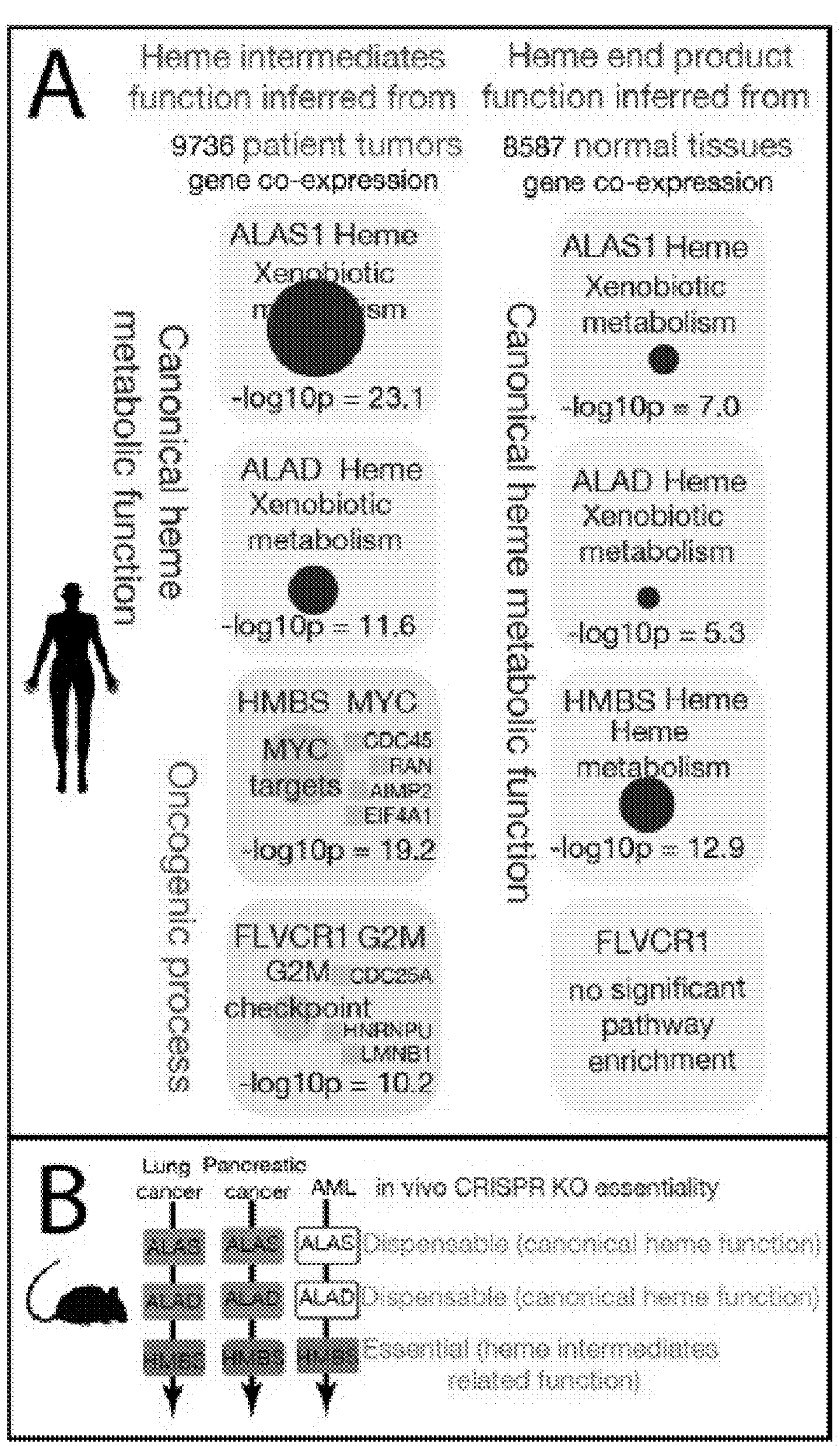
FIG. 25A-B are a series of images depicting essential heme intermediate function inferred from ~10,000 patient tumor gene expression and in vivo CRISPR loss-of-function data in mice. A. Heme intermediates' function is inferred from gene co-expression patterns from 9736 patients with different major types of cancers from TCGA. The genes for the first and second enzymes of the heme biosynthetic pathway, ALAS1 and ALAD, co-express with other heme metabolism related genes in tumors, while the gene for the third enzyme of the pathway, HMBS, and the gene for the heme export gene FLVCR1 coexpress with genes functioning in oncogenic processes. The pan-cancer upregulation of HMBS compared to that of ALAD likely leads to heme intermediates accumulation responsible for the pattern of only mid-step pathway genes linking to oncogenic processes. By contrast, in normal matching human tissues, all heme biosynthesis genes co-express with other heme metabolism genes. −log 10P indicates the significance of the pathway enrichment. All listed pathways are highly significant ($p<0.0001$) B. The first two enzymatic steps of the heme biosynthesis pathway are dispensable, while the third one catalyzed by HMBS is essential as assessed from in vivo animal CRISPR loss-of-function studies. In AML model, the essentiality of the genes for the first enzymatic steps of the pathway cell line was not sufficiently high to be selected for in vivo experiments in the study.

The analysis of CRISPR loss-of-function study in vitro and in vivo, showed that heme intermediates, rather than the end-product heme are obligatory metabolites for cancer cells. However, these heme intermediates have no known biological function. To gain initial insight into the biological function of heme intermediates, the inventors investigated 9736 patient tumors for functional correlation by co-expression analysis and discovered strikingly contrasting functions of heme biosynthesis genes in cancer cells vs. normal tissues[43,45] by gene co-expression analysis. The first 100 most significantly co-expressed genes from the whole genome across all 9736 cancers were used for pathway analysis (p value $<0.001$). In tumors, the genes for the first and second enzymes of the housekeeping heme biosynthetic pathway, ALAS1 and ALAD, co-express with other heme metabolism-related genes in tumors, while the gene for the third enzyme of the pathway, HMBS, and the heme export gene FLVCR1 co-express with genes functioning in oncogenic processes (FIG. 25A). The top pathway associated with HMBS expression in all tumors is 'Myc targets'; and with FLVCR1 it is 'G2M transition' (FIG. 25A). By contrast, in normal matching human tissues, all heme biosynthesis genes co-express with other heme metabolism genes (FIG. 25B). These results from human tumors suggest that HMBS and FLVCR1 may contribute to tumor biology, while their primary role is the well-characterized enzymatic function in the heme biosynthetic pathway in normal tissues.

The patient tumor transcriptome analysis is consistent with the in vivo CRISPR loss-of-function study in animal models of lung[48], pancreatic[48] and blood cancers[173]. The first steps of the heme biosynthesis pathway (linking to canonical heme biosynthesis) are dispensable in in vivo CRISPR loss-of-function studies, while the HMBS-catalyzed step (linking to oncogenesis processes) is essential in all solid and liquid cancers as inferred from in vivo gene essentiality studies.

Heme Overdrive Occurs in Tumor Microenvironment (TME)

Figure 26:
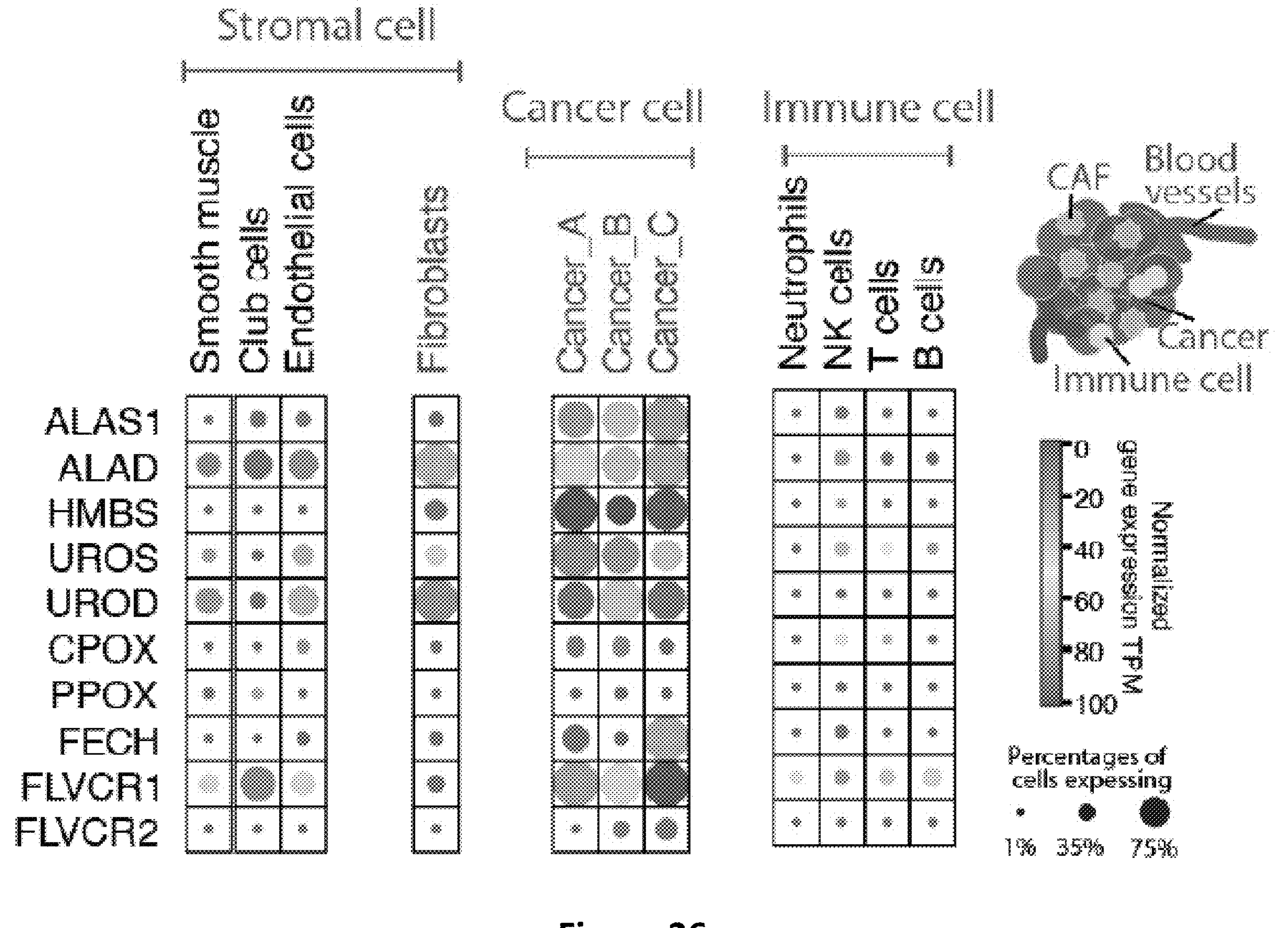
FIG. 26 is an image depicting single-cell RNA sequencing of cells from human lung cancer patients supports heme overdrive as a hallmark of cancer cells. Single-cell lung cancer transcriptomes were retrieved from Zilionis et al. The expression of the genes for the heme biosynthetic pathway enzymes and heme trafficking was analyzed in diverse cell populations present in the tumor". The expression results associated with cancer cells from 3 different patients (Cancer_A, Cancer_B, and Cancer_C) are plotted—HMBS and FLVCR1 show the most upregulated gene expression patterns. In the major groups of stromal and immune cell populations, most cell types have no evidence of heme overdrive, while cancer-associated fibroblasts show evidence of heme overdrive with upregulation of HMBS. Color shading indicates normalized gene expression levels in a given cell population; and circle sizes indicate the percentage of cells in that population with detectable single-cell transcriptomes.

Cancer cells do not exist in isolation. The heme flux aspect of heme overdrive (i.e., enhanced heme and intermediates trafficking), is evidenced by genetic dependence of heme trafficking genes (FIG. 24), and increased trafficking gene expressions in patient tumors (FIGS. 26 and 28A and B). It is remarkable that even though cancer cells do not need to synthesize their own heme in vitro (FIGS. 23 and 24) and in vivo (FIGS. 9 and 25), the heme/intermediates export gene is essential, suggesting exporting activities are of essential function. The feature of heme flux necessitates a specialized cancer microenvironment for metabolite trafficking. However, there is currently no understanding of either the source or the fate of trafficked heme in the TME. Heme trafficking is under strict control in the normal marrow environment due to the potential toxicity of heme accumulation[128-130]. In cancer, heme overdrive is likely intertwined with a specific cancer microenvironment optimized for heme transport and heme detoxification. Of particular interest is the cell population of cancer associated fibroblasts (CAF) that have prominent roles in shaping TME[174].

To study cancer cells and TME at single cell resolution, the inventors used single-cell lung cancer transcriptomes generated from Zilionis et al.[175], and analyzed for heme biosynthesis and trafficking in diverse cell populations present in the tumor. HMBS and FLVCR1 were the most upregulated heme biosynthesis genes in tumor cells from 3 different lung cancer patients (FIG. 26). These single cell transcriptomes indicate that cancer cells exhibit features of heme overdrive, consistent with the abnormal heme anabolism and endogenous PPIX accumulation upon ALA administration in cancer cells compared to normal cells[60] (FIGS. 22C and D). By contrast, major groups of stromal and immune cell populations do not show evidence of imbalanced heme biosynthesis or heme trafficking with these cell populations (FIG. 26).

In cancer, heme overdrive is likely fostered by the specific TME, including CAFs[174]. The single-cell RNAseq analysis indicated that lung CAFs show features of heme overdrive with upregulated HMBS (FIG. 26). The inventors found that heme overdrive operates in CAFs derived from primary tumors, as assessed by protoporphyrin IX (PPIX) quantification. The inventors show that CAFs from primary lung adenocarcinoma accumulate heme intermediates (e.g., PPIX) upon induction with 5-aminolevulinate (ALA), a precursor substrate of the heme metabolic pathway, but lose this feature when the CAFs are passaged in vitro (FIG. 27A). Interestingly, the fibroblasts adjacent to the tumor also show heme overdrive, albeit to a lesser extent ("CAF vs. Other fibroblasts adjacent to tumor") (FIG. 27B). These findings indicate that TME acts as a continuum of aberrant heme metabolism. Heme overdrive in TME is likely with diffusing outer edges into normal tissues, as well as 'central zones' fostering tumor growth.

In sum, the experiments show that lung cancer TME exhibits characteristics of heme overdrive, based on single-cell RNAseq analysis and the experimental validations with CAFs isolated from a treatment-naive lung adenocarcinoma patient.

Heme Overdrive is Elevated in More Aggressive Cancers and Linked to Overall Survival of Patients To evaluate clinical relevance of heme overdrive in lung cancers, the inventors studied both patient tumor tissue and single cell lung cancer RNAseq. In patient lung tumors, HMBS and FLVCR1 are the most enriched gene expressed, as compared to normal tissues (FIG. 17A). Similar patterns were identified at single cell levels within tumor heterogeneity of the same patient. The single cell expression data from Zilionis et al[175] were used to study the expression differences in more aggressive vs. more differentiated lung cancer cell populations within the same tumor. The results show both combined data of 968 patient tumors (FIG. 28A), and single cancer cells show evidence of heme overdrive (FIG. 28B).

The inventors next analyzed overall survival with respect to high and low expression of the mid-step heme biosynthesis genes, ALAD and HMBS, with data from TCGA[45]. ALAD (the enzyme responsible for the $2^{nd}$ step of heme biosynthesis) and HMBS (the enzyme that catalyzes the $3^{rd}$ step) show contrasting prognostic results in overall survival, indicating the more imbalanced heme overdrive is (the larger the differences between ALAD and HMBS expression), the poorer the overall patient survival is (FIG. 28C,D).

Bait and Kill Strategy

Heme overdrive is a unique metabolic reprogramming feature of cancer cells that can be therapeutically exploited. Since imbalanced heme pathway metabolism is fundamental to heme overdrive, cancer cells may be made particularly vulnerable to PPIX-induced cytotoxicity. Selective cancer cell death can be achieved by activating PPIX-induced cytotoxicity (i.e., via oxidative stress) with a two-step "bait-and-kill" strategy.

As discussed in the previous example, knowing that cancer cells readily take up the heme precursor ALA and bypass the first and rate-limiting step of porphyrin biosynthesis catalyzed by ALAS, the inventors engineered a two-step process for cancer metabolic death as enumerated in the previous examples. This two-step process involves first, to 'bait' cancer cells with ALA to induce PPIX accumulation, and second, to 'kill' the cancer cells with a compound that exploits the metabolic stress associated with porphyrin accumulation. As expected, ALA addition to the culture medium enhanced PPIX buildup in K562 and HEL cells, as demonstrated by the few hundred-to-thousand-fold PPIX concentration increase in relation to respective cells cultured in the absence of ALA (FIG. 17 A,B). HEL cell viability was not affected by supplementing the culture medium with ALA (1 mM final concentration) or ALA and DMSO (1 mM and 0.1% final concentrations, respectively), confirming the ability to proceed with the second step of the "bait-and-kill" strategy.

To exploit the metabolic stress associated with porphyrin accumulation (e.g., oxidative stress, lipid peroxidation), the inventors treated the human erythroleukemia HEL cell line with a range of concentrations of RSL3, an inhibitor of the antioxidant enzyme glutathione peroxidase 4 (GPX4), a phospholipid hydroperoxidase that protects cells against membrane lipid peroxidation[101]. As such, inhibition of GPX4 with RSL3 induces ferroptosis, an iron-dependent form of programmed cell death highly relevant to iron and heme metabolism[176]. Pretreatment of HEL cells with ALA increased their sensitivity towards RSL3 at least 1000-fold. Even at a RSL3 concentration of 100 mM, the viability of HEL cells remained similar to that of cells cultured in the absence of the RSL3 inhibitor. However, the viability of HEL cells grown in the presence of ALA for 4 h diminished with RSL3, reaching non-viability at a concentration of 17 mM. The decline in cell viability was yet more acute when the incubation time of the HEL cells with ALA was extended to 24 h, and the cells became non-viable with 16 nM RSL3. In contrast, ALA pretreatment did not sensitize cells to ganetespib, a heat shock protein inhibitor with antineoplastic activity[83], suggesting that ALA is not a general inducer or sensitizer of cell death. Specifically, at ganetespib concentrations less than 33 mM, HEL cells persist viably regardless of being grown in the presence or absence of ALA.

Importantly, no synergistic cytotoxic effects are found in control primary human fibroblasts (FIG. 18A). While these initial studies utilized blood cancer cell models, the inventors wanted to confirm that a similar bait-and-kill strategy can work in lung cancer models, and specifically determined that this strategy did not enhance the loss of normal lung cell viability compared to RSL3 alone (FIG. 18B,C). This lack of sensitization of normal lung cells by ALA is required for a bait-and-kill strategy to have potential against lung cancer cells.

Heme Overdrive Operates in Cancer Progenitor Cells and TME (Prophetic)

The inventors use A549-Luc and H460-Luc lung carcinoma cells[177] in orthotopic mouse tumor models as previously described[178-181]. Logarithmically growing A549 and H460 cells with over 95% cell viability at cell density of one million cells in 50 μl with 50 μg Matrigel is used to seed the mice lungs. The mix is injected into the left lung of the NOD scid gamma (NSG) mice for tumor formation. The mice are monitored with bioluminescent imaging to track primary and metastatic tumor growth. The metastasis to lymph node and chest wall is measured, after the animal displays signs of morbidity based on established methods[180,181], and confirmed by bioluminescent imaging[178,179]. After metastatic tumor formation, porphyrin accumulation is induced in lung tumors (n=3 mice) with oral administration of 100 mg/kg of aminolevulinic acid (ALA) using well established methodology[177]. Metastatic and primary tumors are cryopreserved and analyzed by: a) fluorometric quantification of porphyrin levels, b) spatial single cell transcriptomics, c) knockout of key heme metabolic genes to validate tumorigenic essentiality.

Quantification of Heme and Heme Intermediates Underlying Heme Overdrive (Prophetic)

There are two pools of heme in cells, bound and labile[15]. The bound form accounts for the bulk of heme in humans. Most of this heme is tightly bound to proteins to form hemoproteins e.g., hemoglobin and cytochromes. Labile heme, by contrast, is present in lower, typically nanomolar, quantities in normal cells, but possesses a wide number of signaling roles in, e.g., transcription regulation, translation, microRNA processing, and circadian rhythms[15]. The inventors believe that heme intermediates operate in the labile pool. The inventors evaluate 1) which heme intermediate, 2) and whether labile heme and bound heme contribute distinctly to oncogenesis. The inventors determine and quantify the two forms of heme in various cellular settings, i.e. normal lung tissue, lung tumors, metastatic tumors, before and after ALA-induced porphyrin accumulation using their recently developed ultra-sensitive assay (femtomole limit of detection to precisely quantify labile heme in the different lung tumors samples (as described previously).

The inventors quantify 1) different species of heme intermediates, and 2) labile heme vs. total heme in the following conditions: a) control, b) induced, differentiated cells, c) heme-depleted cells [Succinyl acetone (SA) is used to inhibit the second step of heme synthesis[103]], and d) cells with ALA-induced heme overdrive. Total cellular labile heme is quantified using the recently developed high sensitivity (femptomole resolution) labile heme assay that uses peroxidase to oxidize chromogenic substrates. Additionally, for the detailed biochemical characterization of the heme biosynthetic pathway intermediates (precursor porphyrins) and total final product (heme), ultra-high performance liquid chromatography (UHPLC) is used as well as well-established chemical and clinical protocols extensively used in the diagnoses of *porphyria* subtypes[104,105]. Briefly, a UHPLC system equipped with a reverse phase C18 column is used to perform the separation, while a photodiode array detector and a fluorescence detector is used to determine total heme and protoporphyrin IX (PPIX), respectively. Samples are extracted with appropriate solvents and all non-covalently associated heme and PPIX (in the organic phase) is quantified. Since during sample preparation heme ($Fe^{2+}$-PPIX) is oxidized to hemin ($Fe^{3+}$-PPIX), hemin chloride and PPIX are used as standards for quantitation. To analyze porphyrin precursors (e.g., uroporphyrin, coproporphyrin, and protoporphyrin IX), the porphyrins and heme are separated on a reverse-phase C18 column (UHPCL) and quantitated fluorimetrically. Porphyrins (high quality reagents) are commercially available (Frontier Scientific, Logan, UT and are used to validate retention times and generate standard curves, while the non-natural porphyrin mesoporphyrin serves as the internal standard spiked into each sample. Each of the porphyrins to be analyzed has well-defined molar absorptivities and $\lambda_{exc}$ and $\lambda_{em}$ maxima for the proposed assay conditions[106], and thus their quantitation using spectroscopy (fluorescence or UV-visible absorption) is straightforward[107-117].

The results of these experiments highlight the presence of intermediates vs. end product, labile heme vs. total heme, in tumors vs. normal tissues. The metabolite quantitation provides further insight into potential oncogenic roles of key heme metabolism-related genes.

Integration of Metabolite Profiles with Multi-Omics Data

To achieve concomitant, efficient heme intermediate quantification with all the samples generated the inventors have adapted a rapid protoporphyrin IX (PPIX) quantification method which is used for the cell populations generated from distinct sets of experiments. This method was previously used to generate the previous results reported for cancer cells (FIG. 17A-C), CAFs (FIG. 28), and in cancer cells and CAFs treated with drugs (FIG. 17D and FIG. 18, respectively).

PPIX accumulation is determined using fluorescence-activated cell sorting (FACS) as previously described[182]. The cells are independently seeded in 24-well plates for suspension culture (Greiner, Cat No. 662102) overnight at a density of $1.2\times10^5$ cells/well. The cells are incubated in medium containing 1.0 mM ALA, at 37° C. for 4 hours. Preparation of either 5-ALA-treated cells or control (non-ALA-treated) cells is conducted under very low light conditions. Following incubation, cells are washed thrice with Dulbecco's phosphate-buffered saline (DPBS, 1×, $Ca^{2+}$- and $Mg^{2+}$-free; Corning, Cat No. 21-031-CV) and resuspended in 250 μL of 1×DPBS. Briefly, cells are washed once with serum-free medium (Gibco, Cat No. 11835055) and incubated in 6-well plates containing the medium (described in the Cell Culture section) in either the absence or presence of 100 mM glycine or ALA (0.1 mM, 0.25 mM, 0.5 mM, and 1.0 mM) at 37° C. Intracellular PPIX concentration is measured 18 hours later by FACS. The cell suspension is passed through a 40-μm Flowmi™ Cell Strainer to eliminate clumps and debris prior to transferring to BD Falcon tubes under very low light conditions to minimize phototoxicity caused by PPIX accumulation. FACS analyses is performed using a BD LSR II Analyzer (Becton, Dickinson, and Company) and FACSDiva Version 6.1.3 software. To eliminate any background red fluorescence, the 633 nm-red laser is blocked during the collection of the PPIX emission data. PPIX emission is determined in the 619 nm and 641 nm range (630/22BP filter) upon excitation of the cells with the 405 nm laser. Forward-scatter (FSC) versus side-scatter (SSC) dot plots is used to gate the whole cells and thus remove the contribution of the cell debris from the population being examined. A minimum of 10,000 of the gated cells is then depicted in dot plots of SSC vs. PPIX fluorescence; the gate is defined based on cancer cells without any perturbation as negative controls.

This method links the independently determined heme metabolite levels with the results from the omics studies to generate distinct types of experimental evidence to support a multi-faceted understanding of cancer heme overdrive.

Heme Overdrive Gene Expression in Cancer Cells (Prophetic)

The inventors examine transcriptomes of cancers both at tissue level and at single cell resolution to show that heme overdrive is coupled with multiple oncogenic cellular pathways, such as Myc signaling pathways (FIG. 25), to fuel tumor growth. The inventors examine 1) heme biosynthesis gene expression, 2) lung tissue differentiation signature genes, and 3) oncogenic processes related pathways such as Myc and Kras associated genes, in both tumors and normal tissues.

For patient tissue and bulk cell culture RNAseq analysis, the gene expression patterns related to heme biosynthesis, metabolism, and signaling from patient-derived tumor samples is analyzed (using methods similar to those used to generate FIG. 22E, and FIG. 25), and compared by using the publicly available resources to study tissue-specific gene expression, the GTEx project[43,44] and TCGA program[45].

For single cell RNAseq studies, the Cell Ranger Single-Cell software Suite (10× Genomics) is used for data processing, sample demultiplexing and gene expression quantification. For data analysis, genes with more than one unique molecular identifier (UMI) counts is used. The top 1000 most variably expressed genes is used for further clustering, t-Distributed Stochastic Neighbor Embedding (t-SNE) analysis is performed to reduce the data dimension to a two-dimensional space, and k-means clustering is used to identify cell populations. The mean expression of genes in all cells in a given cluster is calculated, and the expression of each gene is compared with that of the same gene in all the other clusters. For cell classification, the mean expression profiles of all cells is first calculated, and then each cell is assigned to a subpopulation by the highest Spearman's correlation.

The inventors expect to uncover the first cancer heme overdrive gene expression pattern underlying the biochemical pathways at single cell resolution, with both patient tissues and in vivo models.

Determination of Metabolites and Transcriptomes in Lung Cancer TME (Prophetic)

Recently, cancer-associated stromal cells, such as CAFs, have been shown to shape cancer cell niches and promote cancer progression[94,95]. The preliminary evidence indicates that heme overdrive operates in CAFs, based on analysis of single-cell lung tumor data, and the validations of patient tumors. Presumably, this can be attributed to CAF being highly anabolic with elevated collagen production and growth factor secretion, features uniquely shared with cancer cells. As such, targeting heme overdrive can kill both cancers and CAFs.

The inventors isolate CAFs from primary and metastatic tumors in vivo. The isolated CAFs and matching normal fibroblast pairs are used for comparison, and for each CAF vs. normal pair, the inventors conduct 1) PPIX quantifications upon ALA-induced porphyrin accumulation, ii) transcriptomics to reveal the cellular gene expression profiles for the heme metabolic enzymes, and iii) quantification of extracellular (media) vs. intracellular PPIX (cellular) levels at nanomolar resolution.

Further Exploration of Heme Overdrive being Associated with Tumorigenesis (Prophetic)

To further explore heme overdrive associated with tumorigenesis the inventors generate A549-Luc and H460-Luc cell KO mutants of HMBS, a major driver gene that has been identified as being associated with heme overdrive (FIGS. 9 and 25-27). The inventors believe that elimination/attenuation of this metabolic enzyme diminishes cancer survival, presumably due to altered biosynthesis of heme intermediate. These mutants are generated and characterized as presented in FIG. 23 (using a Synthego Multi Guide Knockout Kit). Immunoblotting to confirm protein loss and sequencing of PCR amplified products of the edited genomic region is performed to confirm deleterious editing.

If, given the in vitro gene essentiality of HMBS, cells that lack HMBS cannot be obtained, HMBS expression can be silenced in an inducible manner using shRNA. Following stable expression of doxycycline-inducible shRNA expressing vectors the inventors can confirm HMBS loss with doxycycline treatment.

The effect of the loss HMBS expression is determined with respect to cell growth and viability in vitro using standard approaches and assess HMBS-dependent processes by performing transcriptomic and pathway analysis.

These cells and their parental controls are placed orthotopically in mice, as described above, and tumor formation is assessed with bioluminescent imaging. When using cells designed to express inducible shRNA for HMBS, HMBS expression is temporally controlled by providing mice with water containing doxycycline to address a role of HMBS on primary tumor growth, metastases, and metastatic tumor growth, depending on the timing of doxycycline administration.

While HMBS has been shown to be essential for in vivo lung tumor formation via an essentiality screen, these experiments directly confirm and address a role of HMBS on tumor growth and metastasis in vivo to further support the concept that heme metabolic enzymes have additional roles in in vivo tumorigenesis than simply leading to heme production—since the essentiality of FECH, which catalyzes the final step in heme synthesis, is not different in vivo than in vitro, suggesting production of heme intermediates (e.g., via HMBS) is playing a unique role in tumor growth.

Bait-and-Kill Strategy In Vivo in Metastatic Lung Cancer Models (Prophetic)

The inventors previous results indicate exquisite cancer specificity of heme overdrive, with its absence in normal cells. The inventors designed a bait-and-kill strategy that utilizes heme overdrive to sensitize cancer cell models to cytotoxic drugs in vitro. Cancer cells can be significantly sensitized to "killing" by compounds that attack the cellular glutathione antioxidant system (FIG. 17), or artemisinin, an anti-malarial drug that antagonizes the antioxidant system triggered by porphyrin-induced oxidative stress (not shown). The bait-and-kill strategy has no detectable in vitro toxicity in primary non-cancerous lung cells and the wide clinical use of ALA for photodynamic therapy and imaging indicates it is safe on its own (FIG. 18B,C).

Testing Drug (Bait-and-Kill) In Vivo (Prophetic)

The in vitro results are validated in other types of cancer cells (FIGS. 17 and 18) using A549 and H460 lung cancer cells. The compounds RSL3 (MedChemExpress) and ganetespib (MedChemExpress) are dissolved in DMSO.

Cells are seeded in 384-well plates and allowed to proliferate for 48 hours. The cells are treated with 1 mM ALA in individual plates for 4 hours and 24 hours. Both ALA treated and non-treated cells are handled under very low light conditions throughout this assay. Both ALA-treated and non-treated cells are treated with the compounds RSL3 and ganetespib as in the previous studies (FIG. 17) and cell proliferation is measured utilizing the CellTiter-Glo 2.0 reagent.

To assess a "bait-and-kill" strategy in vivo, lung cancer mouse models described previously are treated with vehicle control, 100 mg/kg ALA (orally), 30 mg/kg RSL3 (intraperitoneal injection), and with the combination of ALA and RSL3. ALA and RSL3 are administered every other day for two weeks. Dosing is based on multiple reports on the literature using each of these compounds alone in mice. In addition to the effect on tumor size (bioluminescence), tumors are examined for porphyrin accumulation (fluorescence) and other markers of cell proliferation (e.g., KI-67), oxidative stress, and cell death.

For mouse studies, the inventors predict that the tumor (bioluminescence) data follows normal distribution and the standard deviations of two arms are about 20%. With 7 mice per arm, 82.5% power is available to detect a 50% difference (an effect size of 1.8) in bioluminescence at a two-sided significance level of 5%.

Mechanisms of Cell Death in Bait-and-Kill (Prophetic)

The bait-and-kill strategy (exemplified in FIGS. 17, 18) is expected to lead to ferroptosis or related forms of redox stress death, due to enhanced oxidative stress induced by porphyrin accumulation and inhibition of GPX4. This strategy is used on A549 and H460 lung cancer cells and cell viability is assessed (Cell-Titer Glo (Promega)) and concomitant cytosolic and lipid peroxidation using $H_2$DCFDA and C11-BODIPY followed by flow cytometry. Ferroptosis is confirmed using deferoxamine (DFO), which chelates intracellular iron, preventing ferroptosis[156].

Normal, non-transformed cells (e.g., primary human lung fibroblasts) are used as controls to confirm the sensitization to ferroptosis induction upon induction of porphyrin (heme intermediate) accumulation by ALA treatment is specific to cancer cells. Results and healthy control experiments are confirmed in replicated experiments (n>=3). These experiments specifically determine the extent to which the bait-and-kill strategy enhances redox stress with ALA pretreatment/RSL3 treatment which would sensitize cancer cells to induction of cell death/ferroptosis via redox stress.

An orthotopic lung cancer model is used which represents clinical pathology more accurately. Alternatively, genetically engineered mouse models of lung cancer can be used or a standard mouse subcutaneous xenograft approach can be used, where tumor growth in vivo can be assessed. Proof of principle success opens the opportunity to assess patient derived xenografts to the bait-and-kill strategy. Other similar heme intermediate enzymes such as UROS, CPOX, and PPOX which also show enhanced essentiality in in vivo screens compared to in vitro can also be assessed (FIG. 9B).

Example 4—Heme Overdrive in Blood Cancers

Almost 200 distinct types of hematological malignancies are defined by the WHO 2016 guidelines[168], most of them are rare cancers occurring in less than 6 in 100,000 people[168]. Rare blood cancers arise from distinct hemopoietic cell developmental lineages (FIG. 29A), and they are diverse in pathology, clinical presentations, and susceptibility to cancer treatments[168]. Rare disease patients suffer from inadequate diagnosis and treatments due to resource limitations[183]. Military personnel are at increased risk to develop many types of blood cancers linked to exposure to radiation and environmental carcinogens[184,185]. In addition, blood cancer risk is also increased in children from parents who have undergone military deployment[186]. There are urgent needs to develop novel, cost-effective, and non-toxic therapeutics that are effective in rare blood cancers to improve the health and lives of our military personnel and their families, in addition to the general population.

As noted in the previous examples, the inventors have found that all cancer cells depend on an inefficient heme metabolism, termed "heme overdrive". In normal cells, heme biosynthesis pathways (FIG. 29B) consist of 8 enzymatic steps under tight regulation with the first step occurring in mitochondria and catalyzed by 5'-aminoLevulinic Acid (ALA) synthase (ALAS). Subsequent enzymatic steps occur in the cytosol and result in early precursors (e.g., ALA, porphobilinogen), heme intermediates (e.g., hydroxymethylbilane, uroporphyrinogen III, coproporphyrinogen III, protoporphyrin IX (PPIX)) and heme end product (i.e., an iron ion coordinated to a porphyrin). This process is balanced leading to heme homeostasis that is critical to several cellular functions in normal cells (FIG. 29B). Surprisingly, in cancers, the genetics and genomics data show that, a) cancer cells do not need genes to biosynthesize either early precursor (e.g., ALA, porphobilinogen), or heme end products for survival, and b) they require genes for accumulation of heme intermediates (e.g., PPIX) for survival, i.e. they only require genes encoding HMBS ($3^{rd}$ step), UROS ($4^{th}$ step), UROD ($5^{th}$ step) and CPOX ($6^{th}$ step) for survival. As such, unlike normal cells, cancer cells are dependent on enzymes that make heme-intermediates and not on the end product heme to survive. Because of this metabolic rewiring, cancer cells produce aberrant levels of heme intermediates (porphyrins) and have increased heme trafficking to compensate for the decreased heme synthesis. Heme overdrive provides an ideal cancer target as it is present in all cancers (cancer universal), essential to all cancers (cancer essential), and absent in normal cells (cancer specific).

The challenges of treating rare cancers is that while collectively they impact large sections of the population each disease affects relatively few people, creating a bottleneck for resource allocation for research and treatment development[183]. The inventors overcome this challenge through the development of a novel therapeutic approach applicable to multiple types of rare cancer. The inventors further assess heme overdrive and its targeting as a novel therapeutic approach in rare blood cancer using in vitro and in vivo models.

The inventors have determined: 1) by CRISPR loss-of-function that cancer cells, including rare blood cancers from distinct hematopoietic lineages, exhibit heme overdrive (FIG. 29A), 2) by single-cell RNAseq that heme overdrive is present in cancer progenitor cells (from primary erythroleukemia patient biopsies) but not normal cells, and 3) clinical research and analysis of the previous results show that heme overdrive is absent in healthy primary human hematopoietic stem cells, and normal stromal cells. The results demonstrate exquisite cancer specificity of heme overdrive, and warrant targeting it in rare cancers.

As noted in the previous examples, the inventors have developed a bait-and-kill strategy that utilizes heme overdrive to specifically target cancer cells. This strategy is exemplified by a combination of 5-aminolevulinic acid (ALA, a clinically proven safe heme precursor)[79] to "bait" cancer cells to induce porphyrin accumulation, sensitizing them to be "killed" by RSL3[187, 101], or artemisinin[164], which antagonizes the antioxidant system triggered by porphyrin-induced oxidative stress. In the previous results, the inventors show that models of two different rare cancers, erythroleukemia (i.e., AML M6)[188,189] and myelofibrosis[190-191], are killed with their novel bait-and-kill strategy with no detectable in vitro toxicity toward normal cells.

Defining Heme Overdrive In Vivo in Blood Cancers (Prophetic)

The in vivo myelofibrosis models[149,150] are used for porphyrin accumulation with ALA induction. After cancer establishment in vivo[149,150], the inventors induce porphyrin accumulation in cancers (n=5 mice) with oral administration of 100 mg/kg of ALA using well established methodology[177]. Mice peripheral blood during the experiment at three time points (day 0, day 5 and day 10), and marrows and spleen at the end points for both control and treated groups, are cryopreserved and sectioned for: a) fluorometric quantification of porphyrin levels, b) single cell transcriptomics, and c) cancer stromal cell heme overdrive studies.

As detailed in previous examples, the inventors analyzed the in vivo mouse CRISPR/CAS9 loss-of-function and metabolic essentiality data from AML model[173], pancreatic and lung cancer models[48]. Consistent with in vitro CRISPR loss-of-function gene essentiality data, all three cancers showed the mid-step heme biosynthesis genes are essential for cancer survival in vivo (FIG. 30). The essentiality of either ALAS or FECH, which encode for the first and terminal enzymes of the heme biosynthesis pathway, respectively, did not differ significantly ($p<0.01$) from in vitro to in vivo, in all three cancers. Next, the inventors specifically examined the in vitro to in vivo essentiality change in the solid tumor study, because that study design focused on cancer metabolic pathways[48]. Most metabolic gene essentialities were similar between the in vitro and in vivo settings[48]. Strikingly, out of the ~2900 examined metabolic genes, the genetic dependencies of both murine pancreatic and lung cancers to grow in vivo were only increased for genes that encode heme metabolic enzymes responsible for the intermediate biosynthesis steps[48] (HMBS, UROS, CPOX, and PPOX) (FIG. 30). The analysis revealed that heme intermediates requirement has increased importance in vivo for cancer cell survival, suggesting potential role of heme overdrive in forging Tumor Microenvironment (TME) and crosstalk of tumor cells and their stromal cells.

Figure 31:
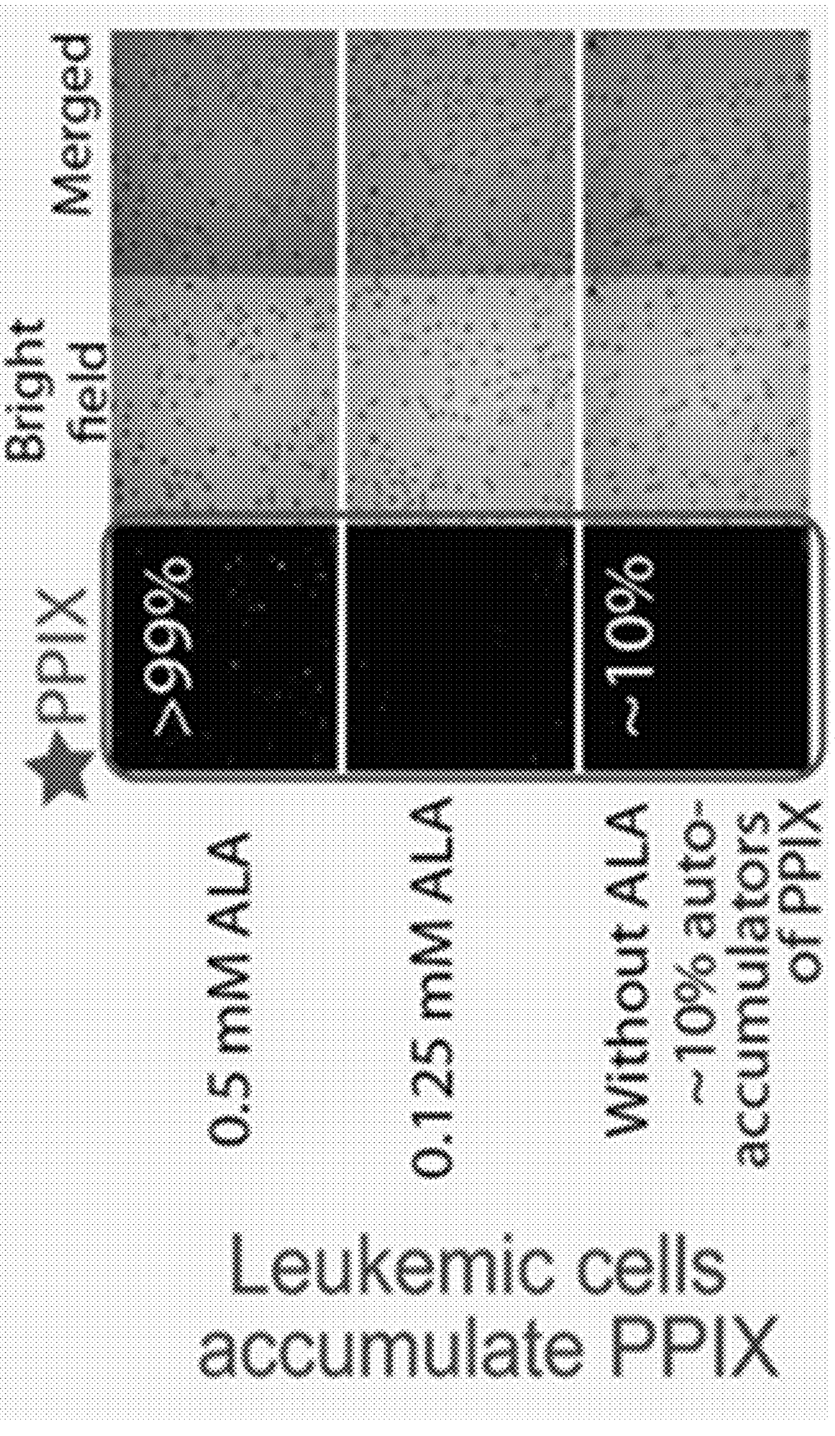
FIG. 31 is an image depicting heme overdrive is unique to cancer cells and absent in normal cells. Leukemic BaF3_Jak2mt cells accumulate PPIX.

The inventors have established that heme overdrive is specific to cancer cells by investigating and comparing heme biosynthesis in diverse types of non-cancerous cells, i.e., normal differentiated cells, replicating fibroblasts, human primary hepatocytes, and human primary hematopoietic stem cells. The inventors examined the evidence of heme overdrive, in the aspects of imbalanced heme biosynthetic pathway, and accumulation of heme pathway intermediates upon ALA induction. First, normal human peripheral blood mononuclear cells (PBMCs) do not show accumulation of heme intermediates upon ALA-induction[60], in contrast to leukemic cells (FIG. 31A). Second, the robust primary human hepatocyte systems[62] demonstrated normal metabolically active primary hepatocytes do not show accumulation of porphyrins (FIG. 22C). By contrast, >99% of the liver cancer cell lines showed rapid porphyrin accumulation upon induction with ALA, one of the canonical features of heme overdrive. Third, in replicating primary human lung fibroblasts, no heme intermediates accumulation was found (FIG. 22D). Fourth, human hemopoietic stem cells do not show evidence of heme overdrive because ex vivo in duction with ALA did not lead to accumulation of porphyrins in autologous transplant studies[64,65].

The inventors have also previously generated CRISPR knock-out (KO) of the genes encoding FECH and ALAS2 in K562 cells (FIG. 13D-E). As noted in previous examples, under a heme homeostasis model, a FECH KO mutant should not survive, because it is a single copy gene in humans and with no known functional substitute. Consistent with the heme research field consensus that FECH function is important in normal cells, a prior human stem cell KD experiment showed cell death upon FECH KD[63]. However, under heme overdrive, cancers rely on heme trafficking and require porphyrin intermediates, and the final step of heme synthesis is not essential. Indeed, the FECH KO has normal growth (FIG. 22D) and no apparent abnormality under standard culture conditions, confirming the previous gene essentiality screen data (FIGS. 5 and 30 shown erythroleukemia in vitro). The dispensability of ALAS and FECH is in sharp contrast with normal stem cell's requirement for ALAS and FECH (FIG. 13G). The previously generated shRNA knock down results[10] from human bone marrow hemopoietic stem cells demonstrates normal cell dependency on all the heme biosynthesis genes tested.

Quantify and Delineate the Species of PPIX in Oncogenesis

The inventors evaluate which heme intermediate contributes to oncogenesis by determining and quantifying the forms of heme metabolites in various cellular settings, i.e., cancer cell and normal human fibroblasts. The metabolites are quantified in the following conditions: a) control, b) heme overdrive induction with ALA, and c) heme/intermediates inhibition with Succinyl Acetone (SA). For the detailed biochemical characterization of the heme biosynthesis pathway intermediates (both early and later precursor porphyrins) and total final product (heme), HPLC or ultra-performance liquid chromatography (UPLC) are used as well as well-established clinical protocols extensively used in the diagnoses of porphyria subtypes[104,105]. The roles of PPIX in oncogenesis is delineated by inducing or inhibiting PPIX in cells and examining cell proliferation and cancer molecular markers. Porphyrins (high quality reagents) are commercially available (Frontier Scientific, Logan, UT) and are used as standards. Each of the porphyrins to be analyzed has well-defined molar absorptivities[106], and thus, their quantitation using spectroscopy (fluorescence or UV-visible absorption) should be straightforward[107-117]. ALA induction sustains cell growth via intermediates accumulation in cancers, and conversely, PPIX production inhibition hampers cell growth. The results of the experiments involving heme intermediates induction define 1) the specific porphyrin species accumulated by cancers in vivo, and 2) the quantity of each species associated with oncogenesis. These experiments deliver the precise biochemical makeup of heme intermediates of blood cancers.

Heme Overdrive in Single Cancer Cells

The inventors assess heme trafficking with induction of heme precursor ALA in cancer in vivo. The partitioning and dynamics of heme metabolites are quantified. These experiments provide novel insight into the potential contribution(s) of the TME to cancer heme overdrive.

As noted in the previous examples, to study heme overdrive in primary patient tissues, the inventors previously performed single-cell RNAseq on biopsies from acute myeloid leukemia (AML) patients (n=2). For each patient, around 2000 single-cell transcriptomes were obtained, and cells of various differentiation stages and cell types were analyzed. Interestingly, in two independently generated patient biopsy samples, only a minority of cells, about 5-10% of total cells, were identified as cancer progenitors (FIG. 14A-C), and they bore hybrid features of mature erythroid cells and stem cells. The cancer progenitor cells (FIG. 14D) were observed to have both mature cell features, e.g. hemoglobin production, and early progenitor properties, e.g. vigorous proliferation. Specifically, they were characterized by elevated iron and heme metabolic gene expression, cell proliferation markers, KRAS and anabolism process genes, yet they lacked normal stem cell progenitor marker gene expression e.g., SOX4 and JUN[70,71]. Additionally, the cancer progenitor cells exhibited imbalanced heme biosynthesis, particularly elevated gene expression for enzymes that catalyze the intermediate steps of heme biosynthesis, e.g. HMBS and UROD. Furthermore, the cancer progenitor cells also had a higher expression level of genes related to heme trafficking such as FLVCR1 and DMN2. The results show that these cancer progenitor cells have heme overdrive, and are consistent with ex vivo ALA heme induction studies in AML transplant studies.

For the single cell RNAseq (10×Genomics), the inventors use similar methods to those followed to obtain the data shown in FIG. 14 of the previous examples. For quality control, each cell must have at least 200,000 reads mapped to references, and less than 50% mapped to the External RNA Controls. The inventors reconstruct the single-cell developmental lineage from individual cell transcriptomes. Critical heme overdrive-related enzymes and transporters, e.g., major drivers of heme overdrive and glycolysis, are monitored to assess the metabolic status of the cancer progenitor and partner cells. The inventors study in vivo leukemic samples (n=5), with similar methods used previously. The inventors expect to identify both the malignant progenitors from peripheral blood and marrow, and potential blood cancer stromal cells from bone marrows, that having heme overdrive at single cell resolution.

Cancer Stromal Cell in Heme Overdrive

The inventors perform functional studies on the stromal cells in relation to heme overdrive. The inventors show that blood cancer stromal cells have heme overdrive and can be therapeutic targets.

First, to gain initial insight into heme metabolism in human bone marrows, the inventors searched the recently generated multiple scRNAseq experimental data sets[192-194] from bone marrow niches, both under normal and acute chemo stress conditions. It was found that under normal hematopoiesis conditions, the major group of bone marrow stromal cells, i.e. Mesenchymal stem cells (MSCs), osteoblasts, endothelial cells (ECs), pericyte, fibroblasts, and chondrocytes, do not show evidence of heme overdrive. Strikingly, the cell population was identified possessing heme overdrive belongs to a newly expanded stromal cell population (consisting of different types of stromal cells), after acute insults of chemo agent 5'-FU[194] (FIG. 32). These results show that the bone marrow niche stromal cells can have rapidly rewired heme metabolism, likely initiating heme overdrive, under acute chemo stress.

Next, it was found that heme overdrive operates in TME cells derived from primary tumors, as assessed by protoporphyrin IX (PPIX) quantification. Cancer associated fibroblasts (CAFs) from primary lung adenocarcinoma accumulate heme intermediates (e.g., PPIX) upon induction with 5-aminolevulinate (ALA), a precursor substrate of the heme metabolic pathway, but lose this feature when the CAFs are passaged in vitro (FIG. 27A). Interestingly, the fibroblasts adjacent to the tumor also show heme overdrive, albeit to a lesser extent ("CAF vs. Other fibroblasts adjacent to tumor") (FIG. 27B). These findings indicate that TME acts as a continuum of aberrant heme metabolism. Heme overdrive in TME is likely with diffusing outer edges into normal tissues, as well as 'central zones' fostering tumor growth. As such, cancer TME exhibits characteristics of heme overdrive which lends to targeting heme overdrive kills both cancer cells and their stromal cells.

The inventors investigate isolated cancer stromal cells, e.g. endothelial cells. The isolated primary cancer associated endothelia and matching normal cell pairs are purchased (BioreclamationIVT), and for each TME vs. normal pair, the inventors i) conduct ALA induction experiments with PPIX quantifications, ii) perform transcriptomics on cell populations with different PPIX levels, to reveal the cellular expression profiles of heme metabolic enzymes, and iii) quantify extracellular (media) vs. intracellular PPIX (cellular) levels at nanomolar resolution.

Bait-and-Kill in Rare Blood Cancers

Heme overdrive is elevated in end-stage cancers and linked to overall survival of patients. The inventors studied patient cancer biopsy transcriptome data in relation to disease progressions and outcomes (FIG. 33A). The inventors analyzed patients' overall survival with respect to high and low expression of each of the heme biosynthesis genes, with data from TCGA[45]. It was found that the genes of the mid-steps of the pathway UROS (the enzyme responsible for the 3$^{rd}$ step of heme biosynthesis) and UROD (the enzyme responsible for the 4th step of heme biosynthesis), are significantly upregulated in patients with poorer prognosis in overall survival, while neither the first nor the last steps gene expression is associated with patient survival. The analysis shows different prognostic results, of mid-steps vs first/last steps in overall survival, indicating the more imbalanced heme overdrive is (the larger the differences between mid-steps and other genes expression), the poorer the overall patient survival is (FIG. 33B). The experimental validation based on isogenic cell lines flowcytometry data shows that, blood cancer cell line BaF3 specifically exhibits growth factor dependent PPIX accumulation, as compared to its isogenic aggressive Jak2-V617F transformed cell line BaF2-Jak2mt (FIG. 33C). This experiment indicates that PPIX accumulation is linked to blood cancer aggressiveness.

Testing Bait-and-Kill In Vitro in Diverse Rare Blood Cancer Models

Heme overdrive's key features of cancer-universality, essentiality and specificity provide foundations for a targeting strategy that is of board applicability, high efficacy and non-toxicity (FIG. 34A). The inventors devised a bait-and-kill strategy to target cellular vulnerably as a results of heme overdrive.

Cancer cells are susceptible to 'baiting'-inducing rapid accumulation of heme precursor porphyrin metabolites (e.g., PPIX), due to the imbalanced heme biosynthesis enzymatic activities. For 'bait', cells readily take up the heme precursor ALA and bypass the first and rate-limiting step of porphyrin biosynthesis catalyzed by ALAS1. As an exogenously provided precursor, ALA has multiple import routes into the cell. The induction with ALA to induce porphyrin accumulation in cancers has been clinically and safely used in PDT for decades[66-71]. Thus, the inventors designed a two-step process to engineer cancer cell metabolic death: first, 'bait' with ALA to induce PPIX accumulation to up to a few hundred-to-thousand-fold higher concentration as compared to control cells, and second, 'kill' with a compound that exploits the metabolic oxidative stress of porphyrin accumulation.

To exploit the metabolic stress of porphyrin accumulation, the inventors treated the human erythroleukemia HEL cell line, mouse myelofibrosis BaF3_Jak2mt and liver cancer cell line HC-04. ALA pre-treatment leads to accumulations of intermediates PPIX that can cause membrane lipid peroxidation. Cancer cells likely have elevated dependence on the antioxidant enzyme glutathione peroxidase 4 (GPX4) [195], which is a phospholipid hydroperoxidase that protects cells against peroxidation. Subsequently, inhibition of GPX4 with RSL3[101, 196] and/or exacerbate heme related redox stress with artemisinin[164], induces acute redox stress and cell death. Pretreatment of cancer cells with ALA increased RSL3 sensitivity at least 1000-fold (FIG. 34B-D). Importantly, this high efficacy is achieved in in both types of rare blood cancers, human and mouse cancers, as well as liquid and solid tumors. In contrast, ALA pretreatment did not sensitize cells to the heat shock protein inhibitor ganetespib[197] suggesting ALA is not a general sensitizer to induction of cell death (FIG. 34E).

The inventors performed the same bait-and-kill approach in primary human lung fibroblasts and found no increased sensitivity to RSL3 (FIG. 34F,G). This non-toxic effect in normal cells stands in stark contrast with the sub-nM range of IC50 of drugs in various cancer cell lines (e.g., HEL, K562, K562-FECH-KO, K562-ALAS2-KO, BAF3-Jak2mt, HC-04). Importantly, both rare blood cancers, erythroleukemia and myelofibrosis are killed in sub-nM drug concentrations. These experiments show cell growth and viability of non-cancer cells are not impaired by the bait and kill strategy.

The inventors perform similar in vitro bait-and-kill in all six rare blood cancers (as outlined in FIG. 29A), i.e. with three selected candidate 'kill' agents aggravating redox stress, i.e. RSL3[196,101], erastin[198] and the antimalarial artemisinin[164]. Each experiment is performed with biological replicates (n=2), each with a technical replicates (n=3). The inventors show that bait and kill is effective against rare blood cancers from distinct major hemopoiesis lineages.

Testing Bait-and-Kill In Vivo in Diverse Rare Blood Cancer Models (Prophetic)

The inventors test and characterize bait-and-kill with in vivo myelofibrosis models[149,150]. The most promising bait and kill strategies for in vivo evaluation of RSL3[196,101], erastin[198], and artemisinin[164] (exacerbating redox stress by PPIX accumulation) are assessed. This includes 4 treatment arms: untreated (vehicle), treatment with ALA, treatment with the candidate drug, and treatment with the combination of ALA and drug (the bait and kill test arm of the experiments). Tumor burden/size is measured over time as described previously. Following treatment, tumors are examined for PPIX accumulation (PPIX fluorescence) and immunohistochemical staining for cell proliferation markers (e.g., Ki-67)[151], glutathione levels[152] and lipid peroxidation[153]. RNA-seq studies are performed on candidate bait and kill strategies (control, ALA-treated, drug-treated, and the combination of the two) to begin to evaluate if cell death involves unique transcriptomic changes that may shed light on the cellular/mechanistic effects. Subsequently to gain further mechanistic insight, MALDI-TOF cell-based assays are performed to assess metabolic changes and study effects[147,148]. Promising results and healthy control experiments will be confirmed in replicated experiments (n>=3).

Example 5—Heme Overdrive in Liver Cancer

Liver cancer, including primary hepatocellular carcinoma (HCC), causes major global cancer death[199]. One of the main causes of HCC, Non-Alcoholic Fatty Liver Disease (NAFLD), has increased over 10-fold in the US army forces during the last 20 years[200], and alarmingly, a significant increase of HCC has been found in US veterans at autopsy[201]. While surgical resections and liver transplants are the only curable treatment, most patients are not candidates for surgical interventions[199,202,203]. Conventional and recently FDA-approved drugs[204] are still of limited efficacy that extending patients' life only ~3 months[205,206], and have significant toxicity[203,207]. The inventors overcome these challenges through use of a novel, minimally toxic therapeutic approach in liver cancer.

As noted in previous examples, the inventors discovered a novel cancer cell metabolic reprogramming. In normal cells, heme biosynthesis pathways consist of 8 enzymatic steps under tight regulation. The process is balanced and leads to heme homeostasis that is critical to several cellular functions in normal cells (FIG. 19) Conversely, in cancer cells, genes are not needed to biosynthesize either early precursor (e.g., ALA, porphobilinogen) or heme end products for survival. Rather, cancer cells require genes for accumulation of heme intermediates (e.g., PPIX) for survival; and c) they only require genes encoding HMBS ($3^{rd}$ step), UROS ($4^{th}$ step), UROD ($5^{th}$ step) and CPOX ($6^{th}$ step) for survival. The inventors coined this cancer metabolic rewiring process "heme overdrive". This dependence on genes encoding these enzymes is present in all cancers and absent in all normal cells, thus heme intermediates have a universal, yet unknown role in oncogenesis. Heme overdrive provides an ideal cancer therapeutic target with such therapy having the potential to be effective, have low toxicity, and be applicable against a broad range of cancers. The exquisite cancer-specificity of heme overdrive offers elegant potential for needed therapies to kill only cancer cells, not normal cells. Heme overdrive is a unique metabolic program of liver cancer cells that can be therapeutically exploited with low toxicity, which can lead to paradigm shifting treatment approaches.

The inventors previous results showed that heme overdrive is operating in human liver cancers and that liver cancer cells can be killed in vitro with sub-nM drugs with no toxicity in normal human cells. The inventors determined: 1) by CRISPR loss-of-function analysis that primary and metastatic liver cancer cell lines exhibit heme overdrive, 2) by single-cell RNAseq that heme overdrive is present in primary cancer progenitor cells but not normal cells, and 3) using a liver model[208-210], that heme overdrive is absent in metabolically active primary human hepatocytes. These results demonstrate exquisite cancer specificity of heme overdrive, and warrant targeting it in liver cancer.

Further, the inventors developed a bait-and-kill strategy that uses heme overdrive to specifically target cancer cells. For example, a combination of 5-aminolevulinic acid (ALA, a clinically proven safe heme precursor) can be used to "bait" cancer cells to induce porphyrin accumulation, sensitizing them to be "killed" by RSL3, or artemisinin, which antagonizes the antioxidant system triggered by porphyrin-induced oxidative stress. The inventors have successfully killed liver cancer cells in vitro while not harming normal cells.

Heme Overdrive in HCC Cancer Cells and the TME In Vivo (Prophetic)

The inventors use a mouse PDX model (e.g. PDX-HCC_LI5129, with 80% of the tissue of malignant tumor, CrownBio). After tumor formation, porphyrin accumulation is induced in tumors (n=3 mice) with oral administration of 100 mg/kg of ALA using well established methodology[177].

Previous Work

As noted in previous examples, the inventors previously determined gene essentiality from genome-scale CRISPR/Cas9 loss-of-function screens in over 300 human cancer cell lines covering different cell lineages and estimated gene dependency using CERES. These results uncovered the "imbalanced" nature of heme biosynthesis in cancer, with many cancers surviving without functional first and terminal enzymatic steps, but dependent on the intermediate steps such as UROD, CPOX. (FIG. 5). Further, the inventors analyzed the in vivo mouse CRISPR/CAS9 loss-of-function and metabolic essentiality data from pancreatic and lung cancer models. Most metabolic gene essentialities were similar between the in vitro and in vivo settings (FIG. 9A). Strikingly, out of the ~2900 examined metabolic genes, the genetic dependencies of both murine pancreatic and lung cancers to grow in vivo were only increased for genes that encode heme metabolic enzymes responsible for the intermediate biosynthesis steps (HMBS, UROS, CPOX, and PPOX) (FIG. 9A, B). The essentiality of either ALAS or FECH, which encode for the first and terminal enzymes of the heme biosynthesis pathway, respectively, did not differ significantly. The analysis revealed that heme intermediates requirement has increased importance in vivo for cancer cell survival, suggesting potential crosstalk of tumor cells and their TME.

As noted in the previous examples, the inventors compared heme biosynthesis in diverse types of non-cancerous cells, i.e., normal differentiated cells, replicating fibroblasts, human primary hepatocytes, and human primary hematopoietic stem cells. The inventors examined the evidence of heme overdrive, in the aspects of imbalanced heme biosynthetic pathway, and accumulation of heme pathway intermediates upon ALA induction. Normal human peripheral blood mononuclear cells (PBMCs) do not show accumulation of heme intermediates upon ALA-induction. The robust primary human hepatocyte systems demonstrated that normal metabolically active primary hepatocytes do not show accumulation of porphyrins (FIG. 22C). By contrast, >99% of the liver cancer cell lines showed rapid porphyrin accumulation upon induction with ALA, one of the canonical features of heme overdrive. In replicating primary human lung fibroblasts, no heme intermediates accumulation was found (FIG. 22D).

CRISPR KO validations show cancer cells do not need to synthesize their own heme. The inventors previously generated CRISPR knock-out (KO) of the genes encoding FECH and ALAS2 in K562 cells (FIG. 13A-C). Under a heme homeostasis model, a FECH KO mutant should not survive, because it is a single copy gene in humans and with no known functional substitute. Under heme overdrive, cancers rely on heme trafficking and require porphyrin intermediates, and the final step of heme synthesis is not essential. Indeed, the FECH KO has normal growth (FIG. 13C) and no apparent abnormality under standard culture conditions, confirming the previous gene essentiality screen data. The dispensability of ALAS and FECH is in sharp contrast with normal stem cell's requirement for ALAS and FECH (FIG. 13D). The previously generated shRNA knock down results from human bone marrow hemopoietic stem cells demonstrates normal cell dependency on all the heme biosynthesis genes tested.

Quantify and Delineate the Role of PPIX in Oncogenesis (Prophetic)

The inventors determine and quantify the forms of heme metabolites in various cellular settings, i.e., liver cancer cell HepG2 and normal human fibroblasts. The inventors quantify the metabolites in the following conditions: a) control, b) external heme depletion[103], and c) heme overdrive induction with ALA. For the detailed biochemical characterization of the heme biosynthesis pathway intermediates (both early and later precursor porphyrins) and total final product (heme), HPLC or ultra-performance liquid chromatography (UPLC) is used as well as well-established clinical protocols extensively used in the diagnoses of porphyria subtypes[104,105]. The inventors delineate the roles of PPIX in oncogenesis by inducing or inhibiting PPIX in cells and looking at cell proliferation and cancer molecular markers. Porphyrins (high quality reagents) are commercially available (Frontier Scientific, Logan, UT) and are used as standards. Each of the porphyrins to be analyzed has well-defined molar absorptivities[106], and thus, their quantitation using spectroscopy (fluorescence or UV-visible absorption) should be straightforward[107-117]. The results of the experiments involving heme/intermediates depletion vs. porphyrin induction defines their role in oncogenesis. The inventors expect that external heme depletion stops cancer cell growth but not normal cell growth; and induction sustains cell growth via intermediates accumulation in cancers, in contrast to enhanced end-product synthesis in normal cells.

TME Support of Heme Overdrive at Single Cell Resolution (Prophetic)

The flux aspect of heme overdrive (i.e., enhanced heme and intermediates trafficking), is evidenced by 1) enhanced expression of heme trafficking genes in tumors[124-127], and 2) hemoprotein gene essentiality despite that cancer cells survive without the complete biosynthesis pathway (FIG. 5). It is remarkable that even though cancers do not need to synthesize their own heme to grow (FIGS. 5 and 22), the heme/intermediates export gene is elevated across diverse tumors[124-127], thus suggesting exporting activities are of essential function. The feature of heme/intermediates flux necessitates a specialized cancer microenvironment for metabolite trafficking. However, there is currently no understanding of either the source or the fate of trafficked heme metabolites in TME.

In cancer, heme overdrive is likely fostered by the specific TME, including CAFs[174]. The inventors show that heme overdrive operates in CAFs derived from primary tumors, as assessed by protoporphyrin IX (PPIX) quantification. The inventors show that CAFs from primary lung adenocarcinoma accumulate heme intermediates (e.g., PPIX) upon induction with 5-aminolevulinate (ALA), a precursor substrate of the heme metabolic pathway, but lose this feature when the CAFs are passaged in vitro (FIG. 27A). Interestingly, the fibroblasts adjacent to the tumor also show heme overdrive, albeit to a lesser extent. (FIG. 27B). These findings indicate that TME acts as a continuum of aberrant heme metabolism. Heme overdrive in TME is likely with diffusing outer edges into normal tissues, as well as 'central zones' fostering tumor growth. As such, cancer TME exhibits its characteristics of heme overdrive.

Studying Heme Overdrive in Single Cancer Cells and CAFs (Prophetic)

To gain initial insight into liver and liver cancer heterogeneity, the inventors performed both bulk RNAseq (n=5, with bioreplictions) and single cell RNAseq with primary human liver samples from health donors (FIG. 35A). Healthy human liver exhibits clear liver zonation with peri-portal to peri-central cell populations. The inventors also analyzed a set of single cell HCC data[211,212] and found different degrees of cancer de-differentiations (FIG. 35B). By contrast, in liver cancers, primary liver function is dampened and a sub-population of aggressive cancers were found. Both whole tumor, and single cell gene expression supports heme overdrive in cancers (FIG. 35C, D). The inventors perform single cell RNAseq with in vivo HCC-PDX tumors (n=3, ~5000 scRNAseq each), with similar experimental and computational methods that generated the single cell data. The inventors identify both the malignant progenitors and other cancer associated stromal cell populations in TMEs.

To show targeting heme overdrive kills both cancer cells and CAFs, the inventors investigate isolated solid tumor derived CAFs in liver cancers. The isolated primary CAFs and matching normal fibroblast pairs are purchased (BioreclamationIVT), and for each CAF vs. normal pair, the inventors i) conduct ALA induction experiments with PPIX quantifications, ii) perform transcriptomics on cell populations with different PPIX levels, to reveal the cellular expression profiles of heme metabolic enzymes, and iii) quantify extracellular (media) vs. intracellular PPIX (cellular) levels at nanomolar resolution to show that TME supports heme overdrive and can serve as a target for future interventions.

Bait-and-Kill Strategy in HCC PDX Models (Prophetic)

Models are treated with vehicle control, ALA, candidate drug (e.g., RSL3), or a combination of ALA and candidate drug. In addition to the effect on tumor size, tumors are examined for porphyrin accumulation (fluorescence) and other markers of cell proliferation, oxidative stress, and cell death.

Heme Overdrive is Elevated in End-Stage Cancers and Linked to Overall Survival of Patients The inventors examined patient tumor biopsy data[213,214] during liver cancer progression (FIG. 36A, B). It was found that the genes of the mid-steps of the pathway, HMBS and heme metabolite trafficking FLVCR1, tracks cancer progression. While the early step gene ALAD are down regulated during liver cancer progression.

The inventors next analyzed overall survival with respect to high and low expression of the mid-step heme biosynthesis genes, ALAD and HMBS, with data from TCGA[45]. ALAD (the enzyme responsible for the $2^{nd}$ step of heme biosynthesis) and HMBS (the enzyme that catalyzes the $3^{rd}$ step) show contrasting prognostic results in overall survival, indicating the more imbalanced heme overdrive is (i.e., the larger the differences between ALAD and HMBS expression), the poorer the overall patient survival is (FIG. 36C,D).

Testing Bait-and-Kill In Vivo (Prophetic)

As noted in the previous examples, cancer cells are susceptible to 'baiting'-inducing rapid accumulation of heme precursor porphyrin metabolites (e.g., PPIX), due to the imbalanced heme biosynthesis enzymatic activities. For 'bait', cells readily take up the heme precursor ALA and bypass the first and rate-limiting step of porphyrin biosynthesis catalyzed by ALAS1. As an exogenously provided precursor, ALA has multiple import routes into the cell. The induction with ALA to induce porphyrin accumulation in cancers has been clinically and safely used in PDT for decades[66,78,142, 144-146]. The inventors designed a two-step process to engineer cancer cell metabolic death: first, 'bait' with ALA to induce PPIX accumulation to up to a few hundred-to-thousand-fold higher concentration as compared to control cells, and second, 'kill' with a compound that exploits the metabolic oxidative stress of porphyrin accumulation.

As described in the previous examples, to exploit the metabolic stress of porphyrin accumulation, the inventors treated the human leukemia HEL cell line and liver cancer cell line HC-04. ALA pre-treatment leads to accumulations of intermediates PPIX that can cause membrane lipid peroxidation. Cancer cells likely have elevated dependence on the antioxidant enzyme glutathione peroxidase 4 (GPX4), which is a phospholipid hydroperoxidase that protects cells against peroxidation. Subsequently, inhibition of GPX4 with RSL3[101-196], and/or exacerbate heme related redox stress with artemisinin[164], induces acute redox stress and cell death. Pretreatment of cancer cells with ALA increased RSL3 sensitivity at least 1000-fold (FIG. 34B,D). In contrast, ALA pretreatment did not sensitize cells to the heat shock protein inhibitor ganetespib suggesting ALA is not a general sensitizer to induction of cell death (FIG. 34E). The inventors performed the same bait-and-kill approach in primary human lung fibroblasts and found no increased sensitivity to RSL3 at either 24 hours or 48 hours (FIG. 34F,G and FIG. 18C). This non-toxic effect in normal cells stands in stark contrast with the sub-nM range of IC50 of drugs in various cancer cell lines (e.g., HEL, K562, K562-FECH-KO, K562-ALAS2-KO, BAF3-Jak2mt). Importantly, liver cancer HC-04 was killed with sub-nM drug (FIG. 34D). The previous experiments show cell growth and viability of non-cancer cells are not impaired by the bait and kill strategy.

Here, the inventors characterize bait and kill strategies in vivo by assessing the most promising bait and kill strategies in PDX models[136,137] for in vivo evaluation of RSL3, erastin, and artemisinin (exacerbating redox stress by PPIX accumulation). This includes 4 treatment arms: untreated (vehicle) and treatment with ALA, the candidate drug, and the combination of ALA and drug (the bait and kill test arm of the experiments). Tumor burden/size is measured over time as described previously. Following treatment, tumors are examined for PPIX accumulation (PPIX fluorescence) and immunohistochemical staining for cell proliferation markers (e.g., Ki-67)[151], glutathione levels[152] and lipid peroxidation[153]. RNA-seq studies are performed on candidate bait and kill strategies (control, ALA-treated, drug-treated, and the combination of the two) to evaluate if cell death involves unique transcriptomic changes that may shed light on the cellular/mechanistic effects. Subsequently to gain further mechanistic insight, the inventors perform MALDI-TOF cell-based assays to assess metabolic changes and study effects[147,148]. Results and healthy control experiments are confirmed in replicated experiments (n>=3).

Conclusion

Cancers rewire their metabolism to fuel oncogenic growth. However, therapeutic barriers exist in disrupting non-specific biochemical pathways, such as targeting cancer's glutamine addiction. The inventors target a novel cancer metabolic rewiring called 'heme overdrive', that is absent in diverse types of normal cells. The cancer specificity and inducibility (with ALA, which is safely used clinically for photodynamic therapy and imaging) of cancer heme overdrive offers elegant treatment potential to specifically kill cancer cells with minimum normal tissue toxicity.

REFERENCES

1. D'Alessandro, A., Dzieciatkowska, M., Nemkov, T. & Hansen, K. C. Red blood cell proteomics update: is there more to discover? *Blood Transfus* 15, 182-187.
2. Dean, L. in *Blood Groups and Red Cell Antigens* (National Center for Biotechnology Information (US), 2005).
3. Ponka, P., Koury, M. J. & Sheftel, A. D. in *Handbook of Porphyrin Science, Erythropoiesis, Heme and Applica-*

*tions to Biomedicine* Vol. 27 (eds G. C. Ferreira, K. M. Kadish, K. M. Smith, & R. Guilard) Ch. 129, 42-84 (World Scientific Publishing Co. Pte. Ltd., 2014).

4. Mercurio, S. et al. The heme exporter Flvcr1 regulates expansion and differentiation of committed erythroid progenitors by controlling intracellular heme accumulation. *Haematologica* 100, 720-729 (2015).
5. Kapetanaki, M. G. et al. Free heme regulates placenta growth factor through NRF2-antioxidant response signaling. *Free Radic Biol Med* 143, 300-308, (2019).
6. Hanna, D. A. et al. Heme dynamics and trafficking factors revealed by genetically encoded fluorescent heme sensors. *Proc. Natl. Acad. Sci.* (*USA*) 113, 7539-7544, (2016).
7. Ferreira, G. C. in *The Encyclopedia of Biological Chemistry* Vol. 2 (ed W. and Lane Lennarz, M. D.) 539-542 (Academic Press, 2013).
8. Carter, E. L., Gupta, N. & Ragsdale, S. W. High Affinity Heme Binding to a Heme Regulatory Motif on the Nuclear Receptor Rev-erb Leads to Its Degradation and Indirectly Regulates Its Interaction with Nuclear Receptor Corepressor. *Journal of Biological Chemistry* 291, 2196-2222, (2016).
9. Chen, J.-J. & Zhang, S. Heme-regulated eIF2α kinase in erythropoiesis and hemoglobinopathies. *Blood* 134, 1697-1707, (2019).
10. Fleischhacker, A. S., Carter, E. L. & Ragsdale, S. W. Redox Regulation of Heme Oxygenase-2 and the Transcription Factor, Rev-Erb, Through Heme Regulatory Motifs. *Antioxidants & Redox Signaling* 29, 1841-1857, (2017).
11. Kato, H. et al. Infection perturbs Bach2- and Bach1-dependent erythroid lineage 'choice' to cause anemia. *Nature Immunology* 19, 1059-1070, doi:10.1038/s41590-018-0202-3 (2018).
12. Motomura, T. et al. Crystal structure and redox properties of a novel cyanobacterial heme protein with a His/Cys heme axial ligation and a Per-Arnt-Sim (PAS)-like domain. *Journal of Biological Chemistry* 292, 9599-9612, doi:10.1074/jbc.M116.746263 (2017).
13. Nishinaga, M. et al. Heme controls the structural rearrangement of its sensor protein mediating the hemolytic bacterial survival. Communications *Biology* 4, 467, doi:10.1038/s42003-021-01987-5 (2021).
14. Quick-Cleveland, J. et al. The DGCR8 RNA-Binding Heme Domain Recognizes Primary MicroRNAs by Clamping the Hairpin. *Cell Reports* 7, 1994-2005, (2014).
15. Shimizu, T., Lengalova, A., Martínek, V. & Martinková, M. Heme: emergent roles of heme in signal transduction, functional regulation and as catalytic centres. *Chemical Society Reviews* 48, 5624-5657, (2019).
16. Weitz, S. H. et al. Fe(III) heme sets an activation threshold for processing distinct groups of pri-miRNAs in mammalian cells. *bioRxiv,* 2020.2002.2018.955294, (2020).
17. Yamawaki, T. et al. Regulatory Switching by Concerted Motions on the Microsecond Time Scale of the Oxygen Sensor Protein FixL. *The Journal of Physical Chemistry B* 125, 6847-6856, (2021).
18. Yang, J. et al. A Novel Heme-Regulatory Motif Mediates Heme-Dependent Degradation of the Circadian Factor Period 2. *Molecular and Cellular Biology* 28, 4697-4711, (2008).
19. Yi, L., Morgan, J. T. & Ragsdale, S. W. Identification of a Thiol/Disulfide Redox Switch in the Human BK Channel That Controls Its Affinity for Heme and CO. *Journal of Biological Chemistry* 285, 20117-20127, (2010).
20. Zenke-Kawasaki, Y. et al. Heme Induces Ubiquitination and Degradation of the Transcription Factor Bach1. *Molecular and Cellular Biology* 27, 6962-6971, (2007).
21. Zheng, H., Williams, J. T., Aleiwi, B., Ellsworth, E. & Abramovitch, R. B. Inhibiting *Mycobacterium tuberculosis* DosRST Signaling by Targeting Response Regulator DNA Binding and Sensor Kinase Heme. *ACS Chemical Biology* 15, 52-62, (2020).
22. Hunter, G. A. & Ferreira, G. C. Molecular enzymology of 5-Aminolevulinate synthase, the gatekeeper of heme biosynthesis. *Biochim. Biophys. Acta* 1814, 1467-1473, (2011).
23. Cao, J. Y. & Dixon, S. J. Mechanisms of ferroptosis. *Cell Mol. Life Sci.* 73, 2195-2209 (2016).
24. Malik, Z. & Djaldetti, M. Cytotoxic effect of hemin and protoporphyrin on chronic lymphocytic leukemia lymphocytes. *Exp. Hematol.* 8, 867-879 (1980).
25. Tibullo, D. et al. Nuclear Translocation of Heme Oxygenase-1 Confers Resistance to Imatinib in Chronic Myeloid Leukemia Cells. *Curr. Pharmac. Design* 19, 2765-2770, (2013).
26. Levine, A. J. & Puzio-Kuter, A. M. The control of the metabolic switch in cancers by oncogenes and tumor suppressor genes. *Science* 330, 1340-1344, (2010).
27. Luengo, A., Gui, D. Y. & Vander Heiden, M. G. Targeting Metabolism for Cancer Therapy. *Cell Chem Biol* 24, 1161-1180, doi:10.1016/j.chembiol.2017.08.028 (2017).
28. Martinez-Outschoorn, U. E., Peiris-Pages, M., Pestell, R. G., Sotgia, F. & Lisanti, M. P. Cancer metabolism: a therapeutic perspective. *Nat Rev Clin Oncol* 14, 11-31, (2017).
29. Steinberg, P. Red Meat-Derived Nitroso Compounds, Lipid Peroxidation Products and Colorectal Cancer. *Foods* 8, (2019).
30. Fiorito, V., Chiabrando, D., Petrillo, S., Bertino, F. & Tolosano, E. The Multifaceted Role of Heme in Cancer. *Frontiers in Oncology* 9, (2020).
31. Martin, O. C. B. et al. Targeting Colon Luminal Lipid Peroxidation Limits Colon Carcinogenesis Associated with Red Meat Consumption. *Cancer Prev Res* (*Phila*) 11, 569-580, (2018).
32. Sohoni, S. et al. Elevated Heme Synthesis and Uptake Underpin Intensified Oxidative Metabolism and Tumorigenic Functions in Non-Small Cell Lung Cancer Cells. *Cancer Research* 79, 2511-2525, (2019).
33. Ijssennagger, N. et al. Gut microbiota facilitates dietary heme-induced epithelial hyperproliferation by opening the mucus barrier in colon. *Proceedings of the National Academy of Sciences* 112, 10038-10043, (2015).
34. Fiorito, V. et al. The heme synthesis-export system regulates the tricarboxylic acid cycle flux and oxidative phosphorylation. *Cell Reports* 35, 109252, (2021).
35. Vander Heiden, M. G., Cantley, L. C. & Thompson, C. B. Understanding the Warburg effect: the metabolic requirements of cell proliferation. *Science* 324, 1029-1033, (2009).
36. Wise, D. R. & Thompson, C. B. Glutamine addiction: a new therapeutic target in cancer. *Trends Biochem Sci* 35, 427-433, (2010).
37. Cluntun, A. A., Lukey, M. J., Cerione, R. A. & Locasale, J. W. Glutamine Metabolism in Cancer: Understanding the Heterogeneity. *Trends Cancer* 3, 169-180, (2017).
38. Meyers, R. M. et al. Computational correction of copy number effect improves specificity of CRISPR-Cas9 essentiality screens in cancer cells. *Nat Genet* 49, 1779-1784, (2017).

39. Nguyen, Tuan A. et al. Functional Anatomy of the Human Microprocessor. *Cell* 161, 1374-1387, (2015).

40. Fratz, E. J., Stojanovski, B. M. & Ferreira, G. C. in *Handbook of Porphyrin Science, Heme Biochemistry* Vol. 26 *Heme Biochemistry* (eds G. C. Ferreira, K. M. Kadish, K. M. Smith, & R. Guilard) Ch. 119, 3-68 (World Scientific Publishing Co. Pte. Ltd., 2014).

41. Bishop, D. F., Henderson, A. S. & Astrin, K. H. Human δ-aminolevulinate synthase: Assignment of the housekeeping gene to 3p21 and the erythroid-specific gene to the X chromosome. *Genomics* 7, 207-214, (1990).

42. Tsherniak, A. et al. Defining a Cancer Dependency Map. *Cell* 170, 564-576 e516, (2017).

43. Ardlie, K. The Genotype-Tissue Expression (GTEx) pilot analysis: Multitissue 1252 gene regulation in humans. *Science,* 648-660.

44. Lonsdale, J. et al. The Genotype-Tissue Expression (GTEx) project. *Nature Genetics* 45, 580-585, (2013).

45. Chang, K. et al. The Cancer Genome Atlas Pan-Cancer analysis project. *Nature Genetics* 45, 1113-1120, (2013).

46. Dempster, J. M. et al. Agreement between two large pan-cancer CRISPR-Cas9 gene dependency data sets. *Nat Commun* 10, 5817, (2019).

47. Pacini, C. et al. Integrated cross-study datasets of genetic dependencies in cancer. *Nat Commun* 12, 1661, (2021).

48. Zhu, X. G. et al. Functional Genomics In Vivo Reveal Metabolic Dependencies of Pancreatic Cancer Cells. *Cell Metab* 33, 211-221.e216, (2021).

49. Tang, Z. et al. GEPIA: a web server for cancer and normal gene expression profiling and interactive analyses. *Nucleic Acids Research* 45, W98-W102, (2017).

50. Tolosano, E., Fagoonee, S., Morello, N., Vinchi, F. & Fiorito, V. Heme scavenging and the other facets of hemopexin. *Antioxid Redox Signal* 12, 305-320, (2010).

51. Canesin, G. et al. Scavenging of Labile Heme by Hemopexin Is a Key Checkpoint in Cancer Growth and Metastases. *Cell Rep* 32, 108181, (2020).

52. Elia, I. & Haigis, M. C. Metabolites and the tumour microenvironment: from cellular mechanisms to systemic metabolism. *Nat Metab* 3, 21-32, (2021).

53. Hooda, J. et al. Enhanced Heme Function and Mitochondrial Respiration Promote the Progression of Lung Cancer Cells. *PLOS ONE* 8, e63402, (2013).

54. Ma, Y. et al. The relationship between early embryo development and tumourigenesis. *J Cell Mol Med* 14, 2697-2701, (2010).

55. Smith, D. G. & Sturmey, R. G. Parallels between embryo and cancer cell metabolism. *Biochem Soc Trans* 41, 664-669, (2013).

56. Li, L. et al. Single-Cell RNA-Seq Analysis Maps Development of Human Germline Cells and Gonadal Niche Interactions. *Cell Stem Cell* 20, 891-892, (2017).

57. Yan, L. et al. Single-cell RNA-Seq profiling of human preimplantation embryos and embryonic stem cells. *Nat Struct Mol Biol* 20, 1131-1139, (2013).

58. Penzo-Méndez, A., Dy, P., Pallavi, B. & Lefebvre, V. Generation of mice harboring a Sox4 conditional null allele. *Genesis* 45, 776-780, (2007).

59. Sasai, K. et al. Targeted disruption of Aurora A causes abnormal mitotic spindle assembly, chromosome misalignment and embryonic lethality. *Oncogene* 27, 4122-4127, (2008).

60. Oka, T. et al. Metabolic abnormalities in adult T-cell leukemia/lymphoma and induction of specific leukemic cell death using photodynamic therapy. *Scientific Reports* 8, 14979, (2018).

61. Krieg, R. C., Messmann, H., Rauch, J., Seeger, S. & Knuechel, R. Metabolic characterization of tumor cell-specific protoporphyrin IX accumulation after exposure to 5-aminolevulinic acid in human colonic cells. *Photochem Photobiol* 76, 518-525, (2002).

62. Maher, S. P. et al. An adaptable soft-mold embossing process for fabricating optically-accessible, microfeature-based culture systems and application toward liver stage antimalarial compound testing. *Lab Chip* 20, 1124-1139, (2020).

63. Egan, E. S. et al. Malaria. A forward genetic screen identifies erythrocyte CD55 as essential for *Plasmodium falciparum*: invasion. *Science* 348, 711-714, (2015).

64. Villeneuve, L. Ex vivo photodynamic purging in chronic myelogenous leukaemia and other neoplasias with rhodamine derivatives. *Biotechnol Appl Biochem* 30, 1-17 (1999).

65. de Lima, M. & Shpall, E. J. Ex-vivo purging of hematopoietic progenitor cells. *Curr Hematol Rep* 3, 257-264 (2004).

66. Kobuchi, H. et al. Mitochondrial localization of ABC transporter ABCG2 and its function in 5-aminolevulinic acid-mediated protoporphyrin IX accumulation. *PLoS One* 7, e50082, (2012).

67. Taketani, S., Inazawa, J., Nakahashi, Y., Abe, T. & Tokunaga, R. Structure of the human ferrochelatase gene. Exon/intron gene organization and location of the gene to chromosome 18. *Eur J Biochem* 205, 217-222, (1992).

68. Whitcombe, D. M. et al. Assignment of the human ferrochelatase gene (FECH) and a locus for protoporphyria to chromosome 18q22. *Genomics* 11, 1152-1154, (1991).

69. Chenais, B., Andriollo, M., Guiraud, P., Belhoussine, R. & Jeannesson, P. Oxidative stress involvement in chemically induced differentiation of K562 cells. *Free Radic Biol Med* 28, 18-27, (2000).

70. Merryweather-Clarke, A. T. et al. Distinct gene expression program dynamics during erythropoiesis from human induced pluripotent stem cells compared with adult and cord blood progenitors. *BMC Genomics* 17, 817, (2016).

71. Merryweather-Clarke, A. T. et al. Global gene expression analysis of human erythroid progenitors. *Blood* 117, e96-108, (2011).

72. Tirosh, I. et al. Dissecting the multicellular ecosystem of metastatic melanoma by single-cell RNA-seq. *Science* 352, 189-196, (2016).

73. Wu, S. Z. et al. Stromal cell diversity associated with immune evasion in human triple-negative breast cancer. *The EMBO Journal* 39, e104063, (2020).

74. Manwani, D. & Bieker, J. J. The erythroblastic island. *Curr Top Dev Biol* 82, 23-53, (2008).

75. Socolovsky, M. Exploring the erythroblastic island. *Nat Med* 19, 399-401, (2013).

76. Lukanidin, E. & Sleeman, J. P. Building the niche: the role of the S100 proteins in metastatic growth. *Semin Cancer Biol* 22, 216-225, (2012).

77. Icard, P. & Lincet, H. [The cancer tumor: a metabolic parasite?]. *Bull Cancer* 100, 427-433, (2013).

78. Li, X. Q. et al. NAMPT and NAPRT, Key Enzymes in NAD Salvage Synthesis Pathway, Are of Negative Prognostic Value in Colorectal Cancer. *Front Oncol* 9, 736, (2019).

79. Krammer, B. & Plaetzer, K. ALA and its clinical impact, from bench to bedside. *Photochem Photobiol Sci* 7, 283-289, (2008).

80. Fisher, C. J. et al. ALA-PpIX mediated photodynamic therapy of malignant gliomas augmented by hypothermia. *PLoS One* 12, e0181654, (2017).

81. Fujishiro, T. et al. 5-Aminolevulinic acid-mediated photodynamic therapy can target human glioma stem-like cells refractory to antineoplastic agents. *Photodiagnosis Photodyn Ther* 24, 58-68, (2018).

82. Shan, L. et al. Increased hemoglobin and heme in MALDI-TOF MS analysis induce ferroptosis and promote degeneration of herniated human nucleus pulposus. *Mol Med* 27, 103, (2021).

83. Alexandrova, E. M. et al. Improving survival by exploiting tumour dependence on stabilized mutant p53 for treatment. *Nature* 523, 352-356, (2015).

84. Kessel, D. Photodynamic Therapy: A Brief History. *J Clin* Med 8, 1581, (2019).

85. Hausmann, W. *Über die sensibilisierende Wirkung des Hämatoporphyrins.* (1913).

86. Toh, T. B., Lim, J. J. & Chow, E. K. Epigenetics in cancer stem cells. *Mol Cancer* 16, 29, (2017).

87. Thakur, C. & Chen, F. Connections between metabolism and epigenetics in cancers. *Semin Cancer Biol* 57, 52-58, (2019).

88. Campbell, S. L. & Wellen, K. E. Metabolic Signaling to the Nucleus in Cancer. *Mol Cell* 71, 398-408, (2018).

89. Liao, R. et al. Discovering How Heme Controls Genome Function Through Heme-omics. *Cell Rep* 31, 107832, (2020).

90. Kaasik, K. & Lee, C. C. Reciprocal regulation of haem biosynthesis and the circadian clock in mammals. *Nature* 430, 467-471, (2004).

91. Wang, T. et al. An Analysis of the Multifaceted Roles of Heme in the Pathogenesis of Cancer and Related Diseases. *Cancers* (*Basel*) 13, (2021).

92. Mense, S. M. & Zhang, L. Heme: a versatile signaling molecule controlling the activities of diverse regulators ranging from transcription factors to MAP kinases. *Cell Research* 16, 681-692, (2006).

93. Finicle, B. T., Jayashankar, V. & Edinger, A. L. Nutrient scavenging in cancer. *Nature Reviews Cancer* 18, 619-633, (2018).

94. Bartoschek, M. et al. Spatially and functionally distinct subclasses of breast cancer-associated fibroblasts revealed by single cell RNA sequencing. *Nat Commun* 9, 5150, (2018).

95. Sahai, E. et al. A framework for advancing our understanding of cancer-associated fibroblasts. *Nat Rev Cancer* 20, 174-186, doi:10.1038/s41568-019-0238-1 (2020).

96. Chen, X. & Song, E. Turning foes to friends: targeting cancer-associated fibroblasts. *Nat Rev Drug Discov* 18, 99-115, (2019).

97. Kalluri, R. The biology and function of fibroblasts in cancer. *Nat Rev Cancer* 16, 582-598, (2016).

98. Maitra, D. et al. Porphyrin-Induced Protein Oxidation and Aggregation as a Mechanism of *Porphyria*-Associated Cell Injury. *Cell Mol Gastroenterol Hepatol* 8, 535-548, (2019).

99. A. J. Aguirre et al., Genomic Copy Number Dictates a Gene-Independent Cell Response to CRISPR/Cas9 Targeting. *Cancer Discov* 6, 914-929 (2016).

100. E. Kim, T. Hart, Improved analysis of CRISPR fitness screens and reduced off-target effects with the BAGEL2 gene essentiality classifier. *Genome Med* 13, 2 (2021).

101. W. S. Yang et al., Regulation of ferroptotic cancer cell death by GPX4. *Cell* 156, 317-331 (2014).

102. J. Sattabongkot et al., Establishment of a human hepatocyte line that supports in vitro development of the exo-erythrocytic stages of the malaria parasites *Plasmodium falciparum* and *P. vivax*. *Am J Trop Med Hyg* 74, 708-715 (2006).

103. Sassa, S. & Kappas, A. Hereditary Tyrosinemia and the Heme Biosynthetic Pathway. *The Journal of Clinical Investigation* 71, 625-634, (1983).

104. Di Pierro, E. et al. Laboratory diagnosis of porphyria. *Diagnostics* 11, 1343 (2021).

105. Phillips, J. D. Heme biosynthesis and the porphyrias. *Molecular genetics and metabolism* 128, 164-177 (2019).

106. Smith, K. M. *Porphyrins and metalloporphyrins: a new edition based on the original volume* by J. E. Falk. (Elsevier Scientific Pub. Co., 1975).

107. Franco, R. et al. Characterization of the Iron-binding Site in Mammalian Ferrochelatase by Kinetic and Mossbauer Methods. *Journal of Biological Chemistry* 270, 26352-26357 (1995).

108. Gong, J., Hunter, G. A. & Ferreira, G. C. Aspartate-279 in Aminolevulinate Synthase Affects Enzyme Catalysis through Enhancing the Function of the Pyridoxal 5'-Phosphate Cofactor. *Biochemistry* 37, 3509-3517, (1998).

109. Hunter, G. A. & Ferreira, G. C. A Continuous Spectrophotometric Assay for 5-Aminolevulinate Synthase That Utilizes Substrate Cycling. *Analytical Biochemistry* 226, 221-224, (1995).

110. Hunter, G. A. & Ferreira, G. C. Lysine-313 of 5-Aminolevulinate Synthase Acts as a General Base during Formation of the Quinonoid Reaction Intermediates. *Biochemistry* 38, 3711-3718, (1999).

111. Hunter, G. A. & Ferreira, G. C. Pre-steady-state Reaction of 5-Aminolevulinate Synthase: EVIDENCE FOR A RATE-DETERMINING PRODUCT RELEASE. *Journal of Biological Chemistry* 274, 12222-12228, (1999).

112. D Hunter, G. A. & Ferreira, G. C. Identification and Characterization of an Inhibitory Metal Ion-binding Site in Ferrochelatase. *Journal of Biological Chemistry* 285, 41836-41842, (2010).

113. Hunter, G. A., Zhang, J. & Ferreira, G. C. Transient Kinetic Studies Support Refinements to the Chemical and Kinetic Mechanisms of Aminolevulinate Synthase. *Journal of Biological Chemistry* 282, 23025-23035, (2007).

114. Lloyd, S. G. et al. Functional Necessity and Physicochemical Characteristics of the [2Fe-2S] Cluster in Mammalian Ferrochelatase. *Journal of the American Chemical Society* 118, 9892-9900, (1996).

115. Shi, Z. & Ferreira, G. C. A continuous anaerobic fluorimetric assay for ferrochelatase by monitoring porphyrin disappearance. *Analytical Biochemistry* 318, 18-24, (2003).

116. Stojanovski, B. M. & Ferreira, G. C. Asn-150 of Murine Erythroid 5-Aminolevulinate Synthase Modulates the Catalytic Balance between the Rates of the Reversible Reaction. *Journal of Biological Chemistry* 290, 30750-30761, (2015).

117. Zhang, J. & Ferreira, G. C. Transient State Kinetic Investigation of 5-Aminolevulinate Synthase Reaction Mechanism. *Journal of Biological Chemistry* 277, 44660-44669, (2002).

118. Zhou, W. et al. DNA methylation loss in late-replicating domains is linked to mitotic cell division. *Nature Genetics* 50, 591-602, (2018).

119. Schep, A. N., Wu, B., Buenrostro, J. D. & Greenleaf, W. J. chromVAR: inferring transcription-factor-associated accessibility from single-cell epigenomic data. *Nature Methods* 14, 975-978, (2017).

120. Yu, G., Wang, L.-G. & He, Q.-Y. ChIPseeker: an R/Bioconductor package for ChIP peak annotation, comparison and visualization. *Bioinformatics* 31, 2382-2383, (2015).

121. Love, M. I., Huber, W. & Anders, S. Moderated estimation of fold change and dispersion for RNA-seq data with DESeq2. *Genome Biology* 15, 550, (2014).

122. Lin, T.-Y. et al. Fibroblast dedifferentiation as a determinant of successful regeneration. *Developmental Cell* 56, 1541-1551.e1546, (2021).

123. Sahu, B. et al. Human cell transformation by combined lineage conversion and oncogene expression. *Oncogene* 40, 5533-5547, (2021).

124. Han, Y., Wang, X., Mao, E., Shen, B. & Huang, L. lncRNA FLVCR1-AS1 drives colorectal cancer progression via modulation of the miR-381/RAP2A axis. *Mol Med Rep* 23, (2021).

125. Pan, Z. et al. LncRNA FLVCR1-AS1 promotes proliferation, migration and activates Wnt/β-catenin pathway through miR-381-3p/CTNNB1 axis in breast cancer. *Cancer Cell Int* 20, 214, (2020).

126. Yan, Z., Zhang, W., Xiong, Y., Wang, Y. & Li, Z. Long noncoding RNA FLVCR1-AS1 aggravates biological behaviors of glioma cells via targeting miR-4731-5p/E2F2 axis. *Biochem Biophys Res Commun* 521, 716-720, (2020).

127. Zhou, S. et al. FLVCR1 Predicts Poor Prognosis and Promotes Malignant Phenotype in Esophageal Squamous Cell Carcinoma via Upregulating CSE1L. *Front Oncol* 11, 660955, (2021).

128. Korolnek, T. & Hamza, I. Like iron in the blood of the people: the requirement for heme trafficking in iron metabolism. *Front. Pharm.* 5, 1-13, (2014).

129. Korolnek, T. & Hamza, I. Macrophages and iron trafficking at the birth and death of red cells. *Blood* 125, 2893-2897, (2015).

130. Schultz, I. J., Chen, C., Paw, B. H. & Hamza, I. Iron and Porphyrin Trafficking in Heme Biogenesis. *Journal of Biological Chemistry* 285, 26753-26759, (2010).

131. Hwang, W. L. et al. Single-nucleus and spatial transcriptomics of archival pancreatic cancer reveals multi-compartment reprogramming after neoadjuvant treatment. *bioRxiv*, 2020.2008.2025.267336, (2020).

132. Izar, B. et al. A single-cell landscape of high-grade serous ovarian cancer. *Nature Medicine* 26, 1271-1279, (2020).

133. Kazi, A. et al. Global Phosphoproteomics Reveal CDK Suppression as a Vulnerability to KRas Addiction in Pancreatic Cancer. *Clinical Cancer Research* 27, 4012-4024, (2021).

134. Kazi, A. et al. Dual Farnesyl and Geranylgeranyl Transferase Inhibitor Thwarts Mutant KRAS-Driven Patient-Derived Pancreatic Tumors. *Clin Cancer Res* 25, 5984-5996, (2019).

135. Kazi, A. et al. GSK3 suppression upregulates β-catenin and c-Myc to abrogate KRas-dependent tumors. *Nat Commun* 9, 5154, (2018).

136. Driehuis, E. et al. Pancreatic cancer organoids recapitulate disease and allow personalized drug screening. *Proceedings of the National Academy of Sciences* 116, 26580-26590, (2019).

137. Piro, G. et al. Pancreatic Cancer Patient-Derived Organoid Platforms: A Clinical Tool to Study Cell- and Non-Cell-Autonomous Mechanisms of Treatment Response. *Front Med* (*Lausanne*) 8, 793144, (2021).

138. Valdés, P. A. et al. δ-aminolevulinic acid-induced protoporphyrin IX concentration correlates with histopathologic markers of malignancy in human gliomas: the need for quantitative fluorescence-guided resection to identify regions of increasing malignancy. *Neuro Oncol* 13, 846-856, (2011).

139. Andersen, M. K. et al. Spatial differentiation of metabolism in prostate cancer tissue by MALDI-TOF MSI. *Cancer & Metabolism* 9, 9, (2021).

140. Ren, X. et al. Reconstruction of cell spatial organization from single-cell RNA sequencing data based on ligand-receptor mediated self-assembly. *Cell Research* 30, 763-778, (2020).

141. Satija, R., Farrell, J. A., Gennert, D., Schier, A. F. & Regev, A. Spatial reconstruction of single-cell gene expression data. *Nature Biotechnology* 33, 495-502, (2015).

142. Hagiya, Y. et al. Pivotal roles of peptide transporter PEPT1 and ATP-binding cassette (ABC) transporter ABCG2 in 5-aminolevulinic acid (ALA)-based photocytotoxicity of gastric cancer cells in vitro. *Photodiagnosis Photodyn Ther* 9, 204-214, (2012).

143. Li, X. Q. et al. NAMPT and NAPRT, Key Enzymes in NAD Salvage Synthesis Pathway, Are of Negative Prognostic Value in Colorectal Cancer. *Front Oncol* 9, 736, (2019).

144. Manceau, H. et al. TSPO2 translocates 5-aminolevulinic acid into human erythroleukemia cells. *Biol Cell* 112, 113-126, (2020).

145. Nakayama, T. et al. Dormant cancer cells accumulate high protoporphyrin IX levels and are sensitive to 5-aminolevulinic acid-based photodynamic therapy. *Sci Rep* 6, 36478, (2016).

146. Wang, W. et al. Enhancement of 5-aminolevulinic acid-based fluorescence detection of side population-defined glioma stem cells by iron chelation. *Sci Rep* 7, 42070, (2017).

147. Weigt, D. et al. Mechanistic MALDI-TOF Cell-Based Assay for the Discovery of Potent and Specific Fatty Acid Synthase Inhibitors. *Cell Chem Biol* 26, 1322-1331.e1324, (2019).

148. Weigt, D., Sammour, D. A., Ulrich, T., Munteanu, B. & Hopf, C. Automated analysis of lipid drug-response markers by combined fast and high-resolution whole cell MALDI mass spectrometry biotyping. *Scientific Reports* 8, 11260, (2018).

149. Griner, L. N., McGraw, K. L., Johnson, J. O., List, A. F. & Reuther, G. W. JAK2-V617F-mediated signalling is dependent on lipid rafts and statins inhibit JAK2-V617F-dependent cell growth. *Br J Haematol* 160, 177-187, (2013).

150. Mazzacurati, L. et al. The pan-PIM inhibitor INCB053914 displays potent synergy in combination with ruxolitinib in models of MPN. *Blood Adv* 3, 3503-3514, (2019).

151. Menon, S. S., Guruvayoorappan, C., Sakthivel, K. M. & Rasmi, R. R. Ki-67 protein as a tumour proliferation marker. *Clin Chim Acta* 491, 39-45, (2019).

152. Rahman, I., Kode, A. & Biswas, S. K. Assay for quantitative determination of glutathione and glutathione disulfide levels using enzymatic recycling method. *Nat Protoc* 1, 3159-3165, (2006).

153. Tsikas, D. Assessment of lipid peroxidation by measuring malondialdehyde (MDA) and relatives in biological samples: Analytical and biological challenges. *Anal Biochem* 524, 13-30, (2017).

154. Afonso, S., Vanore, G. & Batlle, A. Protoporphyrin IX and oxidative stress. *Free Radic Res* 31, 161-170, (1999).

155. Doll, S. et al. FSP1 is a glutathione-independent ferroptosis suppressor. *Nature* 575, 693-698, (2019).
156. Dixon, S. J. et al. Ferroptosis: an iron-dependent form of nonapoptotic cell death. *Cell* 149, 1060-1072, (2012).
157. Algorri, J. F., Ochoa, M., Roldán-Varona, P., Rodríguez-Cobo, L. & López-Higuera, J. M. Photodynamic Therapy: A Compendium of Latest Reviews. *Cancers* 13, 4447 (2021).
158. Nakamura, Y. et al. Cerenkov Radiation-Induced Photoimmunotherapy with (18)F-FDG. *J Nucl Med* 58, 1395-1400, (2017).
159. Kotagiri, N. et al. Radionuclides transform chemotherapeutics into phototherapeutics for precise treatment of disseminated cancer. *Nature Communications* 9, 275, (2018).
160. Venneti, S. et al. Glutamine-based PET imaging facilitates enhanced metabolic evaluation of gliomas in vivo. *Sci Transl Med* 7, 274ra217, (2015).
161. Le, D., Dhamecha, D., Gonsalves, A. & Menon, J. U. Ultrasound-Enhanced Chemiluminescence for Bioimaging. *Frontiers in Bioengineering and Biotechnology* 8, (2020).
162. Laptev, R., Nisnevitch, M., Siboni, G., Malik, Z. & Firer, M. A. Intracellular chemiluminescence activates targeted photodynamic destruction of leukaemic cells. *British Journal of Cancer* 95, 189-196, (2006).
163. Zhang, C. J. et al. Mechanism-Guided Design and Synthesis of a Mitochondria-Targeting Artemisinin Analogue with Enhanced Anticancer Activity. *Angew Chem Int Ed Engl* 55, 13770-13774, (2016).
164. Wang, J. et al. Haem-activated promiscuous targeting of artemisinin in *Plasmodium falciparum. Nature Communications* 6, 10111, (2015).
165. Chen, G.-Q. et al. Artemisinin compounds sensitize cancer cells to ferroptosis by regulating iron homeostasis. *Cell Death & Differentiation* 27, 242-254, (2020).
166. Wan, L., Pantel, K. & Kang, Y. Tumor metastasis: moving new biological insights into the clinic. *Nat Med* 19, 1450-1464, (2013).
167. Hirsch, F. R. et al. Lung cancer: current therapies and new targeted treatments. *Lancet* 389, 299-311, (2017).
168. Arber, D. A. et al. The 2016 revision to the World Health Organization classification of myeloid neoplasms and acute leukemia. *Blood* 127, 2391-2405, (2016).
169. Prasad, V. Perspective: The precision-oncology illusion. *Nature* 537, S63-S63, (2016).
170. Marquart, J., Chen, E. Y. & Prasad, V. Estimation of the Percentage of US Patients With Cancer Who Benefit From Genome-Driven Oncology. *JAMA Oncol* 4, 1093-1098, (2018).
171. Thai, A. A., Solomon, B. J., Sequist, L. V., Gainor, J. F. & Heist, R. S. Lung cancer. *Lancet* 398, 535-554, (2021).
172. The, L. Lung cancer: some progress, but still a lot more to do. *Lancet* 394, 1880, (2019).
173. Lin, S. et al. An in vivo CRISPR screening platform for prioritizing therapeutic targets in AML. *bioRxiv,* 2020.2012.2028.424340, (2020).
174. Ping, Q. et al. Cancer-associated fibroblasts: overview, progress, challenges, and directions. *Cancer Gene Therapy* 28, 984-999, (2021).
175. Zilionis, R. et al. Single-Cell Transcriptomics of Human and Mouse Lung Cancers Reveals Conserved Myeloid Populations across Individuals and Species. *Immunity* 50, 1317-1334.e1310, (2019).
176. Dächert, J., Schoeneberger, H., Rohde, K. & Fulda, S. RSL3 and Erastin differentially regulate redox signaling to promote Smac mimetic-induced cell death. *Oncotarget* 7, 63779-63792, (2016).
177. Predina, J. D. et al. Evaluation of Aminolevulinic Acid-Derived Tumor Fluorescence Yields Disparate Results in Murine and Spontaneous Large Animal Models of Lung Cancer. *Scientific Reports* 9, 7629, (2019).
178. Jiang, C. et al. A CRISPR screen identifies redox vulnerabilities for KEAP1/NRF2 mutant non-small cell lung cancer. *Redox Biol* 54, 102358, (2022).
179. Lin, S. et al. Fascin promotes lung cancer growth and metastasis by enhancing glycolysis and PFKFB3 expression. *Cancer Lett* 518, 230-242, (2021).
180. Wu, W. et al. Inhibition of Tumor Growth and Metastasis in Non-Small Cell Lung Cancer by LY2801653, an Inhibitor of Several Oncokinases, Including MET. *Clinical Cancer Research* 19, 5699-5710, (2013).
181. Wu, W. et al. Targeted therapy of orthotopic human lung cancer by combined vascular endothelial growth factor and epidermal growth factor receptor signaling blockade. *Molecular Cancer Therapeutics* 6, 471-483, (2007).
182. Fratz, E. J., Hunter, G. A. & Ferreira, G. C. Expression of Murine 5-Aminolevulinate Synthase Variants Causes Protoporphyrin IX Accumulation and Light-Induced Mammalian Cell Death. *PLOS ONE* 9, e93078, (2014).
183. Stoller, J. K. The Challenge of Rare Diseases. *Chest* 153, 1309-1314, (2018).
184. Landgren, O. et al. Agent Orange Exposure and Monoclonal Gammopathy of Undetermined Significance: An Operation Ranch Hand Veteran Cohort Study. *JAMA Oncol* 1, 1061-1068, (2015).
185. Mescher, C. et al. The impact of Agent Orange exposure on prognosis and management in patients with chronic lymphocytic leukemia: a National Veteran Affairs Tumor Registry Study. *Leuk Lymphoma* 59, 1348-1355, (2018).
186. Wen, W. Q. et al. Paternal military service and risk for childhood leukemia in offspring. *Am J Epidemiol* 151, 231-240, (2000).
187. Wang, J. et al. Haem-activated promiscuous targeting of artemisinin in *Plasmodium falciparum. Nature Communications* 6, 10111, (2015).
188. Boddu, P. et al. Erythroleukemia-historical perspectives and recent advances in diagnosis and management. *Blood Rev* 32, 96-105, (2018).
189. Weinberg, O. K. & Arber, D. A. Erythroleukemia: an Update. *Curr Oncol Rep* 23, 69, (2021).
190. Asher, S., McLornan, D. P. & Harrison, C. N. Current and future therapies for myelofibrosis. *Blood Rev* 42, 100715, (2020).
191. Gangat, N. & Tefferi, A. Myelofibrosis biology and contemporary management. *Br J Haematol* 191, 152-170, (2020).
192. Baccin, C. et al. Combined single-cell and spatial transcriptomics reveal the molecular, cellular and spatial bone marrow niche organization. *Nature Cell Biology* 22, 38-48, (2020).
193. Dolgalev, I. & Tikhonova, A. N. Connecting the Dots: Resolving the Bone Marrow Niche Heterogeneity. *Frontiers in Cell and Developmental Biology* 9, (2021).
194. Tikhonova, A. N. et al. The bone marrow microenvironment at single-cell resolution. *Nature* 569, 222-228, (2019).

195. Watts, J. M. & Tallman, M. S. Acute promyelocytic leukemia: what is the new standard of care? *Blood Rev* 28, 205-212, (2014).

196. Chen, X., Kang, R., Kroemer, G. & Tang, D. Broadening horizons: the role of ferroptosis in cancer. *Nat Rev Clin Oncol* 18, 280-296, (2021).

197. Ying, W. et al. Ganetespib, a unique triazolone-containing Hsp90 inhibitor, exhibits potent antitumor activity and a superior safety profile for cancer therapy. *Mol Cancer Ther* 11, 475-484, (2012).

198. Yang, W. S. & Stockwell, B. R. Synthetic lethal screening identifies compounds activating iron-dependent, nonapoptotic cell death in oncogenic-RAS-harboring cancer cells. *Chem Biol* 15, 234-245, (2008).

199. Forner, A., Reig, M. & Bruix, J. Hepatocellular carcinoma. *Lancet* 391, 1301-1314, (2018).

200. Williams, V. F., Taubman, S. B. & Stahlman, S. Non-alcoholic fatty liver disease (NAFLD), active component, U.S. Armed Forces, 2000-2017. *Msmr* 26, 2-11 (2019).

201. Nasir, A. et al. Markedly Increased Rate of Primary Liver Malignancies at Autopsy in Male US Veterans. *Clinical Gastroenterology and Hepatology* 15, 316-318, (2017).

202. Bruix, J., Han, K. H., Gores, G., Llovet, J. M. & Mazzaferro, V. Liver cancer: Approaching a personalized care. *J Hepatol* 62, S144-156, (2015).

203. Llovet, J. M., Montal, R., Sia, D. & Finn, R. S. Molecular therapies and precision medicine for hepatocellular carcinoma. *Nat Rev Clin Oncol* 15, 599-616, (2018).

204. Anwanwan, D., Singh, S. K., Singh, S., Saikam, V. & Singh, R. Challenges in liver cancer and possible treatment approaches. *Biochim Biophys Acta Rev Cancer* 1873, 188314-188314, (2020).

205. Llovet, J. M. et al. Sorafenib in Advanced Hepatocellular Carcinoma. *New England Journal of Medicine* 359, 378-390, (2008).

206. Bruix, J. et al. Regorafenib for patients with hepatocellular carcinoma who progressed on sorafenib treatment (RESORCE): a randomised, double-blind, placebo-controlled, phase 3 trial. *Lancet* 389, 56-66, (2017).

207. Liu, C. Y., Chen, K. F. & Chen, P. J. Treatment of Liver Cancer. *Cold Spring Harb Perspect Med* 5, a021535, (2015).

208. Cheemalapati, S. V. et al. Subcellular and in-vivo Nano-Endoscopy. *Sci Rep* 6, 34400, (2016).

209. Maher, S. P. et al. An adaptable soft-mold embossing process for fabricating optically-accessible, microfeature-based culture systems and application toward liver stage antimalarial compound testing. *Lab Chip* 20, 1124-1139, (2020).

210. Roth, A. et al. A comprehensive model for assessment of liver stage therapies targeting *Plasmodium vivax* and *Plasmodium falciparum*. *Nat Commun* 9, 1837, (2018).

211. Liu, D. et al. Spatial Multiomics Analysis Reveals Only Minor Genetic and Epigenetic Changes in Human Liver Cancer Stem-Like Cells Compared With Other Tumor Parenchymal Cells. *Front Cell Dev Biol* 10, 810687, (2022).

212. Zheng, C. et al. Landscape of Infiltrating T Cells in Liver Cancer Revealed by Single-Cell Sequencing. *Cell* 169, 1342-1356.e1316, (2017).

213. Liu, R. et al. Identifying critical transitions and their leading biomolecular networks in complex diseases. *Scientific Reports* 2, 813, (2012).

214. Wurmbach, E. et al. Genome-wide molecular profiles of HCV-induced dysplasia and hepatocellular carcinoma. *Hepatology* 45, 938-947, (2007).

In the preceding specification, all documents, acts, or information disclosed does not constitute an admission that the document, act, or information of any combination thereof was publicly available, known to the public, part of the general knowledge in the art, or was known to be relevant to solve any problem at the time of priority The disclosures of all publications cited above are expressly incorporated herein by reference, each in its entirety, to the same extent as if each were incorporated by reference individually.

While there has been described and illustrated specific embodiments of a method of treating cancer, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

The invention claimed is:

1. A method of inhibiting cancer cell proliferation consisting of:

administering, to the cancer cells a therapeutically effective amount of a first compound capable of inducing accumulation of heme precursor porphyrin metabolites; and subsequently administering, to the cancer cells, a therapeutically effective amount of a second compound capable of inducing cancer cell death wherein the second compound is selected from the group consisting of RAS-selective lethal (RSL3), ML 210, inhibitor of ferroptosis suppressor protein 1 (iFSP1), erastin, chloroquine, and combinations thereof wherein the second compound is administered about 24 hours after the administration of the first compound.

2. The method of claim 1, wherein the heme precursor metabolite is protoporphyrin IX (PPIX).

3. The method of claim 1, wherein concentration of the heme precursor porphyrin metabolites is at least 100-fold higher as compared to a control.

4. The method of claim 1, wherein the first compound is 5-aminolevulinate (ALA).

5. A method of inducing cancer cell death consisting of:

administering a therapeutically effective amount of a first compound to induce accumulation of heme precursor porphyrin metabolites; and subsequently administering a therapeutically effective amount of a second compound to induce the cancer cell death wherein the second compound is selected from the group consisting of RAS-selective lethal (RSL3), ML 210, inhibitor of ferroptosis suppressor protein 1 (iFSP1), erastin, chloroquine, and combinations thereof wherein the second compound is administered about 24 hours after the administration of the first compound.

6. The method of claim 5, wherein the heme precursor metabolite is protoporphyrin IX (PPIX).

7. The method of claim 5, wherein concentration of the heme precursor porphyrin metabolites is at least 100-fold higher as compared to a control.

8. The method of claim 5, wherein the first compound is 5-aminolevulinate (ALA).

* * * * *